(12) United States Patent
Sikora et al.

(10) Patent No.: US 9,492,200 B2
(45) Date of Patent: Nov. 15, 2016

(54) SUTURE SYSTEM AND METHOD

(71) Applicant: Arthrosurface Incorporated, Franklin, MA (US)

(72) Inventors: George Sikora, Bridgewater, MA (US); Steven W. Ek, Bolton, MA (US)

(73) Assignee: Arthrosurface Incorporated, Franklin, MA (US)

( * ) Notice: Subject to any disclaimer, the term of this patent is extended or adjusted under 35 U.S.C. 154(b) by 418 days.

(21) Appl. No.: 13/863,917

(22) Filed: Apr. 16, 2013

(65) Prior Publication Data

US 2014/0309689 A1    Oct. 16, 2014

(51) Int. Cl.
| | | |
|---|---|---|
| A61B 17/04 | (2006.01) | |
| A61B 17/68 | (2006.01) | |
| A61B 17/84 | (2006.01) | |
| A61B 17/16 | (2006.01) | |

(52) U.S. Cl.
CPC .......... *A61B 17/683* (2013.01); *A61B 17/0401* (2013.01); *A61B 17/1682* (2013.01); *A61B 17/842* (2013.01)

(58) Field of Classification Search
CPC ............ A61B 17/0401; A61B 17/683; A61B 17/1682
USPC ........................ 606/139, 144, 228, 232, 300
See application file for complete search history.

(56) References Cited

U.S. PATENT DOCUMENTS

| | | | |
|---|---|---|---|
| 103,645 | A | 5/1870 | Muscroft |
| 992,819 | A | 5/1911 | Springer |
| 1,451,610 | A | 4/1923 | Gestas |
| 2,267,925 | A | 12/1941 | Johnston |
| 2,379,984 | A | 7/1943 | Nereaux |
| 2,381,102 | A | 10/1943 | Boyd |
| 2,570,465 | A | 10/1951 | Lundholm |
| 3,176,395 | A | 4/1965 | Warner et al. |

(Continued)

FOREIGN PATENT DOCUMENTS

| | | |
|---|---|---|
| AU | 2001262308 | 12/2001 |
| AU | 2001259327 B2 | 2/2005 |

(Continued)

OTHER PUBLICATIONS

Partial supplementary European search report dated Mar. 25, 2015, issued in EP Patent Application No. 11751521.3, 6 pages.

(Continued)

*Primary Examiner* — Robert Lynch
(74) *Attorney, Agent, or Firm* — Grossman Tucker Perreault & Pfleger PLLC

(57) ABSTRACT

A suture system including a suture construct having a first reduction construct configured to be selectively arranged in an expanded state and a reduced state. The first reduction construct includes a first locking limb, a first contractible loop, and a first opposed loop disposed generally opposite to the first contractible loop, wherein reduction of the first opposed loop contracts the first contractible loop from the expanded state into the reduced state and secures the suture construct in the reduced state. The suture construct may also include a second reduction construct. Optionally, the suture system includes a first and a second pusher tube defining a first and a second lumen, respectively, wherein each pusher tubes are advanced over portions of opposed loops, respectively, and wherein distal portions of opposed loops extend beyond the pusher tubes, respectively.

32 Claims, 21 Drawing Sheets

(56) References Cited

U.S. PATENT DOCUMENTS

| | | |
|---|---|---|
| 3,351,115 A | 11/1967 | Boehlow |
| 3,715,763 A | 2/1973 | Link |
| 3,840,905 A | 10/1974 | Deane |
| 3,852,830 A | 12/1974 | Marmor |
| 4,016,651 A | 4/1977 | Kawahara et al. |
| 4,016,874 A | 4/1977 | Maffei et al. |
| 4,034,418 A | 7/1977 | Jackson et al. |
| D245,259 S | 8/1977 | Shen |
| 4,044,464 A | 8/1977 | Schiess et al. |
| 4,158,894 A | 6/1979 | Worrell |
| 4,304,011 A | 12/1981 | Whelan, III |
| 4,309,778 A | 1/1982 | Buechel et al. |
| 4,319,577 A | 3/1982 | Bofinger et al. |
| 4,330,891 A | 5/1982 | Brånemark et al. |
| 4,340,978 A | 7/1982 | Buechel et al. |
| 4,344,192 A | 8/1982 | Imbert |
| 4,433,687 A | 2/1984 | Burke et al. |
| 4,462,120 A | 7/1984 | Rambert et al. |
| 4,474,177 A | 10/1984 | Whiteside |
| 4,484,570 A | 11/1984 | Sutter et al. |
| 4,531,517 A | 7/1985 | Forte et al. |
| 4,535,768 A | 8/1985 | Hourahane et al. |
| 4,565,768 A | 1/1986 | Nonogaki et al. |
| 4,567,885 A | 2/1986 | Androphy |
| 4,634,720 A | 1/1987 | Dorman et al. |
| 4,655,752 A | 4/1987 | Honkanen et al. |
| 4,661,536 A | 4/1987 | Dorman et al. |
| 4,662,371 A | 5/1987 | Whipple et al. |
| 4,664,669 A | 5/1987 | Ohyabu et al. |
| 4,673,407 A | 6/1987 | Martin |
| 4,693,986 A | 9/1987 | Vit et al. |
| 4,708,139 A | 11/1987 | Dunbar, IV |
| 4,712,545 A | 12/1987 | Honkanen |
| 4,714,478 A | 12/1987 | Fischer |
| 4,719,908 A | 1/1988 | Averill et al. |
| 4,722,331 A | 2/1988 | Fox |
| 4,729,761 A | 3/1988 | White |
| 4,778,473 A | 10/1988 | Matthews et al. |
| 4,781,182 A | 11/1988 | Purnell et al. |
| 4,787,383 A | 11/1988 | Kenna |
| 4,788,970 A | 12/1988 | Kara et al. |
| 4,823,780 A | 4/1989 | Odensten et al. |
| 4,842,604 A | 6/1989 | Dorman et al. |
| 4,896,663 A | 1/1990 | Vandewalls |
| 4,911,153 A | 3/1990 | Border |
| 4,911,720 A | 3/1990 | Collier |
| 4,919,671 A | 4/1990 | Karpf |
| 4,920,958 A | 5/1990 | Walt et al. |
| 4,927,421 A | 5/1990 | Goble et al. |
| 4,936,853 A | 6/1990 | Fabian et al. |
| 4,938,778 A | 7/1990 | Ohyabu et al. |
| 4,940,467 A | 7/1990 | Tronzo |
| 4,945,904 A | 8/1990 | Bolton et al. |
| 4,955,916 A | 9/1990 | Carignan et al. |
| 4,976,037 A | 12/1990 | Hines |
| 4,978,258 A | 12/1990 | Lins |
| 4,979,957 A | 12/1990 | Hodorek |
| 4,989,110 A | 1/1991 | Zevin et al. |
| 4,990,163 A | 2/1991 | Ducheyne et al. |
| 4,997,434 A | 3/1991 | Seedhom et al. |
| 4,998,938 A | 3/1991 | Ghajar et al. |
| 5,007,930 A | 4/1991 | Dorman et al. |
| 5,019,104 A | 5/1991 | Whiteside et al. |
| 5,030,219 A | 7/1991 | Matsen, III et al. |
| 5,053,049 A | 10/1991 | Campbell |
| 5,092,895 A | 3/1992 | Albrektsson et al. |
| 5,100,405 A | 3/1992 | McLaren |
| 5,122,144 A | 6/1992 | Bert et al. |
| 5,127,413 A | 7/1992 | Ebert |
| 5,127,920 A | 7/1992 | MacArthur |
| 5,147,386 A | 9/1992 | Carignan et al. |
| 5,152,797 A | 10/1992 | Luckman et al. |
| 5,154,720 A | 10/1992 | Trott et al. |
| 5,180,384 A | 1/1993 | Mikhail |
| 5,192,291 A | 3/1993 | Pannek, Jr. |
| 5,194,066 A | 3/1993 | Van Zile |
| 5,201,881 A | 4/1993 | Evans |
| 5,207,753 A | 5/1993 | Badrinath |
| 5,211,647 A | 5/1993 | Schmieding |
| 5,224,945 A | 7/1993 | Pannek, Jr. |
| 5,234,435 A | 8/1993 | Seagrave, Jr. |
| 5,254,119 A | 10/1993 | Schreiber |
| 5,255,838 A | 10/1993 | Gladdish, Jr. et al. |
| 5,263,498 A | 11/1993 | Caspari et al. |
| 5,263,987 A | 11/1993 | Shah |
| 5,282,863 A | 2/1994 | Burton |
| 5,290,313 A | 3/1994 | Heldreth |
| 5,312,411 A | 5/1994 | Steele |
| 5,314,478 A | 5/1994 | Oka et al. |
| 5,314,482 A | 5/1994 | Goodfellow et al. |
| 5,324,295 A | 6/1994 | Shapiro |
| 5,326,366 A | 7/1994 | Pascarella et al. |
| 5,336,224 A | 8/1994 | Selman |
| 5,336,266 A | 8/1994 | Caspari et al. |
| 5,354,300 A | 10/1994 | Goble et al. |
| 5,358,525 A | 10/1994 | Fox et al. |
| 5,360,446 A | 11/1994 | Kennedy |
| 5,374,270 A | 12/1994 | McGuire et al. |
| 5,383,937 A | 1/1995 | Mikhail |
| 5,387,218 A | 2/1995 | Meswania |
| 5,395,376 A | 3/1995 | Caspari et al. |
| 5,395,401 A | 3/1995 | Bahler |
| 5,409,490 A | 4/1995 | Ethridge |
| 5,409,494 A | 4/1995 | Morgan |
| 5,413,608 A | 5/1995 | Keller |
| 5,423,822 A | 6/1995 | Hershberger |
| 5,423,823 A | 6/1995 | Schmieding |
| 5,425,733 A | 6/1995 | Schmieding |
| 5,458,643 A | 10/1995 | Oka et al. |
| 5,480,443 A | 1/1996 | Elias |
| 5,486,178 A | 1/1996 | Hodge |
| 5,509,918 A | 4/1996 | Romano |
| 5,514,139 A | 5/1996 | Goldstein et al. |
| 5,520,695 A | 5/1996 | Luckman |
| 5,522,900 A | 6/1996 | Hollister |
| 5,534,031 A | 7/1996 | Matsuzaki et al. |
| 5,540,696 A | 7/1996 | Booth, Jr. et al. |
| 5,562,664 A | 10/1996 | Durlacher et al. |
| 5,580,352 A | 12/1996 | Sekel |
| 5,580,353 A | 12/1996 | Mendes et al. |
| 5,591,170 A | 1/1997 | Spievack et al. |
| 5,593,448 A | 1/1997 | Dong |
| 5,593,450 A | 1/1997 | Scott et al. |
| 5,595,193 A | 1/1997 | Walus et al. |
| 5,597,273 A | 1/1997 | Hlrsch |
| 5,601,550 A | 2/1997 | Esser |
| 5,607,480 A | 3/1997 | Beaty |
| 5,616,146 A | 4/1997 | Murray |
| 5,620,055 A | 4/1997 | Javerlhac |
| 5,624,463 A | 4/1997 | Stone et al. |
| 5,632,745 A | 5/1997 | Schwartz |
| 5,634,927 A | 6/1997 | Houston et al. |
| 5,645,598 A | 7/1997 | Brosnahan, III |
| 5,681,311 A | 10/1997 | Foley et al. |
| 5,681,320 A | 10/1997 | McGuire |
| 5,682,886 A | 11/1997 | Delp et al. |
| 5,683,400 A | 11/1997 | McGuire |
| 5,683,465 A | 11/1997 | Shinn et al. |
| 5,683,466 A | 11/1997 | Viatle |
| 5,700,264 A | 12/1997 | Zucherman et al. |
| 5,700,265 A | 12/1997 | Romano |
| 5,702,401 A | 12/1997 | Shaffer |
| 5,702,465 A | 12/1997 | Burkinshaw |
| 5,702,467 A | 12/1997 | Gabriel et al. |
| 5,741,266 A | 4/1998 | Moran et al. |
| 5,765,973 A | 6/1998 | Hirsch et al. |
| 5,769,855 A | 6/1998 | Bertin et al. |
| 5,769,899 A | 6/1998 | Schwartz et al. |
| 5,771,310 A | 6/1998 | Vannah |
| 5,776,137 A | 7/1998 | Katz |
| 5,782,835 A | 7/1998 | Hart et al. |
| 5,800,440 A | 9/1998 | Stead |
| 5,810,851 A | 9/1998 | Yoon |
| 5,816,811 A | 10/1998 | Beaty |

(56) References Cited

U.S. PATENT DOCUMENTS

| | | | |
|---|---|---|---|
| 5,817,095 | A | 10/1998 | Smith |
| 5,824,087 | A | 10/1998 | Aspden et al. |
| 5,824,105 | A | 10/1998 | Ries et al. |
| RE36,020 | E | 12/1998 | Moore et al. |
| 5,879,396 | A | 3/1999 | Walston et al. |
| 5,882,350 | A | 3/1999 | Ralph et al. |
| 5,885,297 | A | 3/1999 | Matsen, III |
| 5,885,298 | A | 3/1999 | Herrington et al. |
| 5,888,210 | A | 3/1999 | Draenert |
| 5,893,889 | A | 4/1999 | Harrington |
| 5,895,390 | A | 4/1999 | Moran et al. |
| 5,911,126 | A | 6/1999 | Massen |
| 5,918,604 | A | 7/1999 | Whelan |
| 5,919,196 | A | 7/1999 | Bobic et al. |
| 5,928,239 | A | 7/1999 | Mirza |
| 5,928,241 | A | 7/1999 | Menut et al. |
| 5,928,286 | A | 7/1999 | Ashby et al. |
| 5,964,752 | A | 10/1999 | Stone |
| 5,964,768 | A | 10/1999 | Huebner |
| 5,964,808 | A | 10/1999 | Blaha et al. |
| 5,968,050 | A | 10/1999 | Torrie |
| 5,989,269 | A | 11/1999 | Vibe-Hansen et al. |
| 5,990,382 | A | 11/1999 | Fox |
| 5,997,543 | A | 12/1999 | Truscott |
| 5,997,582 | A | 12/1999 | Weiss |
| 6,004,323 | A | 12/1999 | Park et al. |
| 6,010,502 | A | 1/2000 | Bagby |
| 6,015,411 | A | 1/2000 | Ohkoshi et al. |
| 6,017,348 | A | 1/2000 | Hart et al. |
| 6,019,767 | A | 2/2000 | Howell |
| 6,019,790 | A | 2/2000 | Holmberg et al. |
| 6,033,410 | A | 3/2000 | McLean et al. |
| 6,045,554 | A | 4/2000 | Grooms et al. |
| 6,045,564 | A | 4/2000 | Walen |
| 6,052,909 | A | 4/2000 | Gardner |
| 6,059,831 | A | 5/2000 | Braslow |
| 6,063,091 | A | 5/2000 | Lombardo et al. |
| 6,069,295 | A | 5/2000 | Leitao |
| 6,071,310 | A | 6/2000 | Picha et al. |
| 6,081,741 | A | 6/2000 | Hollis |
| 6,086,593 | A | 7/2000 | Bonutti |
| 6,086,614 | A | 7/2000 | Mumme |
| 6,102,948 | A | 8/2000 | Brosnahan, III |
| 6,102,954 | A | 8/2000 | Albrektsson et al. |
| 6,120,511 | A | 9/2000 | Chan |
| 6,120,542 | A | 9/2000 | Camino et al. |
| 6,132,433 | A | 10/2000 | Whelan |
| 6,139,508 | A | 10/2000 | Simpson et al. |
| 6,146,385 | A | 11/2000 | Torrie et al. |
| 6,149,654 | A | 11/2000 | Johnson |
| 6,152,960 | A | 11/2000 | Pappas |
| 6,159,216 | A | 12/2000 | Burkinshaw et al. |
| 6,165,223 | A | 12/2000 | Metzger et al. |
| 6,168,626 | B1 | 1/2001 | Hyon et al. |
| 6,171,340 | B1 | 1/2001 | McDowell |
| 6,193,724 | B1 | 2/2001 | Chan |
| 6,206,885 | B1 | 3/2001 | Ghahremani et al. |
| 6,206,926 | B1 | 3/2001 | Pappas |
| 6,207,218 | B1 | 3/2001 | Layrolle et al. |
| 6,217,549 | B1 | 4/2001 | Selmon et al. |
| 6,217,619 | B1 | 4/2001 | Keller |
| 6,228,119 | B1 | 5/2001 | Ondrla et al. |
| 6,235,060 | B1 | 5/2001 | Kubein-Meesenburg et al. |
| 6,245,074 | B1 | 6/2001 | Allard et al. |
| 6,251,143 | B1 | 6/2001 | Schwartz et al. |
| 6,254,605 | B1 | 7/2001 | Howell |
| 6,270,347 | B1 | 8/2001 | Webster et al. |
| 6,280,474 | B1 | 8/2001 | Cassidy et al. |
| 6,299,645 | B1 | 10/2001 | Ogden |
| 6,299,648 | B1 | 10/2001 | Doubler et al. |
| 6,306,142 | B1 | 10/2001 | Johanson et al. |
| 6,310,116 | B1 | 10/2001 | Yasuda et al. |
| 6,315,798 | B1 | 11/2001 | Ashby et al. |
| 6,322,500 | B1 | 11/2001 | Sikora et al. |
| 6,328,752 | B1 | 12/2001 | Sjostrom et al. |
| 6,342,075 | B1 | 1/2002 | MacArthur |
| 6,358,251 | B1 | 3/2002 | Mirza |
| 6,358,253 | B1 | 3/2002 | Torrie et al. |
| 6,364,910 | B1 | 4/2002 | Shultz et al. |
| 6,375,658 | B1 | 4/2002 | Hangody et al. |
| 6,383,188 | B2 | 5/2002 | Kuslich |
| 6,402,785 | B1 | 6/2002 | Zdeblick et al. |
| 6,415,516 | B1 | 7/2002 | Tirado et al. |
| 6,416,518 | B1 | 7/2002 | DeMayo |
| 6,443,954 | B1 | 9/2002 | Bramlet et al. |
| 6,451,023 | B1 | 9/2002 | Salazar et al. |
| 6,461,373 | B2 | 10/2002 | Wyman et al. |
| 6,468,309 | B1 | 10/2002 | Lieberman |
| 6,478,801 | B1 | 11/2002 | Ralph et al. |
| 6,478,822 | B1 | 11/2002 | Leroux et al. |
| 6,482,210 | B1 | 11/2002 | Skiba et al. |
| 6,494,914 | B2 | 12/2002 | Brown |
| 6,517,541 | B1 | 2/2003 | Sesic |
| 6,520,964 | B2 | 2/2003 | Tallarida et al. |
| 6,527,754 | B1 | 3/2003 | Tallarida et al. |
| 6,530,956 | B1 | 3/2003 | Mansmann |
| 6,540,786 | B2 | 4/2003 | Chibrac et al. |
| 6,547,823 | B2 | 4/2003 | Scarborough et al. |
| 6,551,322 | B1 | 4/2003 | Lieberman |
| 6,554,866 | B1 | 4/2003 | Aicher et al. |
| 6,558,422 | B1 | 5/2003 | Baker et al. |
| 6,575,980 | B1 | 6/2003 | Robie et al. |
| 6,575,982 | B1 | 6/2003 | Bonutti |
| 6,585,666 | B2 | 7/2003 | Suh et al. |
| 6,589,281 | B2 | 7/2003 | Hyde, Jr. |
| 6,591,581 | B2 | 7/2003 | Schmieding |
| 6,599,321 | B2 | 7/2003 | Hyde et al. |
| 6,602,258 | B1 | 8/2003 | Katz |
| 6,607,561 | B2 | 8/2003 | Brannon |
| 6,610,067 | B2 | 8/2003 | Tallarida |
| 6,610,095 | B1 | 8/2003 | Pope et al. |
| 6,623,474 | B1 | 9/2003 | Ponzi |
| 6,626,950 | B2 | 9/2003 | Brown et al. |
| 6,629,997 | B2 | 10/2003 | Mansmann |
| 6,632,246 | B1 | 10/2003 | Simon et al. |
| 6,679,917 | B2 | 1/2004 | Ek |
| 6,720,469 | B1 | 4/2004 | Curtis et al. |
| 6,746,451 | B2 | 6/2004 | Middleton et al. |
| 6,755,837 | B2 | 6/2004 | Ebner |
| 6,755,865 | B2 | 6/2004 | Tarabishy |
| 6,770,078 | B2 | 8/2004 | Bonutti |
| 6,783,550 | B2 | 8/2004 | MacArthur |
| 6,783,551 | B1 | 8/2004 | Metzger |
| 6,802,864 | B2 | 10/2004 | Tornier |
| 6,814,735 | B1 | 11/2004 | Zirngibl |
| 6,827,722 | B1 | 12/2004 | Schoenefeld |
| 6,860,902 | B2 | 3/2005 | Reiley |
| 6,881,228 | B2 | 4/2005 | Zdeblick et al. |
| 6,884,246 | B1 | 4/2005 | Sonnabend et al. |
| 6,884,621 | B2 | 4/2005 | Liao et al. |
| 6,893,467 | B1 | 5/2005 | Bercovy |
| 6,923,813 | B2 | 8/2005 | Phillips et al. |
| 6,926,739 | B1 | 8/2005 | OConnor |
| 6,951,538 | B2 | 10/2005 | Ritland |
| 6,953,478 | B2 | 10/2005 | Bouttens et al. |
| 6,962,577 | B2 | 11/2005 | Tallarida et al. |
| 6,969,393 | B2 | 11/2005 | Pinczewski et al. |
| 6,984,248 | B2 | 1/2006 | Hyde, Jr. |
| 6,989,016 | B2 | 1/2006 | Tallarida et al. |
| 7,029,479 | B2 | 4/2006 | Tallarida |
| 7,048,767 | B2 | 5/2006 | Namavar |
| 7,063,717 | B2 | 6/2006 | St. Pierre et al. |
| 7,112,205 | B2 | 9/2006 | Carrison |
| 7,115,131 | B2 | 10/2006 | Engh et al. |
| 7,118,578 | B2 | 10/2006 | West, Jr. et al. |
| 7,156,880 | B2 | 1/2007 | Evans et al. |
| 7,160,305 | B2 | 1/2007 | Schmieding |
| 7,163,541 | B2 | 1/2007 | Ek |
| 7,166,133 | B2 | 1/2007 | Evans et al. |
| 7,192,431 | B2 | 3/2007 | Hangody et al. |
| 7,192,432 | B2 | 3/2007 | Wetzler et al. |
| 7,204,839 | B2 | 4/2007 | Dreyfuss et al. |
| 7,204,854 | B2 | 4/2007 | Guederian et al. |
| 7,235,107 | B2 | 6/2007 | Evans et al. |

(56) References Cited

U.S. PATENT DOCUMENTS

| | | |
|---|---|---|
| 7,238,189 B2 | 7/2007 | Schmieding et al. |
| 7,241,316 B2 | 7/2007 | Evans et al. |
| 7,264,634 B2 | 9/2007 | Schmieding |
| 7,290,347 B2 | 11/2007 | Augustino et al. |
| 7,303,577 B1 | 12/2007 | Dean |
| 7,311,702 B2 | 12/2007 | Tallarida et al. |
| 7,361,195 B2 | 4/2008 | Schwartz et al. |
| 7,368,065 B2 | 5/2008 | Yang et al. |
| 7,371,260 B2 | 5/2008 | Malinin |
| 7,462,199 B2 | 12/2008 | Justin et al. |
| 7,468,075 B2 | 12/2008 | Lang et al. |
| 7,476,250 B1 | 1/2009 | Mansmann |
| 7,491,235 B2 | 2/2009 | Fell |
| 7,501,073 B2 | 3/2009 | Wen et al. |
| 7,510,558 B2 | 3/2009 | Tallarida |
| 7,531,000 B2 | 5/2009 | Hodorek |
| 7,559,932 B2 | 7/2009 | Truckai et al. |
| 7,569,059 B2 | 8/2009 | Cerundolo |
| 7,572,291 B2 | 8/2009 | Gil et al. |
| 7,575,578 B2 | 8/2009 | Wetzler et al. |
| 7,578,824 B2 | 8/2009 | Justin et al. |
| 7,604,641 B2 | 10/2009 | Tallarida et al. |
| 7,611,653 B1 | 11/2009 | Elsner et al. |
| 7,618,451 B2 | 11/2009 | Berez et al. |
| 7,618,462 B2 | 11/2009 | Ek |
| 7,632,294 B2 | 12/2009 | Milbodker et al. |
| 7,641,658 B2 | 1/2010 | Shaolian et al. |
| 7,641,689 B2 | 1/2010 | Fell et al. |
| 7,670,381 B2 | 3/2010 | Schwartz |
| 7,678,151 B2 | 3/2010 | Ek |
| 7,682,540 B2 | 3/2010 | Boyan et al. |
| 7,687,462 B2 | 3/2010 | Ting et al. |
| 7,708,741 B1 | 5/2010 | Bonutti |
| 7,713,305 B2 | 5/2010 | Ek |
| 7,722,676 B2 | 5/2010 | Hanson et al. |
| 7,731,720 B2 | 6/2010 | Sand et al. |
| 7,731,738 B2 | 6/2010 | Jackson et al. |
| 7,738,187 B2 | 6/2010 | Pazidis et al. |
| 7,758,643 B2 | 7/2010 | Stone et al. |
| 7,806,872 B2 | 10/2010 | Ponzi |
| 7,815,645 B2 | 10/2010 | Haines |
| 7,828,853 B2 | 11/2010 | Ek et al. |
| 7,842,042 B2 | 11/2010 | Reay-Young et al. |
| 7,857,817 B2 | 12/2010 | Tallarida et al. |
| 7,896,883 B2 | 3/2011 | Ek et al. |
| 7,896,885 B2 | 3/2011 | Miniaci et al. |
| 7,901,408 B2 | 3/2011 | Ek et al. |
| 7,914,545 B2 | 3/2011 | Ek |
| 7,931,683 B2 | 4/2011 | Weber et al. |
| 7,951,163 B2 | 5/2011 | Ek |
| 7,955,382 B2 | 6/2011 | Flanagan et al. |
| 7,959,636 B2 | 6/2011 | Schmieding |
| 7,959,650 B2 | 6/2011 | Kaiser et al. |
| 7,959,681 B2 | 6/2011 | Lavi |
| 7,967,823 B2 | 6/2011 | Ammann et al. |
| 7,993,360 B2 | 8/2011 | Hacker et al. |
| 7,993,369 B2 | 8/2011 | Dreyfuss |
| 7,998,206 B2 | 8/2011 | Shepard |
| 8,012,206 B2 | 9/2011 | Schmieding |
| 8,021,367 B2 | 9/2011 | Bourke et al. |
| 8,038,652 B2 | 10/2011 | Morrison et al. |
| 8,038,678 B2 | 10/2011 | Schmieding et al. |
| 8,043,315 B2 | 10/2011 | Shepard |
| 8,043,319 B2 | 10/2011 | Lyon et al. |
| 8,048,079 B2 | 11/2011 | Iannarone |
| 8,048,157 B2 | 11/2011 | Albertorio |
| 8,057,478 B2 | 11/2011 | Kuczynski et al. |
| 8,062,301 B2 | 11/2011 | Ammann et al. |
| 8,062,319 B2 | 11/2011 | O'Quinn et al. |
| 8,083,746 B2 | 12/2011 | Novak |
| 8,083,749 B2 | 12/2011 | Taber |
| 8,083,803 B2 | 12/2011 | Albertorio et al. |
| 8,097,040 B2 | 1/2012 | Russo et al. |
| 8,137,406 B2 | 3/2012 | Novak et al. |
| 8,142,502 B2 | 3/2012 | Stone et al. |
| 8,147,559 B2 | 4/2012 | Tallarida et al. |
| 8,152,847 B2 | 4/2012 | Strzepa et al. |
| 8,157,867 B2 | 4/2012 | Goble et al. |
| 8,162,947 B2 | 4/2012 | Dreyfuss |
| 8,163,027 B2 | 4/2012 | Rhodes et al. |
| 8,167,951 B2 | 5/2012 | Ammann et al. |
| 8,177,738 B2 | 5/2012 | Schmieding et al. |
| 8,177,841 B2 | 5/2012 | Ek |
| 8,182,489 B2 | 5/2012 | Horacek |
| 8,202,282 B2 | 6/2012 | Schmieding et al. |
| 8,202,296 B2 | 6/2012 | Burkhart |
| 8,202,297 B2 | 6/2012 | Burkhart |
| 8,202,298 B2 | 6/2012 | Cook et al. |
| 8,202,306 B2 | 6/2012 | Dreyfuss |
| 8,202,318 B2 | 6/2012 | Willobee |
| 8,211,112 B2 | 7/2012 | Novak et al. |
| 8,221,455 B2 | 7/2012 | Shurnas et al. |
| 8,231,653 B2 | 7/2012 | Dreyfuss |
| 8,231,674 B2 | 7/2012 | Albertorio et al. |
| 8,236,000 B2 | 8/2012 | Ammann et al. |
| 8,267,977 B2 | 9/2012 | Roth |
| 8,298,247 B2 | 10/2012 | Sterrett et al. |
| 8,298,284 B2 | 10/2012 | Cassani |
| 8,303,830 B2 | 11/2012 | Tong et al. |
| 8,308,662 B2 | 11/2012 | Lo |
| 8,308,732 B2 | 11/2012 | Millett et al. |
| 8,323,347 B2 | 12/2012 | Guederian et al. |
| 8,328,716 B2 | 12/2012 | Schmieding et al. |
| 8,333,774 B2 | 12/2012 | Morrison |
| 8,343,186 B2 | 1/2013 | Dreyfuss et al. |
| 8,348,960 B2 | 1/2013 | Michel et al. |
| 8,348,975 B2 | 1/2013 | Dreyfuss |
| 8,353,915 B2 | 1/2013 | Helenbolt et al. |
| 8,361,159 B2 | 1/2013 | Ek |
| 8,377,068 B2 | 2/2013 | Aker et al. |
| 8,382,789 B2 | 2/2013 | Weber et al. |
| 8,382,810 B2 | 2/2013 | Peterson et al. |
| 8,388,624 B2 | 3/2013 | Ek et al. |
| 8,398,678 B2 | 3/2013 | Baker et al. |
| 8,409,209 B2 | 4/2013 | Ammann et al. |
| 8,409,250 B2 | 4/2013 | Schmieding et al. |
| 8,414,908 B2 | 4/2013 | Jin et al. |
| 8,419,794 B2 | 4/2013 | ElAttrache et al. |
| 8,425,554 B2 | 4/2013 | Denove et al. |
| 8,430,909 B2 | 4/2013 | Dreyfuss |
| 8,435,272 B2 | 5/2013 | Dougherty et al. |
| 8,439,976 B2 | 5/2013 | Albertorio et al. |
| 8,444,680 B2 | 5/2013 | Dooney, Jr. et al. |
| 8,460,317 B2 | 6/2013 | Merves |
| 8,460,318 B2 | 6/2013 | Murray et al. |
| 8,460,350 B2 | 6/2013 | Albertorio et al. |
| 8,460,379 B2 | 6/2013 | Albertorio et al. |
| 8,475,536 B2 | 7/2013 | Tong et al. |
| 8,486,072 B2 | 7/2013 | Haininger |
| 8,496,662 B2 | 7/2013 | Novak et al. |
| 8,506,573 B2 | 8/2013 | Dreyfuss et al. |
| 8,512,376 B2 | 8/2013 | Thornes |
| 8,512,411 B2 | 8/2013 | Sluss et al. |
| 8,523,872 B2 | 9/2013 | Ek |
| 8,535,330 B2 | 9/2013 | Sherman et al. |
| 8,535,703 B2 | 9/2013 | Schmieding et al. |
| 8,540,717 B2 | 9/2013 | Tallarida et al. |
| 8,540,777 B2 | 9/2013 | Ammann et al. |
| 8,540,778 B2 | 9/2013 | Rhodes et al. |
| 8,551,101 B2 | 10/2013 | Kuczynski |
| 8,579,940 B2 | 11/2013 | Dreyfuss et al. |
| 8,579,944 B2 | 11/2013 | Holloway et al. |
| 8,591,514 B2 | 11/2013 | Sherman |
| 8,591,523 B2 | 11/2013 | Weber |
| 8,591,544 B2 | 11/2013 | Jolly et al. |
| 8,591,578 B2 | 11/2013 | Albertorio et al. |
| 8,591,592 B2 | 11/2013 | Dreyfuss |
| 8,597,361 B2 | 12/2013 | Sidebotham et al. |
| 8,623,052 B2 | 1/2014 | Dreyfuss et al. |
| 8,628,573 B2 | 1/2014 | Roller et al. |
| 8,652,139 B2 | 2/2014 | Sterrett et al. |
| 8,663,230 B2 | 3/2014 | Miniaci et al. |
| 8,663,250 B2 | 3/2014 | Weber |
| 8,663,251 B2 | 3/2014 | Burkhart et al. |

(56) References Cited

U.S. PATENT DOCUMENTS

| | | |
|---|---|---|
| 8,663,279 B2 | 3/2014 | Burkhart et al. |
| 8,663,324 B2 | 3/2014 | Schmieding et al. |
| 8,663,333 B2 | 3/2014 | Metcalfe et al. |
| 8,668,738 B2 | 3/2014 | Schmieding et al. |
| 8,702,715 B2 | 4/2014 | Ammann et al. |
| 8,702,752 B2 | 4/2014 | Schmieding et al. |
| 8,709,052 B2 | 4/2014 | Ammann et al. |
| 8,709,091 B2 | 4/2014 | Rhodes et al. |
| 8,721,722 B2 | 5/2014 | Shah et al. |
| 8,728,131 B2 | 5/2014 | Di Giacomo et al. |
| 8,734,449 B2 | 5/2014 | Schmied et al. |
| 8,753,375 B2 | 6/2014 | Albertorio |
| 8,758,356 B2 | 6/2014 | Fearon et al. |
| 8,764,797 B2 | 7/2014 | Dreyfuss et al. |
| 8,764,807 B2 | 7/2014 | Michel et al. |
| 8,764,839 B2 | 7/2014 | Rhodes et al. |
| 8,771,279 B2 | 7/2014 | Philippon et al. |
| 8,771,351 B2 | 7/2014 | ElAttrache et al. |
| 8,784,423 B2 | 7/2014 | Kowarsch et al. |
| 8,790,401 B2 | 7/2014 | Schmieding et al. |
| 8,801,755 B2 | 8/2014 | Dreyfuss et al. |
| 8,821,541 B2 | 9/2014 | Dreyfuss et al. |
| 8,834,475 B2 | 9/2014 | Ammann et al. |
| 8,834,521 B2 | 9/2014 | Pinto et al. |
| 8,840,619 B2 | 9/2014 | Zajac et al. |
| 8,840,643 B2 | 9/2014 | Dreyfuss |
| 8,852,190 B2 | 10/2014 | Sherman |
| 8,852,201 B2 | 10/2014 | Schmieding et al. |
| 8,858,560 B2 | 10/2014 | Bradley et al. |
| 8,864,827 B2 | 10/2014 | Ek |
| 8,870,877 B2 | 10/2014 | Koogle, Jr. |
| 8,876,900 B2 | 11/2014 | Guederian et al. |
| 8,882,833 B2 | 11/2014 | Saylor et al. |
| 8,882,847 B2 | 11/2014 | Burdulis, Jr. et al. |
| 8,888,781 B2 | 11/2014 | Sterrett |
| 8,888,785 B2 | 11/2014 | Ammann et al. |
| 8,888,815 B2 | 11/2014 | Holmes, Jr. |
| 8,906,026 B2 | 12/2014 | Ammann et al. |
| 8,911,457 B2 | 12/2014 | Koogle, Jr. et al. |
| 8,920,497 B2 | 12/2014 | Albertorio et al. |
| 8,926,615 B2 | 1/2015 | Ek |
| 8,927,283 B2 | 1/2015 | Komvopoulos et al. |
| 8,939,980 B2 | 1/2015 | Schmieding et al. |
| 8,939,999 B2 | 1/2015 | Sterrett et al. |
| 8,956,369 B2 | 2/2015 | Millett et al. |
| 8,961,538 B2 | 2/2015 | Koogle, Jr. et al. |
| 8,961,575 B2 | 2/2015 | Choinski |
| 8,961,614 B2 | 2/2015 | Ek et al. |
| 8,974,537 B2 | 3/2015 | Dreyfuss |
| 8,986,346 B2 | 3/2015 | Dreyfuss |
| 9,005,245 B2 | 4/2015 | Thornes et al. |
| 9,005,246 B2 | 4/2015 | Burkhart et al. |
| 9,044,343 B2 | 6/2015 | Ek |
| 9,055,955 B2 | 6/2015 | Ek et al. |
| 9,066,716 B2 | 6/2015 | Sikora et al. |
| 9,072,510 B2 | 7/2015 | Thornes et al. |
| 9,072,555 B2 | 7/2015 | Michel |
| 9,078,650 B2 | 7/2015 | Weber |
| 9,078,661 B2 | 7/2015 | Gallo |
| 9,089,363 B2 | 7/2015 | Dooney, Jr. et al. |
| 9,089,433 B2 | 7/2015 | Karnes et al. |
| 9,095,641 B2 | 8/2015 | Albertorio |
| 9,101,366 B2 | 8/2015 | Sterrett et al. |
| 9,101,461 B2 | 8/2015 | Albertorio et al. |
| 9,107,653 B2 | 8/2015 | Sullivan |
| 9,107,676 B2 | 8/2015 | Burkhart et al. |
| 9,113,859 B2 | 8/2015 | Dooney, Jr. et al. |
| 9,113,920 B2 | 8/2015 | Ammann et al. |
| 9,138,223 B2 | 9/2015 | Jolly et al. |
| 9,138,237 B2 | 9/2015 | Meade et al. |
| 9,138,241 B2 | 9/2015 | Kuczynski |
| 9,138,246 B2 | 9/2015 | Anderson et al. |
| 9,138,274 B1 | 9/2015 | Biesinger et al. |
| 9,146,576 B2 | 9/2015 | Schmieding et al. |
| 9,168,124 B2 | 10/2015 | Guerra et al. |
| 9,179,907 B2 | 11/2015 | ElAttrache et al. |
| 9,179,950 B2 | 11/2015 | Zajac et al. |
| 9,186,432 B2 | 11/2015 | Mazzocca et al. |
| 9,204,873 B2 | 12/2015 | Tallarida et al. |
| 9,204,874 B2 | 12/2015 | Denove et al. |
| 9,204,960 B2 | 12/2015 | Albertorio et al. |
| 9,216,017 B2 | 12/2015 | Burkhart |
| 9,216,022 B2 | 12/2015 | Karnes et al. |
| 9,216,090 B2 | 12/2015 | Metcalfe |
| 9,216,091 B2 | 12/2015 | Hardy et al. |
| 9,226,743 B2 | 1/2016 | Dreyfuss et al. |
| 9,226,815 B2 | 1/2016 | Schmieding et al. |
| 9,283,076 B2 | 3/2016 | Sikora et al. |
| 9,295,556 B2 | 3/2016 | Perez, III et al. |
| 9,301,745 B2 | 4/2016 | Dreyfuss |
| 9,301,847 B2 | 4/2016 | Guederian et al. |
| 9,320,512 B2 | 4/2016 | Dooney, Jr. |
| 9,332,979 B2 | 5/2016 | Sullivan et al. |
| 9,333,019 B2 | 5/2016 | Khosla et al. |
| 9,345,471 B2 | 5/2016 | Sullivan |
| 9,351,722 B2 | 5/2016 | Koogle, Jr. et al. |
| 9,351,745 B2 | 5/2016 | Ek et al. |
| 9,357,989 B2 | 6/2016 | Tallarida et al. |
| 9,358,029 B2 | 6/2016 | Sikora et al. |
| 9,364,214 B2 | 6/2016 | Courage |
| 9,381,022 B2 | 7/2016 | Bradley et al. |
| 9,381,053 B2 | 7/2016 | Parsons et al. |
| 9,393,010 B2 | 7/2016 | Murray et al. |
| 9,402,730 B2 | 8/2016 | Lederman et al. |
| 9,421,007 B2 | 8/2016 | Brady et al. |
| 9,421,008 B2 | 8/2016 | Burkhart et al. |
| 9,421,010 B2 | 8/2016 | Dreyfuss |
| 9,421,086 B2 | 8/2016 | Roller et al. |
| 9,421,105 B2 | 8/2016 | Metcalfe et al. |
| 2001/0010023 A1 | 7/2001 | Schwartz et al. |
| 2001/0012967 A1 | 8/2001 | Mosseri |
| 2001/0016775 A1 | 8/2001 | Scarborough et al. |
| 2001/0034526 A1 | 10/2001 | Kuslich et al. |
| 2001/0039455 A1 | 11/2001 | Simon et al. |
| 2001/0053914 A1 | 12/2001 | Landry et al. |
| 2001/0056266 A1 | 12/2001 | Tallarida et al. |
| 2002/0022847 A1 | 2/2002 | Ray, III et al. |
| 2002/0022889 A1 | 2/2002 | Chibrac et al. |
| 2002/0022890 A1 | 2/2002 | Jacobsson et al. |
| 2002/0049444 A1 | 4/2002 | Knox |
| 2002/0055783 A1 | 5/2002 | Tallarida et al. |
| 2002/0082701 A1 | 6/2002 | Zdeblick et al. |
| 2002/0106393 A1 | 8/2002 | Bianchi et al. |
| 2002/0138150 A1 | 9/2002 | Leclercq |
| 2002/0143342 A1 | 10/2002 | Hangody et al. |
| 2002/0147498 A1 | 10/2002 | Tallarida et al. |
| 2002/0155144 A1 | 10/2002 | Troczynski et al. |
| 2002/0156480 A1 | 10/2002 | Overes et al. |
| 2002/0173797 A1 | 11/2002 | Van Zile et al. |
| 2002/0183760 A1 | 12/2002 | McGovern et al. |
| 2003/0028196 A1 | 2/2003 | Bonutti |
| 2003/0060887 A1 | 3/2003 | Ek |
| 2003/0065391 A1 | 4/2003 | Re et al. |
| 2003/0100953 A1 | 5/2003 | Rosa et al. |
| 2003/0105465 A1 | 6/2003 | Schmieding et al. |
| 2003/0120276 A1 | 6/2003 | Tallarida et al. |
| 2003/0120278 A1 | 6/2003 | Morgan et al. |
| 2003/0130741 A1 | 7/2003 | McMinn |
| 2003/0144736 A1 | 7/2003 | Sennett |
| 2003/0171756 A1 | 9/2003 | Fallin et al. |
| 2003/0171820 A1 | 9/2003 | Wilshaw et al. |
| 2003/0181878 A1 | 9/2003 | Tallarida et al. |
| 2003/0195470 A1 | 10/2003 | Ponzi |
| 2003/0204195 A1 | 10/2003 | Keane et al. |
| 2003/0204267 A1 | 10/2003 | Hazebrouck et al. |
| 2003/0216669 A1 | 11/2003 | Lang et al. |
| 2003/0216742 A1 | 11/2003 | Wetzler et al. |
| 2003/0225456 A1 | 12/2003 | Ek |
| 2003/0225457 A1 | 12/2003 | Justin et al. |
| 2003/0229352 A1 | 12/2003 | Penenberg |
| 2004/0015170 A1 | 1/2004 | Tallarida et al. |
| 2004/0033212 A1 | 2/2004 | Thomson et al. |
| 2004/0034359 A1 | 2/2004 | Schmieding et al. |
| 2004/0034437 A1 | 2/2004 | Schmieding |

(56) References Cited

U.S. PATENT DOCUMENTS

| | | |
|---|---|---|
| 2004/0039389 A1 | 2/2004 | West, Jr. et al. |
| 2004/0082906 A1 | 4/2004 | Tallarida et al. |
| 2004/0083005 A1 | 4/2004 | Jacobsson et al. |
| 2004/0092946 A1 | 5/2004 | Bagga et al. |
| 2004/0106928 A1 | 6/2004 | Ek |
| 2004/0133276 A1 | 7/2004 | Lang et al. |
| 2004/0138754 A1 | 7/2004 | Lang et al. |
| 2004/0138758 A1 | 7/2004 | Evans et al. |
| 2004/0148030 A1 | 7/2004 | Ek |
| 2004/0153086 A1 | 8/2004 | Sanford |
| 2004/0153087 A1 | 8/2004 | Sanford et al. |
| 2004/0167632 A1 | 8/2004 | Wen et al. |
| 2004/0167633 A1 | 8/2004 | Wen et al. |
| 2004/0176775 A1 | 9/2004 | Burkus et al. |
| 2004/0186582 A1 | 9/2004 | Yasuda et al. |
| 2004/0193172 A1 | 9/2004 | Ross et al. |
| 2004/0193175 A1 | 9/2004 | Maroney et al. |
| 2004/0193267 A1 | 9/2004 | Jones et al. |
| 2004/0193268 A1 | 9/2004 | Hazebrouck |
| 2004/0193281 A1 | 9/2004 | Grimes |
| 2004/0199166 A1 | 10/2004 | Schmieding et al. |
| 2004/0204760 A1 | 10/2004 | Fitz et al. |
| 2004/0210309 A1 | 10/2004 | Denzer et al. |
| 2004/0220574 A1 | 11/2004 | Pelo et al. |
| 2004/0230315 A1 | 11/2004 | Ek |
| 2004/0260303 A1 | 12/2004 | Carrison |
| 2005/0015153 A1 | 1/2005 | Gobel et al. |
| 2005/0038520 A1 | 2/2005 | Binette et al. |
| 2005/0043805 A1 | 2/2005 | Chudik |
| 2005/0043808 A1 | 2/2005 | Felt et al. |
| 2005/0049716 A1 | 3/2005 | Wagener et al. |
| 2005/0065612 A1 | 3/2005 | Winslow |
| 2005/0071014 A1 | 3/2005 | Barnett et al. |
| 2005/0075642 A1 | 4/2005 | Felt |
| 2005/0085909 A1 | 4/2005 | Eisermann |
| 2005/0090905 A1 | 4/2005 | Hawkins et al. |
| 2005/0119758 A1 | 6/2005 | Alexander et al. |
| 2005/0143731 A1 | 6/2005 | Justin et al. |
| 2005/0143745 A1 | 6/2005 | Hodorek et al. |
| 2005/0143821 A1 | 6/2005 | Zdeblick et al. |
| 2005/0143831 A1 | 6/2005 | Justin et al. |
| 2005/0149044 A1 | 7/2005 | Justin et al. |
| 2005/0154398 A1 | 7/2005 | Miniaci et al. |
| 2005/0165487 A1 | 7/2005 | Muhanna et al. |
| 2005/0177171 A1 | 8/2005 | Wetzler et al. |
| 2005/0209705 A1 | 9/2005 | Niederauer et al. |
| 2005/0222687 A1 | 10/2005 | Vunjak-Novakovic et al. |
| 2005/0229323 A1 | 10/2005 | Mills et al. |
| 2005/0234461 A1 | 10/2005 | Burdulis, Jr. et al. |
| 2005/0251268 A1 | 11/2005 | Truncale |
| 2005/0273112 A1 | 12/2005 | McNamara |
| 2005/0287187 A1 | 12/2005 | Mansmann |
| 2006/0004461 A1 | 1/2006 | Justin et al. |
| 2006/0009774 A1 | 1/2006 | Goble et al. |
| 2006/0020343 A1 | 1/2006 | Ek |
| 2006/0052878 A1 | 3/2006 | Schmieding |
| 2006/0058744 A1 | 3/2006 | Tallarida et al. |
| 2006/0058809 A1 | 3/2006 | Zink et al. |
| 2006/0058883 A1 | 3/2006 | Aram et al. |
| 2006/0069394 A1 | 3/2006 | Weiler et al. |
| 2006/0074430 A1 | 4/2006 | Deffenbaugh et al. |
| 2006/0085006 A1 | 4/2006 | Ek |
| 2006/0085077 A1 | 4/2006 | Cook et al. |
| 2006/0105015 A1 | 5/2006 | Perla et al. |
| 2006/0111787 A1 | 5/2006 | Bailie et al. |
| 2006/0121080 A1 | 6/2006 | Lye et al. |
| 2006/0142772 A1 | 6/2006 | Ralph et al. |
| 2006/0149370 A1 | 7/2006 | Schmieding et al. |
| 2006/0154206 A1 | 7/2006 | Petersson et al. |
| 2006/0167560 A1 | 7/2006 | Heck et al. |
| 2006/0184187 A1 | 8/2006 | Surti |
| 2006/0190002 A1 | 8/2006 | Tallarida |
| 2006/0195112 A1 | 8/2006 | Ek |
| 2006/0217728 A1 | 9/2006 | Chervitz et al. |
| 2006/0229726 A1 | 10/2006 | Ek |
| 2006/0271059 A1 | 11/2006 | Reay-Young et al. |
| 2007/0005143 A1 | 1/2007 | Ek |
| 2007/0038302 A1 | 2/2007 | Shultz et al. |
| 2007/0038307 A1 | 2/2007 | Webster et al. |
| 2007/0073394 A1 | 3/2007 | Seedhom et al. |
| 2007/0093842 A1 | 4/2007 | Schmieding |
| 2007/0093848 A1 | 4/2007 | Harris et al. |
| 2007/0093890 A1 | 4/2007 | Eliasen et al. |
| 2007/0093896 A1 | 4/2007 | Malinin |
| 2007/0118136 A1 | 5/2007 | Ek |
| 2007/0118224 A1 | 5/2007 | Shah et al. |
| 2007/0123921 A1 | 5/2007 | Ek |
| 2007/0134291 A1 | 6/2007 | Ting et al. |
| 2007/0173850 A1 | 7/2007 | Rangaiah et al. |
| 2007/0179608 A1 | 8/2007 | Ek |
| 2007/0233128 A1 | 10/2007 | Schmieding et al. |
| 2007/0244484 A1 | 10/2007 | Luginbuehl |
| 2007/0250067 A1 | 10/2007 | Schmieding et al. |
| 2007/0255399 A1 | 11/2007 | Eliasen et al. |
| 2007/0255412 A1 | 11/2007 | Hajaj et al. |
| 2007/0265700 A1 | 11/2007 | Eliasen et al. |
| 2007/0270711 A1 | 11/2007 | Gil et al. |
| 2007/0270873 A1 | 11/2007 | Flickinger et al. |
| 2007/0282455 A1 | 12/2007 | Luginbuehl et al. |
| 2007/0288031 A1 | 12/2007 | Dreyfuss et al. |
| 2007/0299519 A1 | 12/2007 | Schmieding |
| 2007/0299529 A1 | 12/2007 | Rhodes et al. |
| 2008/0004659 A1 | 1/2008 | Burkhart et al. |
| 2008/0015607 A1 | 1/2008 | D'Alessio et al. |
| 2008/0015709 A1 | 1/2008 | Evans et al. |
| 2008/0027430 A1 | 1/2008 | Montgomery et al. |
| 2008/0033443 A1 | 2/2008 | Sikora et al. |
| 2008/0033447 A1 | 2/2008 | Sand |
| 2008/0046084 A1 | 2/2008 | Sledge |
| 2008/0071381 A1 | 3/2008 | Buscher et al. |
| 2008/0086139 A1 | 4/2008 | Bourke et al. |
| 2008/0086152 A1* | 4/2008 | McKay .............. A61B 17/0469 606/139 |
| 2008/0097618 A1 | 4/2008 | Baker et al. |
| 2008/0103506 A1 | 5/2008 | Volpi et al. |
| 2008/0138611 A1 | 6/2008 | Yasuzawa et al. |
| 2008/0154271 A1 | 6/2008 | Berberich et al. |
| 2008/0172125 A1 | 7/2008 | Ek |
| 2008/0183290 A1 | 7/2008 | Baird et al. |
| 2008/0188935 A1 | 8/2008 | Saylor et al. |
| 2008/0195113 A1 | 8/2008 | Sikora |
| 2008/0208201 A1 | 8/2008 | Moindreau et al. |
| 2008/0243262 A1 | 10/2008 | Lee |
| 2008/0243263 A1 | 10/2008 | Lee et al. |
| 2008/0262500 A1 | 10/2008 | Collazo |
| 2008/0262625 A1 | 10/2008 | Spriano et al. |
| 2008/0275451 A1 | 11/2008 | McAllister et al. |
| 2008/0275512 A1 | 11/2008 | Albertorio et al. |
| 2008/0294168 A1 | 11/2008 | Wieland |
| 2008/0306483 A1 | 12/2008 | Iannarone |
| 2008/0317807 A1 | 12/2008 | Lu et al. |
| 2009/0018543 A1 | 1/2009 | Ammann et al. |
| 2009/0035722 A1 | 2/2009 | Balasundaram et al. |
| 2009/0054899 A1 | 2/2009 | Ammann et al. |
| 2009/0069816 A1 | 3/2009 | Sasing et al. |
| 2009/0076512 A1 | 3/2009 | Ammann et al. |
| 2009/0088753 A1 | 4/2009 | Aram et al. |
| 2009/0088858 A1 | 4/2009 | Zinger et al. |
| 2009/0105772 A1 | 4/2009 | Seebeck et al. |
| 2009/0112211 A1 | 4/2009 | Johnstone |
| 2009/0138077 A1 | 5/2009 | Weber et al. |
| 2009/0143783 A1 | 6/2009 | Dower |
| 2009/0143784 A1 | 6/2009 | Petersen et al. |
| 2009/0149860 A1 | 6/2009 | Scribner et al. |
| 2009/0198288 A1 | 8/2009 | Hoof et al. |
| 2009/0210057 A1 | 8/2009 | Liao et al. |
| 2009/0216268 A1 | 8/2009 | Panter |
| 2009/0216285 A1 | 8/2009 | Ek et al. |
| 2009/0220561 A1 | 9/2009 | Jin et al. |
| 2009/0222012 A1 | 9/2009 | Karnes et al. |
| 2009/0228105 A1 | 9/2009 | Son et al. |
| 2009/0234452 A1 | 9/2009 | Steiner et al. |
| 2009/0264889 A1 | 10/2009 | Long et al. |
| 2009/0264928 A1 | 10/2009 | Blain |

(56) References Cited

U.S. PATENT DOCUMENTS

| | | |
|---|---|---|
| 2009/0275950 A1 | 11/2009 | Sterrett et al. |
| 2009/0276052 A1 | 11/2009 | Regala et al. |
| 2009/0283701 A1 | 11/2009 | Ogawa |
| 2010/0003638 A1 | 1/2010 | Collins et al. |
| 2010/0015244 A1 | 1/2010 | Jain et al. |
| 2010/0028387 A1 | 2/2010 | Balasundaram et al. |
| 2010/0028999 A1 | 2/2010 | Nain |
| 2010/0036381 A1 | 2/2010 | Vanleeuwen et al. |
| 2010/0057197 A1 | 3/2010 | Weber et al. |
| 2010/0082035 A1 | 4/2010 | Keefer |
| 2010/0087829 A1 | 4/2010 | Metzger et al. |
| 2010/0092535 A1 | 4/2010 | Cook et al. |
| 2010/0112519 A1 | 5/2010 | Hall et al. |
| 2010/0136289 A1 | 6/2010 | Extrand et al. |
| 2010/0168854 A1 | 7/2010 | Luers et al. |
| 2010/0185294 A1 | 7/2010 | Ek |
| 2010/0217315 A1 | 8/2010 | Jolly et al. |
| 2010/0227372 A1 | 9/2010 | Bilek et al. |
| 2010/0249930 A1 | 9/2010 | Myers |
| 2010/0256645 A1 | 10/2010 | Zajac et al. |
| 2010/0256758 A1 | 10/2010 | Gordon et al. |
| 2010/0268227 A1 | 10/2010 | Tong et al. |
| 2010/0268238 A1 | 10/2010 | Sikora et al. |
| 2010/0268330 A1 | 10/2010 | Tong et al. |
| 2010/0268346 A1 | 10/2010 | Tong et al. |
| 2010/0268347 A1 | 10/2010 | Tong et al. |
| 2011/0009964 A1 | 1/2011 | Schwartz et al. |
| 2011/0035012 A1 | 2/2011 | Linares |
| 2011/0059312 A1 | 3/2011 | Howling et al. |
| 2011/0066242 A1 | 3/2011 | Lu et al. |
| 2011/0085968 A1 | 4/2011 | Jin et al. |
| 2011/0087280 A1 | 4/2011 | Albertorio |
| 2011/0106271 A1 | 5/2011 | Regala et al. |
| 2011/0123951 A1 | 5/2011 | Lomicka |
| 2011/0125263 A1 | 5/2011 | Webster et al. |
| 2011/0125277 A1 | 5/2011 | Nygren et al. |
| 2011/0152869 A1 | 6/2011 | Ek et al. |
| 2011/0159070 A1 | 6/2011 | Jin et al. |
| 2011/0190902 A1 | 8/2011 | Tong et al. |
| 2011/0196367 A1 | 8/2011 | Gallo |
| 2011/0213375 A1 | 9/2011 | Sikora et al. |
| 2011/0236435 A1 | 9/2011 | Biris |
| 2011/0238069 A1 | 9/2011 | Zajac et al. |
| 2011/0251621 A1 | 10/2011 | Sluss et al. |
| 2011/0257753 A1 | 10/2011 | Gordon et al. |
| 2011/0300186 A1 | 12/2011 | Hellstrom et al. |
| 2011/0301716 A1 | 12/2011 | Sirivisoot et al. |
| 2012/0022656 A1 | 1/2012 | Lavi |
| 2012/0027837 A1 | 2/2012 | DeMuth et al. |
| 2012/0051489 A1 | 3/2012 | Varanasi et al. |
| 2012/0058328 A1 | 3/2012 | Tourvieille et al. |
| 2012/0065732 A1 | 3/2012 | Roller et al. |
| 2012/0109136 A1 | 5/2012 | Bourque et al. |
| 2012/0109222 A1 | 5/2012 | Goel et al. |
| 2012/0116502 A1 | 5/2012 | Su et al. |
| 2012/0123474 A1 | 5/2012 | Zajac et al. |
| 2012/0123541 A1 | 5/2012 | Albertorio et al. |
| 2012/0128666 A1 | 5/2012 | Pébay et al. |
| 2012/0150225 A1 | 6/2012 | Burkhart et al. |
| 2012/0150286 A1 | 6/2012 | Weber et al. |
| 2012/0165868 A1 | 6/2012 | Burkhart et al. |
| 2012/0183799 A1 | 7/2012 | Steele et al. |
| 2012/0185058 A1 | 7/2012 | Albertorio et al. |
| 2012/0189833 A1 | 7/2012 | Suchanek et al. |
| 2012/0189844 A1 | 7/2012 | Jain et al. |
| 2012/0209278 A1 | 8/2012 | Ries et al. |
| 2012/0214128 A1 | 8/2012 | Collins et al. |
| 2012/0215310 A1 | 8/2012 | Sharp et al. |
| 2012/0221111 A1 | 8/2012 | Burkhead, Jr. et al. |
| 2012/0265298 A1 | 10/2012 | Schmieding et al. |
| 2012/0330357 A1 | 12/2012 | Thal |
| 2013/0022943 A1 | 1/2013 | Collins et al. |
| 2013/0023907 A1 | 1/2013 | Sterrett et al. |
| 2013/0023927 A1 | 1/2013 | Cassani |
| 2013/0046312 A1 | 2/2013 | Millett et al. |
| 2013/0096563 A1 | 4/2013 | Meade et al. |
| 2013/0096612 A1 | 4/2013 | Zajac et al. |
| 2013/0103104 A1 | 4/2013 | Krupp et al. |
| 2013/0110165 A1 | 5/2013 | Burkhart et al. |
| 2013/0138108 A1 | 5/2013 | Dreyfuss et al. |
| 2013/0138150 A1 | 5/2013 | Baker et al. |
| 2013/0150885 A1 | 6/2013 | Dreyfuss |
| 2013/0150975 A1 | 6/2013 | Iannotti et al. |
| 2013/0165954 A1 | 6/2013 | Dreyfuss et al. |
| 2013/0165972 A1 | 6/2013 | Sullivan |
| 2013/0178871 A1 | 7/2013 | Koogle, Jr. et al. |
| 2013/0184818 A1 | 7/2013 | Coughlin et al. |
| 2013/0190819 A1* | 7/2013 | Norton ............... A61B 17/0401 606/232 |
| 2013/0190885 A1 | 7/2013 | Ammann et al. |
| 2013/0204257 A1 | 8/2013 | Zajac |
| 2013/0204259 A1 | 8/2013 | Zajac |
| 2013/0205936 A1 | 8/2013 | Schmieding et al. |
| 2013/0218176 A1 | 8/2013 | Denove et al. |
| 2013/0238099 A1 | 9/2013 | Hardy et al. |
| 2013/0245775 A1 | 9/2013 | Metcalfe |
| 2013/0268073 A1 | 10/2013 | Albertorio et al. |
| 2013/0289570 A1 | 10/2013 | Chao |
| 2013/0304209 A1 | 11/2013 | Schmieding et al. |
| 2013/0331886 A1 | 12/2013 | Thornes |
| 2013/0338722 A1 | 12/2013 | Yalizis |
| 2013/0338792 A1 | 12/2013 | Schmieding et al. |
| 2013/0344600 A1 | 12/2013 | Jin et al. |
| 2013/0345747 A1 | 12/2013 | Dreyfuss |
| 2013/0345748 A1 | 12/2013 | Dreyfuss |
| 2014/0012267 A1 | 1/2014 | Skiora et al. |
| 2014/0012389 A1 | 1/2014 | Ek |
| 2014/0052178 A1 | 2/2014 | Dooney, Jr. |
| 2014/0052179 A1 | 2/2014 | Dreyfuss et al. |
| 2014/0074164 A1 | 3/2014 | Dreyfuss et al. |
| 2014/0074239 A1 | 3/2014 | Albertorio et al. |
| 2014/0079921 A1 | 3/2014 | De Volder |
| 2014/0081273 A1 | 3/2014 | Sherman |
| 2014/0081399 A1 | 3/2014 | Roller et al. |
| 2014/0088601 A1 | 3/2014 | Kuczynski |
| 2014/0088602 A1 | 3/2014 | Ammann et al. |
| 2014/0114322 A1 | 4/2014 | Perez, III |
| 2014/0114367 A1 | 4/2014 | Jolly et al. |
| 2014/0121700 A1 | 5/2014 | Dreyfuss et al. |
| 2014/0121701 A1 | 5/2014 | Dreyfuss et al. |
| 2014/0128889 A1 | 5/2014 | Sullivan et al. |
| 2014/0128915 A1 | 5/2014 | Dreyfuss et al. |
| 2014/0128921 A1 | 5/2014 | Parsons et al. |
| 2014/0155902 A1 | 6/2014 | Sikora et al. |
| 2014/0188232 A1 | 7/2014 | Metcalfe et al. |
| 2014/0194880 A1 | 7/2014 | Schmieding et al. |
| 2014/0228849 A1 | 8/2014 | Sterrett et al. |
| 2014/0236306 A1 | 8/2014 | Karnes et al. |
| 2014/0243439 A1 | 8/2014 | Papangelou et al. |
| 2014/0243891 A1 | 8/2014 | Schmieding et al. |
| 2014/0243892 A1 | 8/2014 | Choinski |
| 2014/0243976 A1 | 8/2014 | Schmieding et al. |
| 2014/0257297 A1 | 9/2014 | Koogle, Jr. et al. |
| 2014/0257299 A1 | 9/2014 | Berelsman et al. |
| 2014/0257384 A1 | 9/2014 | Dreyfuss et al. |
| 2014/0276841 A1 | 9/2014 | Albertorio et al. |
| 2014/0276990 A1 | 9/2014 | Perez, III |
| 2014/0277020 A1 | 9/2014 | Koogle et al. |
| 2014/0277121 A1* | 9/2014 | Pilgeram ............ A61B 17/0401 606/228 |
| 2014/0277134 A1 | 9/2014 | ElAttrache et al. |
| 2014/0277181 A1 | 9/2014 | Garlock |
| 2014/0277186 A1 | 9/2014 | Granberry et al. |
| 2014/0277214 A1 | 9/2014 | Helenbolt et al. |
| 2014/0277448 A1 | 9/2014 | Guerra et al. |
| 2014/0288657 A1 | 9/2014 | Lederman et al. |
| 2014/0309689 A1 | 10/2014 | Sikora et al. |
| 2014/0324167 A1 | 10/2014 | Schmieding et al. |
| 2014/0335145 A1 | 11/2014 | Jin et al. |
| 2014/0350688 A1 | 11/2014 | Michel et al. |
| 2015/0073424 A1 | 3/2015 | Couture et al. |
| 2015/0134066 A1 | 5/2015 | Bachmaier |
| 2015/0142052 A1 | 5/2015 | Koogle, Jr. et al. |
| 2015/0201951 A1 | 7/2015 | Bradley et al. |

(56) References Cited

U.S. PATENT DOCUMENTS

| | | |
|---|---|---|
| 2015/0216541 A1 | 8/2015 | Schmieding et al. |
| 2015/0245831 A1 | 9/2015 | Sullivan |
| 2015/0250472 A1 | 9/2015 | Ek et al. |
| 2015/0250475 A1 | 9/2015 | Ek |
| 2015/0250594 A1 | 9/2015 | Ek |
| 2015/0250602 A1 | 9/2015 | Sikora et al. |
| 2015/0313586 A1 | 11/2015 | Burkhart et al. |
| 2016/0030035 A1 | 2/2016 | Zajac et al. |
| 2016/0051268 A1 | 2/2016 | Seitlinger et al. |
| 2016/0106444 A1 | 4/2016 | Ek |
| 2016/0151060 A1 | 6/2016 | Albertorio et al. |
| 2016/0151119 A1 | 6/2016 | Michel et al. |

FOREIGN PATENT DOCUMENTS

| | | |
|---|---|---|
| AU | 2002248198 B2 | 5/2007 |
| AU | 2005202099 B2 | 6/2007 |
| AU | 2002357284 B2 | 8/2007 |
| AU | 2006202337 B2 | 5/2008 |
| AU | 2003262428 | 8/2009 |
| AU | 2007216648 B2 | 11/2009 |
| AU | 2004216106 B2 | 6/2010 |
| AU | 2008207536 B2 | 3/2011 |
| CA | 2470194 C | 2/2011 |
| DE | 2933174 | 4/1980 |
| DE | 3516743 | 11/1986 |
| DE | 3840466 | 6/1990 |
| DE | 19505083 | 11/1995 |
| DE | 102004053606 | 5/2006 |
| DE | 112013003358 | 3/2015 |
| EP | 0240004 | 10/1987 |
| EP | 0241240 | 10/1987 |
| EP | 0290736 | 11/1988 |
| EP | 0350780 | 1/1990 |
| EP | 0485678 | 5/1992 |
| EP | 0327387 | 9/1992 |
| EP | 0505634 | 9/1992 |
| EP | 0736292 | 10/1996 |
| EP | 0903125 | 3/1999 |
| EP | 0903127 | 3/1999 |
| EP | 0993812 | 4/2000 |
| EP | 0661023 | 8/2001 |
| EP | 1374782 | 1/2004 |
| EP | 1426013 | 9/2004 |
| EP | 1870060 | 12/2007 |
| EP | 1927328 | 6/2008 |
| EP | 1278460 | 4/2009 |
| EP | 2062541 | 5/2009 |
| EP | 2314257 | 2/2013 |
| EP | 2804565 | 10/2014 |
| EP | 2481368 | 12/2014 |
| EP | 2986232 | 2/2016 |
| FR | 2242068 | 3/1975 |
| FR | 2642301 | 3/1990 |
| FR | 2676917 | 12/1992 |
| FR | 2693650 | 1/1994 |
| FR | 2718014 | 10/1995 |
| FR | 2733904 | 11/1996 |
| FR | 2739151 | 3/1997 |
| GB | 2281577 | 3/1995 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2964035 | 10/1999 |
| JP | 2001525210 | 12/2001 |
| JP | 2002291779 | 10/2002 |
| JP | 2003534096 | 11/2003 |
| WO | 8803781 | 6/1988 |
| WO | 8909578 | 10/1989 |
| WO | 9409730 | 5/1994 |
| WO | 9427507 | 12/1994 |
| WO | 9624304 | 8/1996 |
| WO | 9722306 | 6/1997 |
| WO | 9920192 | 4/1999 |
| WO | 0013597 | 3/2000 |
| WO | 0105336 | 1/2001 |
| WO | 0166021 | 9/2001 |
| WO | 0166022 | 9/2001 |
| WO | 0182677 | 11/2001 |
| WO | 0191648 | 12/2001 |
| WO | 0191672 | 12/2001 |
| WO | 0217821 | 3/2002 |
| WO | 02086180 | 10/2002 |
| WO | 03047470 | 6/2003 |
| WO | 03051210 | 6/2003 |
| WO | 03051211 | 6/2003 |
| WO | 03061516 | 7/2003 |
| WO | 03065909 | 8/2003 |
| WO | 2004014261 | 2/2004 |
| WO | 2004026170 | 4/2004 |
| WO | 2004052216 | 6/2004 |
| WO | 2004075777 | 9/2004 |
| WO | 2004100839 | 11/2004 |
| WO | 2005051231 | 6/2005 |
| WO | 2006004885 | 1/2006 |
| WO | 2006074321 | 7/2006 |
| WO | 2006091686 | 8/2006 |
| WO | 2010135156 | 11/2010 |
| WO | 2013152102 | 10/2013 |
| WO | 2014008126 | 1/2014 |
| WO | 2014172347 | 10/2014 |

OTHER PUBLICATIONS

U.S. Examiner interview summary dated Apr. 8, 2015, issued in U.S. Appl. No. 12/001,473, 4 pages.
U.S. Final Office Action dated Apr. 16, 2015, issued in U.S. Appl. No. 12/762,920, 15 pages.
U.S. Supplemental Notice of Allowance dated Apr. 21, 2015, issued in U.S. Appl. No. 13/436,188, 6 pages.
U.S. Final Office Action dated Apr. 28, 2015, issued in U.S. Appl. No. 13/785,867, 8 pages.
U.S. Office Action dated May 1, 2015, issued in U.S. Appl. No. 14/133,943, 25 pages.
U.S. Final Office Action dated May 22, 2015, issued in U.S. Appl. No. 13/438,095, 7 pages.
U.S. Final Office Action dated Jun. 2, 2015, issued in U.S. Appl. No. 12/001,473, 18 pages.
U.S. Office Action dated Apr. 29, 2014, issued in U.S. Appl. No. 13/037,929, 11 pages.
U.S. Office Action dated May 19, 2014, issued in U.S. Appl. No. 13/436,188, 10 pages.
U.S. Office Action dated May 28 2014, issued in U.S. Appl. No. 13/752,858, 8 pages.
U.S. Office Action dated Jun. 4, 2014, issued in U.S. Appl. No. 12/762,920, 10 pages.
Notice of Allowance dated Jun. 19, 2014, issued in U.S. Appl. No. 13/470,678, 5 pages.
Intent to Grant dated Jun. 27, 2014, issued in European Patent Application No. 12 002 103.5, 6 pages.
U.S. Office Action dated Jul. 7, 2014, issued in U.S. Appl. No. 12/979,992, 6 pages.
U.S. Office Action dated Jul. 7, 2014, issued in U.S. Appl. No. 12/001,473, 15 pages.
USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.

(56) References Cited

OTHER PUBLICATIONS

USPTO Notice of Allowance issued Sep. 26, 2003 in U.S. Appl. No. 10/162,533.
USPTO Notice of Allowance issued May 12, 2003 in U.S. Appl. No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patnet application No. 2005202099.
AU Examiners report dated Jan. 12, 2007 issued in corresponding Australian patnet application No. 2006202337.
AU Examiners report dated Feb. 21, 2007 issued in corresponding Australian patnet application No. 2005202099.
AU Examiners report dated May 23, 2007 issued in corresponding Australian patnet application No. 2005202099.
AU Notice of Acceptance dated Aug. 6, 2007 in Patent Application No. 20022357284.
EPO supplementary partial search report dated May 10, 2004 issued in corresponding European application 01932833.5-231-/U.S. Pat. No. 0114061.
EPO supplementary search report dated Aug. 30, 2004 issued in corresponding European application 01932833.5.
EPO Office Action dated Aug. 23, 2004, received in related EPO application No. 03 026 286.9 (4 pgs).
EPO Office Action dated Mar. 15, 2005, received in related EPO application No. 03 026 286.9, (3 pgs).
EPO Search Report received in related EPO Application No. 03 02 6286.9 dated Feb. 26, 2004 (5pgs).
EPO Search Report received in related EPO Application No. 03 02 6286.9 dated Apr. 27, 2004 (6pgs).
Examination Report dated Feb. 22, 2005 received in corresponding European Application No. 01932833.5 (3pages).
EPO Office Action dated Sep. 22, 2005 issued in corresponding European application 01932833.5-2310.
EPO Office Action dated Sep. 11, 2006 issued in corresponding European application 01932833.5-2310.
International Preliminary Examination Report dated Nov. 5, 2002 issued in corresponding PCT patent application No. PCT/US01/14061.
US Office Action issued in related U.S. Appl. No. 10/994,453 dated Feb. 25, 2008.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
International Preliminary Examination Report dated Aug. 19, 2004 issued in corresponding PCT patent application No. PCT/US02/40310.
Notice of Allowance issued in corresponding U.S. Appl. No. 10/618,887 dated Sep. 13, 2007.
International Preliminary Report on Patentability and Written Opinion dated May 22, 2006 in corresponding PCT patent application No. PCT/US04/039181.
English language translation of Japanese Office Action dated Aug. 9, 2007 issued in corresponding Japanese application No. 2003-552148.
Canadian Office Action dated Jan. 2, 2008 issued in corresponding Canadian Application No. 2407440.
International Preliminary Report on Patentability and Written Opinion dated Mar. 1, 2007 in corresponding PCT patent application No. PCT/US05/030120.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report dated Dec. 27, 2001 issued in corresponding PCT patent application No. PCT/US01/14061.
Office Action issued in corresponding U.S. Appl. No. 10/741,044 dated Oct. 26, 2005.
International Search Report dated May 23, 2003 issued in corresponding PCT patent application No. PCT/US02/40310.
International Search Report and Written Opinion dated Dec. 30, 2004 issued in corresponding PCT patent application No. PCT/US04/05539.
International Search Report and Written Opinion dated Jan. 30, 2006 issued in corresponding PCT patent application No. PCT/US04/39181.
International Search Report and Written Opinion dated Aug. 30, 2006 issued in corresponding PCT patent application No. PCT/US06/06323.
International Search Report and Written Opinion dated Sep. 29, 2006 issued in corresponding PCT patent application No. PCT/US05/30120.
International Search Report and Written Opinion dated Nov. 27, 2006 issued in corresponding PCT patent application No. PCT/US06/00380.
International Search Report and Written Opinion dated Nov. 29, 2006 issued in corresponding PCT patent application No. PCT/US05/023200.
International Search Report and Written Opinion dated May 22, 2007 issued in corresponding PCT patent application No. PCT/US05/05980.
International Preliminary Report on Patentability dated Sep. 1, 2011 issued in PCT International Patent Application No. PCT/US2010/025095, 8 pages.
International Preliminary Report on Patentability dated Oct. 27, 2011 issued in PCT International Patent Application No. PCT/US2010/031602, 8 pages.
International Preliminary Report on Patentability dated Oct. 27, 2011 issued in PCT International Patent Application No. PCT/US2010/031594, 7 pages.
U.S. Office Action dated Nov. 1, 2011 issued in U.S. Appl. No. 12/713,135, 10 pages.
U.S. Notice of Allowance dated Nov. 23, 2011 issued in U.S. Appl. No. 11/623,513, 19 pages.
U.S. Office Action dated Nov. 28, 2011 issued in U.S. Appl. No. 12/711,039, 6 pages.
Notice of Allowance dated Dec. 12, 2011 issued in U.S. Appl. No. 12/582,345, 19 pages.
U.S. Office Action dated Dec. 22, 2011 issued in U.S. Appl. No. 11/623,513, 8 pages.
U.S. Office Action dated Dec. 27, 2011 issued in U.S. Appl. No. 12/620,309, 10 pages.
U.S. Office Action dated Jan. 4, 2012 issued in U.S. Appl. No. 12/001,473, 19 pages.
U.S. Office Action dated Jan. 10, 2012 issued in U.S. Appl. No. 12/031,534, 9 pages.
U.S. Office Action dated Jan. 18, 2012 issued in U.S. Appl. No. 12/778,055, 9 pages.
European Office Action dated Jan. 23, 2012 issued in European Patent Application No. 01 997 077.1, 3 pages.
Examination Report dated Dec. 30, 2011 issued in European Patent Application No. 09 002 088.4, 6 pages.

(56) References Cited

OTHER PUBLICATIONS

Intent to Grant dated Feb. 17, 2012 issued in European Patent Application No. 02 805 182.9, 5 pages.
Notice of Allowance dated Feb. 24, 2012 issued in U.S. Appl. No. 12/027,121, 9 pages.
Intent to Grant dated Feb. 29, 2012 issued in European Patent Application No. 10 012 693.7, 5 pages.
Supplemental Notice of Allowance dated Mar. 2, 2012 issued in U.S. Appl. No. 12/027,121, 2 pages.
Office Action dated Mar. 2, 2012 issued in U.S. Appl. No. 12/713,135, 7 pages.
U.S. Office Action dated Mar. 29, 2012 issued in U.S. Appl. No. 10/789,545, 7 pages.
U.S. Office Action dated Apr. 18, 2012 issued in U.S. Appl. No. 12/725,181, 9 pages.
U.S. Notice of Allowance dated May 31, 2012 issued in U.S. Appl. No. 11/623,513, 5 pages.
Extended Search Report dated Jul. 3, 2012 issued in European Patent Application No. 12002103.5, 5 pages.
Decision to Grant dated Jul. 26, 2012 issued in European Patent Application No. 10012693.7, 1 page.
Final Office Action dated Aug. 13, 2012 issued in U.S. Appl. No. 12/711,039, 12 pages.
Office Action dated Aug. 14, 2012 issued in U.S. Appl. No. 12/001,473, 17 pages.
Office Action dated Aug. 20, 2012 issued in U.S. Appl. No. 13/037,998, 11 pages.
Office Action dated Aug. 21, 2012 issued in U.S. Appl. No. 13/043,430, 11 pages.
U.S. Office Action dated Aug. 28, 2012 issued in U.S. Appl. No. 12/762,948, 12 pages.
U.S. Notice of Allowance dated Sep. 4, 2012 issued in U.S. Appl. No. 11/169,326, 6 pages.
Notice of Allowability dated Oct. 9, 2012, issued in U.S. Appl. No. 12/713,135, 5 pages.
Notice of Allowability dated Oct. 11, 2012, issued in U.S. Appl. No. 11/169,326 2 pages.
U.S. Office Action dated Oct. 23, 2012 issued in U.S. Appl. No. 13/042,382, 17 pages.
U.S. Office Action dated Oct. 24, 2012 issued in U.S. Appl. No. 12/942,923, 9 pages.
U.S. Office Action dated Oct. 31, 2012 issued in U.S. Appl. No. 13/075,006, 9 pages.
Notice of Allowance dated Nov. 13, 2012 issued in U.S. Appl. No. 12/725,181, 5 pages.
Preliminary Report on Patentability dated Sep. 20, 2012 issued in PCT Patent Application No. PCT/US2011/027451, 3 pages.
Extended European Search report mailed Dec. 10, 2012 issued in European Patent Application No. 07844549.1, 6 pages.
Supplementary European Search Report dated Jan. 3, 2013 issued in European Patent Application No. 05763817.3, 3 pages.
Great Britain Examination Report dated Feb. 6, 2013 issued in Great Britain Patent Application No. 1114417.7, 2 pages.
Supplementary European Search Report dated Feb. 18, 2013 issued in European Patent Application No. 08729178.7, 10 pages.
U.S. Office Action dated Feb. 25, 2013 issued in U.S. Appl. No. 12/762,920, 8 pages.
Canadian Office Action dated Dec. 13, 2012 issued in Canadian Patent Application No. 2,407,440, 6 pages.
International Search Repoort and Written Opinion dated Mar. 8, 2013 issued in PCT Patent Application No. PCT/US12/71199, 13 pages.
U.S. Office Action dated Apr. 15, 2013 issued in U.S. Appl. No. 13/470,678, 10 pages.
U.S. Office Action dated Apr. 22, 2013 issued in U.S. Appl. No. 12/001,473, 16 pages.
U.S. Office Action dated Apr. 23, 2013 issued in U.S. Appl. No. 13/037,998, 8 pages.
European Intent to Grant dated Apr. 29, 2013 issued in European Patent Application No. 07 862 736.1, 7 pages.
U.S. Notice of Allowance dated May 9, 2013 issued in U.S. Appl. No. 12/725,181, 6 pages.
U.S. Office Action dated May 15, 2013 issued in U.S. Appl. No. 12/762,948, 10 pages.
U.S. Office Action dated Jul. 11, 2013 issued in U.S. Appl. No. 12/711,039, 10 pages.
U.S. Notice of Allowance dated Jul. 29, 2013 issued in U.S. Appl. No. 12/725,181, 7 pages.
U.S. Final Office Action dated Jul. 30, 2013 issued in U.S. Appl. No. 13/075,006, 10 pages.
U.S. Corrected Notice of Allowance dated Jul. 30, 2013 issued in U.S. Appl. No. 11/623,513, 2 pages.
Corrected Notice of Allowability dated Sep. 10, 2013 issued in U.S. Appl. No. 13/043,430, 7 pages.
Decision to Grant dated Sep. 19, 2013 issued in European Patent Application No. 07862736.1, 1 page.
U.S. Office Action dated Jun. 25, 2015, issued in U.S. Appl. No. 12/711,039, 10 pages.
U.S. Final Office Action dated Jul. 7, 2015, issued in U.S. Appl. No. 12/762,948, 15 pages.
Intent to Grant dated Jul. 8, 2015, issued in European Patent Application No. 08 729 178.7, 7 pages.
Notice of Allowance dated Jul. 31, 2015, issued in U.S. Appl. No. 13/438,095, 8 pages.
Extended Search Report dated Sep. 9, 2015, issued in European Patent Application No. 11751521.3, 13 pages.
U.S. Final Office Action dated Sep. 17, 2015, issued in U.S. Appl. No. 14/035,061, 10 pages.
Habermeyer, Peter, ATOS News, Oct. 2005, "The Artificial Limb "Eclipse"—A new draft without shank in the implantation of artificial shoulder limbs", cover page w/pp. 40-41, with English translation dated Jan. 13, 2006 (2 pgs).
Thermann, et al, ATOS Newsletter, Jun. 2005, Aktuelle Therrien, (16 pages).
Gray, Henry, Anatomy of the Human Body, 1918, 6d. The Foot 1. The Tarsus, II. Osteology, cover page and 10 pgs, www.Bartleby.com/107/63.html#i268 Oct. 25, 2004.
Chainsaw, Wikipedia, the free encyclopedia, http://en.wikipedia.org/w/index.php?title=Chainsaw&printable=yes, Jun. 26, 2007 (3 pages).
Cannulated Hemi Implants from Vielex, (3 pages).
APTA | Knee,/http://www.apta.org/AM/PrinerTemplate.cfm?Section=Home&TEMPLATE=/CM/HTMLDisplay.dfg& . . . Jun. 25, 2007 (1page).
Arthrosurface, Restoring the Geometry of Motion, HemiCAP Patello—Femoral Resurfacing System (19 pages).
Anatomical Arthroplastie, Total Evolutive Shoulder System T.E.S.S., Biomet France, Biomet Europe (4 pages).
American Machinist, Full-radius milling cutters, http://www.americanmachinist.com/Classes/Article/ArticleDraw_P.aspx, Jun. 26, 2007 (1 page).
Chuck (engineering),Wikipedia, the free encyclopedia, http://en.wikipedia.org/w/index.php?title=Chuck_%28engineering%29&printable=yes, Jun. 25, 2007, (4 pages).
Dovetail Rails, http://www.siskiyou.com/MDRSeries.htm, Jun. 25, 2007 (2 pages).
Knee Resurfacing, Permedica, GKS, Global Knee System. Cod. 104570 vers 1.0 del Mar. 15, 2006 (8pages).
Major Biojoint System, La nuova frontiera della biointegrazione naturale, Finceramica Biomedical solutions (4 pages).
Makita Industrial Power Tools, Product Details Print Out, Chain Mortiser, http://www.makita.com/menu.php?pg=product_det_prn&tag=7104L, Jun. 26, 2007 (3pgs).
Milling machine, Wikipedia, the free encyclopedia, http://en.wikipedia.org/w/index.php?title=Milling_machine&printable=yes, Jun. 26, 2007 (4 pages).
Mortise and tenon, Wikipedia, the free encyclopedia, http://en.wikipedia.org/w/index.php?title=Mortise_and_tenon&printable=yes, Jun. 25, 2007 (3 pages).
Oka et al, "Development of artificial articular cartilage", Proc Instn Mech Engrs vol. 214 Part H, 2000 pp. 59-68 (10 pages).
Reversed Arthroplastie, Total Evolutive Shoulder System T.E.S.S., Biomet France, Biomet Europe (4 pages).

(56) References Cited

OTHER PUBLICATIONS

M. Siguier, MD et al, "Preliminary Results of Partial Surface Replacement of the Femoral Head in Osteonecrosis", The Jorunal of Arthroplasty, vol. 14, No. 1, 1999, pp. 45-51.
T. Siguier, MD et al, Partial Resurfacing Arthroplasty of the Femoral Head in Avascular Necrosis, Clinical Orthopaedics and Related Research, No. 386, 2001, pp. 85-92.
Suganuma, et al—"Arthroscopically Assisted Treatment of Tibial Plateau Fractures", Arthroscopy: The Journal of Arthroscopic and Related Surgery, vol. 20, No. 10, Dec. 2004, pp. 1084-1089 (6 pages).
The Mini Uni: A New Solution for Arthritic Knee Pain and Disability, AORI, 4 pages, www.aori.org/uniknee.htm Apr. 20, 2004.
The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.
Ushio et al, "Partial hemiarthroplasty for the treatment of osteonecrosis of the femoral head", An Experimantal Study in the Dog, The Journal of Bone and Joint Surgery, vol. 85-B, No. 6, Aug. 2003, pp. 922-930 (9 pages).
Russell E. Windsor, MD, In-Depth Topic Reviews, Unicompartmental Knee Replacement, Nov. 7, 2002, 9 pages.
Yaw angle, Wikipedia, the free encyclopedia, http://en.wikipedia.org/w/index.php?title=Yaw_angle&printable=yes, Jun. 25, 2007 (1 page).
Bale, MD, Reto J., et al, "Osteochondral Lesions of the Talus: Computer=assisted Retrograde Drilling Feasibility and Accuracy in Initial Experriences", (Radiology. 2001;218:278-282) © RSNA, 2001.
Biomet/Copeland, "Aequalis® Resurfacing Head" Tornier, Scientific Vision, Surgical Leadership, SS-401 Jan. 2007.
Kumai, M.D., Tsukasa, et al Arthroscopic Drilling for the Treatment of Osteochondral Lesions of the Talus, The Journal of Bone & Joint Surgery, American vol. 81:1229-35(1999).
Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 Jul.-Aug. 2001:pp. 653-659.
Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.
Schneider, T., et al, "Arthroscopy of the ankle joint. A list of indications and realistic expectations", Foot and Ankle Surgery 1996 2:189-193, © 1996 Arnette Blackwell SA.
Taranow WS, et al, "Retrograde drilling of osteochondral lesions of the medial talar dome", PubMed, www.pubmed.gov, A service of the National Library of Medicing and the Natinal Institutes of Health, Foot Ankle Int. Aug. 1999; 20 (8):474-80.
Ueblacker, M.D., Peter, et al, "Retrograde Cartilage Transplantation of the Proximal and Distal Tibia", Arthroscopy: The Journal of Arthroscipic and Related Surgery, vol. 20, No. 1 Jan. 2004: pp. 73-78.
USPTO Office Action dated Dec. 21, 2007 issued in corresponding U.S. Appl. No. 11/169,326.
USPTO Office Action dated Dec. 26, 2007 issued in U.S. Appl. No. 11/379,151.
USPTO Office Action dated Oct. 9, 2007 issued in U.S. Appl. No. 10/373,463.
USPTO Office Action dated Aug. 29, 2007 issued in U.S. Appl. No. 10/760,965.
USPTO Office Action dated May 31, 2007 issued in corresponding U.S. Appl. No. 11/326,133.
USPTO Office Action dated Apr. 26, 2007 issued in U.S. Appl. No. 10/373,463.
USPTO Office Action dated Apr. 4, 2007 issued in corresponding U.S. Appl. No. 10/789,545.
USPTO Office Action dated Mar. 15, 2007 issued in U.S. Appl. No. 10/760,965.
USPTO Office Action dated Feb. 20, 2007 issued in corresponding U.S. Appl. No. 11/326,133.
USPTO Office Action dated Nov. 6, 2006 issued in U.S. Appl. No. 10/760,965.
USPTO Office Action dated Oct. 17, 2006 issued in U.S. Appl. No. 10/373,463.
USPTO Office Action dated Oct. 31, 2006 issued in U.S. Appl. No. 10/760,965.
USPTO Office Action dated Jul. 25, 2006 issued in U.S. Appl. No. 10/760,965.
USPTO Office action dated May 10, 2006 issued in corresponding U.S. Appl. No. 10/373,463.
USPTO Office Action dated Apr. 21, 2006 issued in corresponding U.S. Appl. No. 10/308,718.
USPTO Office Action dated Nov. 9, 2005 issued in corresponding U.S. Appl. No. 10/308,718.
International Search Report and Written Opinion dated Aug. 8, 2007 issued in corresponding PCT patent application No. PCT/US06/29875.
Notice of Allowance issued in corresponding U.S. Appl. No. 10/308,718 dated Sep. 11, 2006.
Office Action issued in corresponding U.S. Appl. No. 11/326,133 dated Oct. 17, 2007.
United States Office Action issued is related U.S. Appl. No. 10/760,965 dated Feb. 19, 2008.
Australian Office Action issued in related Australian Patent Application No. 2003262428 dated Mar. 20, 2008.
Australian Office Action issued in related Australian Patent Application No. 2004293042 dated Feb. 20, 2008.
U.S. Office Action issued in related U.S. Appl. No. 11/326,133 dated Jun. 12, 2008.
International Search Report and Written Opinion dated Jun. 24, 2008 issued in related International Patent Application No. PCT/US07/73685.
International Search Report and Written Opinion dated Jun. 11, 2008 issued in related International Patent Application No. PCT/US07/25284.
International Search Report and Written Opinion dated Aug. 8, 2008 issued in related International Patent Application No. PCT/US08/53988.
U.S. Office Action issued in related U.S. Appl. No. 10/994,453 dated Jun. 5, 2007.
Japanese Office Action dated Jul. 22, 2008 issued in related Japanese Patent Application No. 2006-501193.
U.S. Office Action issued in related U.S. Appl. No. 10/373,463 dated Apr. 21, 2008.
Notice of Allowance received in U.S. Appl. No. 10/618,887 dated Aug. 15, 2008.
Australia Office Action issued in related Australian Patent Application No. 2007216648 dated May 30, 2008.
European Office Action issued in related European Patent Application No. 01932833.5-2310 dated Apr. 25, 2008.
U.S. Office Action received in related U.S. Appl. No. 11/169,326 dated Jun. 30, 2008.
U.S. Office Action received in related U.S. Appl. No. 11/169,326 dated Jul. 27, 2007.
U.S. Office Action received in related U.S. Appl. No. 11/169,326 dated Apr. 17, 2007.
U.S. Office Action received in related U.S. Appl. No. 11/169,326 dated Mar. 9, 2007.
Canadian Office Action issued in related Canadian Patent Application No. 2546582 dated Aug. 21, 2008.
U.S. Office Action issued in related U.S. Appl. No. 10/994,453 dated Sep. 3, 2008.
U.S. Office Action dated Oct. 21, 2008 issued in related U.S. Appl. No. 11/461,240.
U.S. Office Action dated Jun. 25, 2008 issued in related U.S. Appl. No. 11/359,891.
U.S. Office Action dated Sep. 25, 2008 issued in related U.S. Appl. No. 11/326,133.

(56) References Cited

OTHER PUBLICATIONS

U.S. Office Action dated Jul. 2, 2008 issued in related U.S. Appl. No. 11/379,151.
European Office Action dated Oct. 6, 2008 issued in related European Patent Application No. 01932833.5-2310.
U.S. Office Action dated Jun. 27, 2008 issued in related U.S. Appl. No. 10/760,965.
International Search Report and Written Opinion dated Oct. 1, 2008 issued in related International Patent Application No. PCT/US08/53194.
International Search Report and Written Opinion dated Oct. 9, 2008 issued in related International Patent Application No. PCT/US07/82262.
European Search Report dated Nov. 4, 2008 issued in related European Patent Application No. 04811836.8-2310.
Habermeyer, "Eclipse, Schaftfreie Schulterprothese Operationsanleitung," (dated unknown).
U.S. Office Action dated Jan. 9, 2009 issued in related U.S. Appl. No. 10/373,463.
Canadian Office Action dated Dec. 9, 2008 issued in related Canadian Patent Application No. 2407440.
Supplemental European Search Report dated Nov. 6, 2008 issued in related European Patent Application No. 05791453.3-2310.
Japanese Office Action dated Dec. 19, 2008 issued in Japanese Patent Application No. 2006501193.
Japanese Office Action dated Jan. 13, 2009 issued in Japanese Patent Application No. 2003552147.
International Search Report dated Jan. 30, 2006 issued in related International Patent Application No. PCT/US04/39181.
U.S. Office Action dated Mar. 27, 2009 issued in related U.S. Appl. No. 11/169,326.
European Office Action dated Feb. 26, 2009 in related European Patent Application No. 05791453.3.
McCarty, III., et al., "Nonarthroplasty Treatment of Glenohumeral Cartilage Lesions," Arthroscopy, The Journal of Arthroscopic and related Surgery, vol. 21, No. 9; Sep. 2005 (pp. 1131-1142).
Bushnell, et al., "Bony Instability of the Shoulder," Arthroscopy, The Journal of Arthroscopic and related Surgery, vol. 24, No. 9; Sep. 2005 (pp. 1061-1073).
Scalise, et al., "Resurfacing Arthroplasty of the Humerus: Indications, Surgical Technique, and Clinical Results," Techniques in Shoulder and Elbow Surgery 8(3):152-160; 2007.
Davidson, et al., "Focal Anatomic Patellofemoral Inlay Resurfacing: Theoretic Basis, Surgical Technique, and Case Reports," Orthop. Clin. N. Am., 39 (2008) pp. 337-346.
Provencher, et al., "Patellofemoral Kinematics After Limited Resurfacing of the Trochlea," The Journal of Knee Surgery, vol. 22 No. 2 (2008) pp. 1-7.
Dawson, et al., "The Management of Localized Articular Cartilage Lesions of the Humeral Head in the Athlete," Operative Techniques in Sports Medicine, vol. 16, Issue 1, pp. 14-20 (2008).
Uribe, et al., "Partial Humeral Head Resurfacing for Osteonecrosis," Journal of Shoulder and Elbow Surgery, (2009) 6 pages.
Burks, "Implant Arthroplasty of the First Metatarsalphalangeal Joint," Clin. Podiatr. Med. Surg., 23 (2006) pp. 725-731.
Hasselman, et al., "Resurfacing of the First Metatarsal Head in the Treatment of Hallux Rigidus," Techniques in Foot & Ankle Surgery 7(1):31-40, 2008.
Jäger, et al., "Partial hemi-resurfacing of the hip joint—a new approach to treat local osteochondral defects?" Biomed Tech 2006; 51:371-376 (2006).
U.S. Office Action dated May 18, 2010 issued in related U.S. Appl. No. 12/415,503.
Japanese Notice of Reasons for Rejection dated Jun. 1, 2010 issued in related Japanese Patent Application No. 2003394702.
European Office Action dated Jun. 1, 2010 issued in related European Patent Application No. 04811836.8-2310.
Japanese Notice of Reasons for Rejection dated Jun. 29, 2010 issued in related Japanese Patent Application No. 2007519417.
Australian Office Action dated Jun. 11, 2010 issued in related Australian Patent Application No. 2005277078.
International Search Report dated Jun. 9, 2010 issued in related International Patent Application No. PCT/US2010/031594.
European Office Action dated May 7, 2010 issued in related European Patent Application No. 06733631.3-2310.
International Search Report dated Jun. 18, 2010 issued in related International Patent Application No. PCT/US2010/031602.
U.S. Office Action dated Jun. 8, 2010 issued in related U.S. Appl. No. 11/209,170.
Office Action dated Sep. 2, 2010 issued in related U.S. Appl. No. 12/415,503.
Office Action dated Aug. 30, 2010 issued in related U.S. Appl. No. 12/397,095.
Office Action dated Jul. 21, 2010 issued in related U.S. Appl. No. 11/551,912.
Office Action dated Aug. 5, 2010 issued in related U.S. Appl. No. 11/325,133.
Notice of Allowance dated Aug. 6, 2010 issued in related U.S. Appl. No. 11/359,892.
Canadian Office Action dated Jul. 29, 2010 issued in related Canadian Patent Application No. 2470936.
Supplemental European Search Report dated Aug. 9, 2010 issued in related European Patent Application No. 04714211.2-2300.
Australian Office Action dated Aug. 23, 2010 issued in related Australian Patent Application No. 2006203909.
Notice of Allowance dated Sep. 9, 2010 issued in related U.S. Appl. No. 10/994,453.
Office Action dated Sep. 21, 2010 issued in related U.S. Appl. No. 11/169,326.
Office Action dated Sep. 29, 2010 issued in related U.S. Appl. No. 11/461,240.
Office Action dated Oct. 11, 2010 issued in related Australian Patent Application No. 2006216725.
International Preliminary Report on Patentability dated Sep. 16, 2010 issued in related International Patent Application No. PCT/US2009/035889.
Supplemental Notice of Allowance dated Oct. 13, 2010 issued in related U.S. Appl. No. 10/994,453.
Supplemental Notice of Allowance dated Oct. 6, 2010 issued in related U.S. Appl. No. 12/415,503.
U.S. Office Action dated Oct. 15, 2010 received in related U.S. Appl. No. 12/027,121.
U.S. Supplemental Notice of Allowance dated Oct. 28, 2010 issued in related U.S. Appl. No. 12/415,503.
European Search Report dated Nov. 4, 2010 issued in related European Patent Application No. 07862736.1-1269.
Notice of Allowance dated Nov. 26, 2010 issued in related U.S. Appl. No. 11/209,170.
Supplemental Notice of Allowance dated Dec. 8, 2010 issued in related U.S. Appl. No. 11/209,170.
Notice of Allowance dated Dec. 13, 2010 issued in related U.S. Appl. No. 12/397,095.
Notice of Allowance dated Jan. 5, 2011 issued in related U.S. Appl. No. 11/326,133.
Supplemental Notice of Allowance dated Feb. 14, 2011 issued in related U.S. Appl. No. 11/326,133.
Canadian Office Action dated Jan. 7, 2011 issued in related Canadian Patent Application No. 2407440.
European Office Action dated Dec. 23, 2010 issued in related European Patent Application No. 028051882.9-2310.
European Office Action dated Dec. 30, 2010 issued in related European Patent Application No. 01997077.1-2310.
Extended Search Report dated Feb. 22, 2011 issued in European Patent Application No. 10012693.7, 8 pages.
Notice of Allowance dated Mar. 2, 2011 issued in Australian Patent Application No. 2008207536, 3 pages.
Notice of Allowance dated Mar. 15, 2011 issued in U.S. Appl. No. 11/551,912, 7pages.
U.S. Office Action dated Apr. 11, 2011 issued in U.S. Appl. No. 11/779,044, 10 pages.
Notice of Allowance dated Apr. 28, 2011 issued in U.S. Appl. No. 12/027,121, 9 pages.

(56) References Cited

OTHER PUBLICATIONS

U.S. Office Action dated May 11, 2011 issued in U.S. Appl. No. 11/623,513, 12 pages.
U.S. Office Action dated May 11, 2011 issued in U.S. Appl. No. 12/001,473, 18 pages.
U.S. Office Action dated May 16, 2011 issued in U.S. Appl. No. 12/582,345, 9 pages.
International Search Report and Written Opinion dated May 19, 2011 issued in PCT Application No. PCT/US2011/027451, 11 pages.
Canadian Notice of Allowance dated Jun. 1, 2011 issued in Canadian Patent Application No. 2,470,936, 1 page.
Examiner interview summary dated Jul. 1, 2011 issued in European Patent Application No. 02 805 182.9, 3 pages.
U.S. Final Office Action dated Jul. 8, 2011 issued in U.S. Appl. No. 11/169,326, 26 pages.
Ascension Orthopedics, Inc., Ascension Orthopedics Announces Market Release of TITAN™ Inset Mini Glenoid, PR Newswire, downloaded from internet Jul. 18, 2011, http://www.orthospinenews.com/ascension-orthopedics-announces-market-release-of-titan™-inset-mini-glenoid, Jul. 6, 2011, 2 pages.
PCT International Preliminary Report on Patentability dated Sep. 9, 2011 issued in PCT Patent Application No. PCT/US2010/025464, 7 pages.
U.S. Office Action dated Oct. 8, 2013 issued in U.S. Appl. No. 13/438,095, 8 pages.
International Search Report and Written Opinion dated Oct. 22, 2013 issued in PCT International Patent Application No. PCT/US2013/048569, 15 pages.
Notice of Allowance dated Oct. 30, 2013 issued in U.S. Appl. No. 13/037,998, 28 pages.
U.S. Final Office Action dated Nov. 29, 2013 issued in U.S. Appl. No. 12/762,920, 9 pages.
U.S. Final Office Action dated Dec. 5, 2013 issued in U.S. Appl. No. 13/470,678, 8 pages.
U.S. Office Action dated Dec. 12, 2013 issued in U.S. Appl. No. 12/979,992, 12 pages.
U.S. Office Action dated Dec. 17, 2013 issued in U.S. Appl. No. 12/001,473, 21 pages.
International Preliminary Report on Patentability dated Jan. 15, 2015, issued in PCT Patent Application No. PCT/US2013/048569, 9 pages.
Notice of Allowance dated Jan. 21, 2015, issued in U.S. Appl. No. 13/752,858, 7 pages.
Notice of Allowability dated Feb. 19, 2015, issued in U.S. Appl. No. 13/037,929, 2 pages.
U.S. Office Action dated Feb. 19, 2015, issued in U.S. Appl. No. 14/035,061, 6 pages.
Notice of Allowance dated Feb. 25, 2015, issued in U.S. Appl. No. 13/436,188, 8 pages.
Office Action dated Mar. 3, 2015, issued in U.S. Appl. No. 12/979,992, 11 pages.
Canadian Office Action dated Feb. 27, 2015 issued in Canadian Patent Application Serial No. 2,407,440, 7 pages.
U.S. Office Action dated Feb. 5, 2014, issued in U.S. Appl. No. 13/438,095, 9 pages.
U.S. Office Action dated Feb. 7, 2014, issued in U.S. Appl. No. 13/075,006, 9 pages.
Australian Examination Report dated Feb. 7, 2014, issued in Australian Patent Application No. 2010236182, 3 pages.
Australian Examination Report dated Feb. 14, 2014, issued in Australian Patent Application No. 2011222404, 3 pages.
European Extended Search Report dated Feb. 24, 2014, issue in European Patent Application No. 09716273.9, 7 pages.
Australian Examination Report dated Feb. 28, 2014, issued in Australian Patent Application No. 2010217907, 3 pages.
U.S. Final Office Action dated Mar. 20, 2014, issued in U.S. Appl. No. 12/711,039, 17 pages.
European Examination Report dated Mar. 20, 2014, issued in European Patent Application No. 12 002 103.5, 3 pages.
U.S. Office Action dated Mar. 21, 2014, issued in U.S. Appl. No. 12/942,923, 6 pages.
U.S. Notice of Allowance dated Apr. 1, 2014, issued in U.S. Appl. No. 13/470,678, 7 pages.
Australian Examination Report dated Apr. 3, 2014, issued in Australian Patent Application No. 2010217907, 3 pages.
U.S. Office Action dated Aug. 13, 2014, issued in U.S. Appl. No. 12/762,948, 12 pages.
U.S. Notice of Allowance dated Aug. 21, 2014, issued in U.S. Appl. No. 13/075,006, 5 pages.
U.S. Office Action dated Sep. 18, 2014, issued in U.S. Appl. No. 13/785,867, 8 pages.
U.S. Notice of Allowance dated Oct. 6, 2014, issued in U.S. Appl. No. 12/942,923, 5 pages.
Sullivan, "HALLUX RIGIDUS: MTP Implant Arthroplasty," Foot Ankle Clin. N. Am. 14 (2009) pp. 33-42.
Cook, et al., "Meta-analysis of First Metatarsophalangeal Joint Implant Arthroplasty," Journal of Foot and Ankle Surgery, vol. 48, Issue 2, pp. 180-190 (2009).
Derner, "Complications and Salvage of Elective Central Metatarsal Osteotomies," Clin. Podiatr. Med. Surg. 26 (2009) 23-35.
Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.
Becher, et al. "Effects of a contoured articular prosthetic device on tibiofemoral peak contact pressure: a biomechanical study," Knee Surg Sports Traumatol Arthrosc. Jan. 2008; 16(1): 56-63.
United States Office Action dated May 13, 2009 issued in related U.S. Appl. No. 11/359,892.
United States Office Action dated May 18, 2009 issued in related U.S. Appl. No. 11/209,170.
United States Office Action dated May 1, 2009 issued in related U.S. Appl. No. 11/461,240.
Australian Office Action dated Jan. 29, 2009 issued in related Australian Patent Application No. 2004216106.
European Search Report dated Apr. 22, 2009 issued in related European Patent Application No. 09002088.4.
U.S. Office Action dated Aug. 30, 2006 issued in related U.S. Appl. No. 10/618,887.
U.S. Office Action dated Jan. 15, 2008 issued in related U.S. Appl. No. 10/618,887.
U.S. Office Action dated May 28, 2009 issued in related U.S. Appl. No. 11/359,891.
International Search Report and Written Opinion dated Jun. 1, 2009 issued in related International Patent Application No. PCT/US2009/035889.
International Preliminary Report and Patentability dated May 7, 2009 issued in related International Patent Application No. PCT/US2007/082262.
Supplemental European Search Report dated May 28, 2009 issued in related International European Patent Application No. 01997077.1.
Supplemental European Search Report dated May 11, 2009 issued in related International European Patent Application No. 02805182.9.
Notice of Allowance dated Feb. 20, 2009 issued in related U.S. Appl. No. 10/618,887.
Notice of Reasons for Rejection issued in related Japanese Patent Application No. 2003-394702 mailed Jul. 21, 2009.
Notice of Reasons for Rejection issued in related Japanese Patent Application No. 20-541615 mailed May 26, 2009.
International Preliminary Report on Patentability issued in related International Patent Application No. PCT/US2007/025284 dated Jun. 25, 2009.
Office Action issued in related Australian Patent Application No. 2007216648 dated Jul. 28, 2009.
European Search Report dated Jul. 10, 2009 issued in related European Patent Application No. 09002088.4.
International Preliminary Report on Patentability dated Aug. 20, 2009 issued in related International Patent Application No. 2008053194.

(56) References Cited

OTHER PUBLICATIONS

Notice of Allowance dated Aug. 25, 2009 issued in related U.S. Appl. No. 11/379,151.
Notice of Allowance dated Aug. 27, 2009 issued in related U.S. Appl. No. 10/760,965.
U.S. Office Action dated Sep. 2, 2009 issued in relation U.S. Appl. No. 10/994,453.
U.S. Office Action dated Oct. 5, 2009 issued in relation U.S. Appl. No. 10/789,545.
U.S. Office Action dated Oct. 15, 2009 issued in relation U.S. Appl. No. 11/551,912.
U.S. Office Action dated Oct. 14, 2009 issued in relation U.S. Appl. No. 11/461,240.
Australian Notice of Allowance dated Oct. 29, 2009 issued in related Australian Patent Application No. 2007216648.
Notice of Allowance dated Oct. 9, 2009 issued in related U.S. Appl. No. 10/373,463.
Australian Office Action dated Oct. 29, 2009 issued in related Australian Patent Application No. 2007203623.
Japanese Notice of Reasons for Rejection dated Sep. 8, 2009 issued in related Japanese Patent Application No. 2003552147.
Notice of Reasons for Rejection dated Nov. 17, 2009 issued in Japanese Patent Application No. 2007-519417.
European Search Report dated Dec. 3, 2009 issued in related European Patent Application No. 06735827.5.
Office Action dated Dec. 24, 2009 issued in related U.S. Appl. No. 10/994,453.
Supplemental Notice of Allowance dated Nov. 25, 2009 issued in related U.S. Appl. No. 10/373,463.
European Office Action dated Jan. 11, 2010 issued in related European Patent Application No. 2005218302.
U.S. Office Action dated Jan. 25, 2010 issued in related U.S. Appl. No. 11/326,133.
Australian Office Action dated Apr. 9, 2010 issued in related Australian Patent Application No. 2005260590.
U.S. Office Action dated Mar. 2, 2010 issued in related U.S. Appl. No. 11/169,326.
U.S. Office Action dated Mar. 9, 2010 issued in related U.S. Appl. No. 11/359,892.
Australian Office Action dated Feb. 26, 2010 issued in related Australian Patent Application No. 2008207536.
Supplemental Notice of Allowance dated Feb. 2, 2010 issued in related U.S. Appl. No. 10/373,463.
European office communication dated Feb. 10, 2010 issued in European Patent Application No. 09002088.4-2310.
International Search Report and Written Opinion dated Apr. 21, 2010 issued in related International Patent Application No. PCT/US2010/025095.
International Search Report and Written Opinion dated May 3, 2010 issued in related International Patent Application No. PCT/US2010/025464.
European Office Action dated Apr. 13, 2010 issued in related European Patent Application No. 02805182.9-2310.
European Office Action dated Mar. 25, 2010 issued in related European Patent Application No. 01997077.1-2310.
U.S. Office Action issued in U.S. Appl. No. 13/438,095, dated Nov. 4, 2014, 11 pages.
International Search Report and Written Opinion issued in PCT Patent Application Serial No. PCT/US14/34157, dated Nov. 4, 2014, 12 pages.
European Extended Search Report issued in European Patent Application Serial No. 10765332.1, dated Nov. 10, 2014, 6 pages.
U.S. Office Action issued in U.S. Appl. No. 12/711,039, dated Nov. 10, 2014, 10 pages.
European Extended Search Report issued in European Patent Application Serial No. 10746863.9, dated Nov. 13, 2014, 5 pages.
European Decision to Grant issued in European Patent Application Serial No. 12002103.5, dated Nov. 20, 2014, 1 page.
European Office Action issued in European Patent Application No. 08 729 178.7, dated Nov. 25, 2014, 4 pages.

U.S. Notice of Allowance issued in U.S. Appl. No. 13/037,929, dated Dec. 11, 2014, 5 pages.
European Office Action dated Apr. 16, 2013 issued in European Patent Application No. 12 002 103.5, 5 pages.
U.S. Applicant Initiated Interview Summary dated May 15, 2013 issued in U.S. Appl. No. 12/762,920, 3 pages.
European Office Action dated May 15, 2013 issued in European Patent Application No. 05 763 817.3, 4 pages.
U.S. Final Office Action dated Jun. 5, 2013 issued in U.S. Appl. No. 12/942,923, 26 pages.
U.S. Final Office Action dated Jun. 24, 2013 issued in U.S. Appl. No. 13/042,382, 28 pages.
U.S. Notice of Allowance dated Jun. 14, 2013 issued in U.S. Appl. No. 13/043,430, 10 pages.
Canadian Office Action dated Feb. 15, 2016, issued in Canadian Patent Application No. 2,407,440, 3 pages.
European Extended Search Report dated Feb. 29, 2016, issued in European Patent Application No. 12860168.9, 11 pages.
Canadian Examiner Requisition dated Mar. 10, 2016, issued in Canadian Patent Application No. 2,759,027, 3 pages.
European Examination Report dated Mar. 21, 2016, issued in European Patent Application No. 10 746 863.9, 3 pages.
U.S. Office Action dated Jan. 21, 2016, issued in U.S. Appl. No. 12/762,948, 14 pages.
U.S. Final Office Action dated Jan. 21, 2016, issued in U.S. Appl. No. 14/133,943, 27 pages.
U.S. Notice of Allowance dated Feb. 8, 2016, issued in U.S. Appl. No. 13/785,867, 8 pages.
U.S. Notice of Allowance dated Feb. 12, 2016, issued in U.S. Appl. No. 12/001,473, 14 pages.
U.S. Office Action dated Mar. 22, 2016, issued in U.S. Appl. No. 14/640,602, 8 pages.
U.S. Notice of Allowability dated Feb. 17, 2016, issued in U.S. Appl. No. 13/785,867, 4 pages.
U.S. Notice of Allowance dated Feb. 17, 2016, issued in U.S. Appl. No. 12/979,992, 5 pages.
U.S. Final Office Action dated Feb. 25, 2016, issued in U.S. Appl. No. 12/711,039, 7 pages.
European Examination Report dated Jul. 22, 2015, issued in European Patent Application No. 09 002 088.4, 4 pages.
International Preliminary Report on Patentability dated Oct. 29, 2015, issued in PCT Patent Application No. PCT/US/2014/034157, 5 pages.
European Examination Report dated Oct. 28, 2015, issued in European Patent Application No. 05 763 817.3, 4 pages.
US Notice of Allowance dated Oct. 30, 2015, issued in U.S. Appl. No. 12/762,920, 8 pages.
Partial Supplementary European Search Report dated Nov. 5, 2015, issued in European Patent Application No. 12860168.9, 6 pages.
US Office Action dated Nov. 17, 2015, issued in U.S. Appl. No. 13/930,737, 9 pages.
US Office Action dated Nov. 25, 2015, issued in U.S. Appl. No. 13/723,902, 13 pages.
European Decision to Grant dated Dec. 17, 2015, issued in European Patent Application No. 08729178.7, 2 pages.
European Examination Report dated Dec. 7, 2015, issued in European Patent Application No. 10 765 332.1, 4 pages.
US Office Action dated Dec. 8, 2015, issued in U.S Appl. No. 13/796,675, 16 pages.
U.S. Office Action dated Jun. 2, 2016, issued in U.S. Appl. No. 14/035,061, 9 pages.
U.S. Notice of Allowance dated Jun. 7, 2016, issued in U.S. Appl. No. 13/930,737, 5 pages.
U.S. Final Office Action dated Jul. 6, 2016, issued in U.S. Appl. No. 13/723,902, 15 pages.
International Search Report and Written Opinion dated, Jun. 10, 2016, issued in PCT Patent Application No. PCT/US2016/023930, 13 pages.

(56) References Cited

OTHER PUBLICATIONS

Official Communication dated Jun. 21, 2016, issued in European Patent Application No. 11 751 521.3, 3 pages.
Official Communication dated Aug. 23, 2016, issued in European Patent Application No. 10 765 332.1, 4 pages.
Final Office Action dated Jul. 19, 2016, issued in U.S. Appl. No. 13/796,675, 17 pages.
Office Action dated Sep. 8, 2016, issued in U.S. Appl. No. 14/640,529, 15 pages.
U.S. Office Action dated Sep. 20, 2016, issued in U.S. Appl. No. 14/133,943, 24 pages.

* cited by examiner

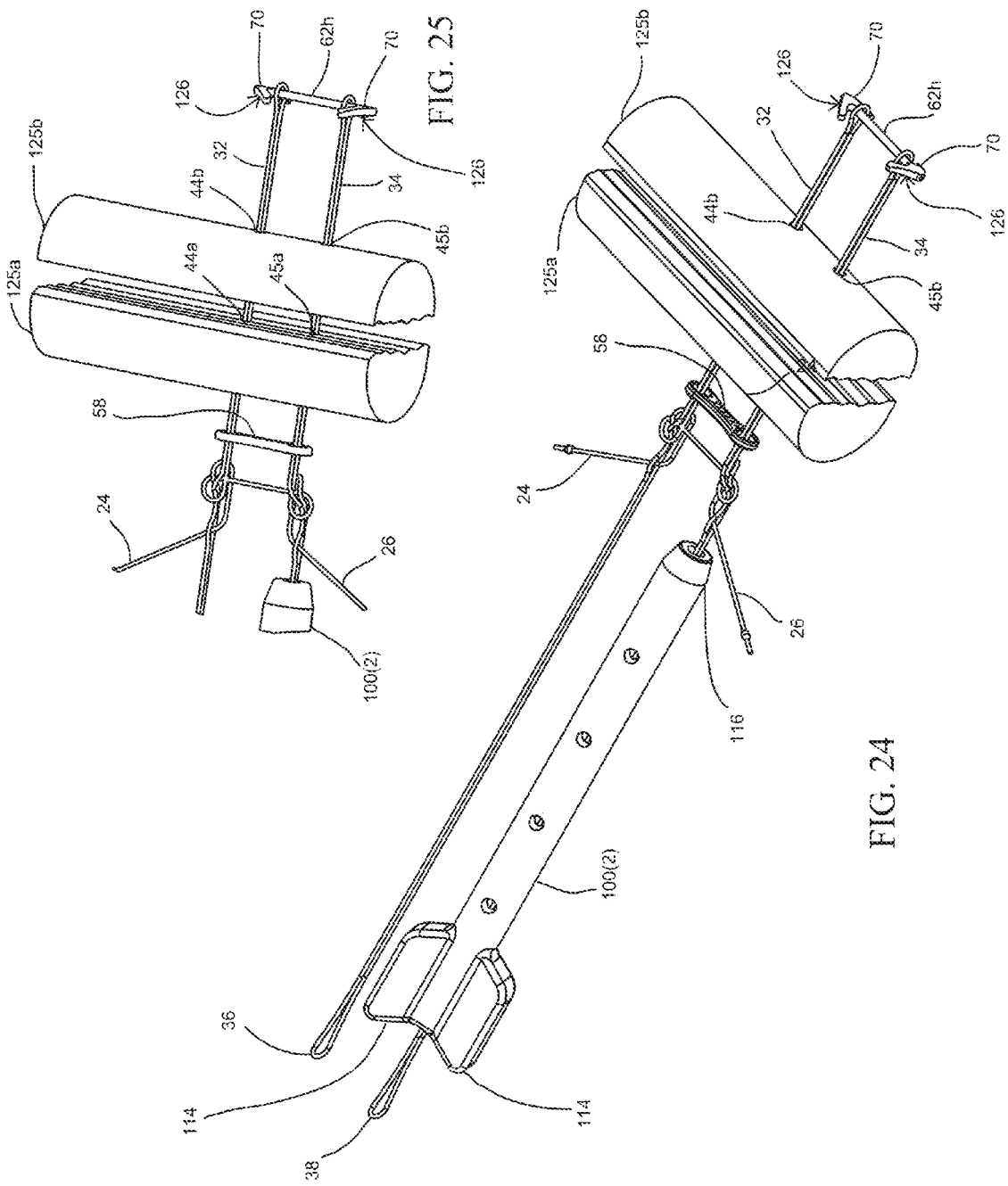

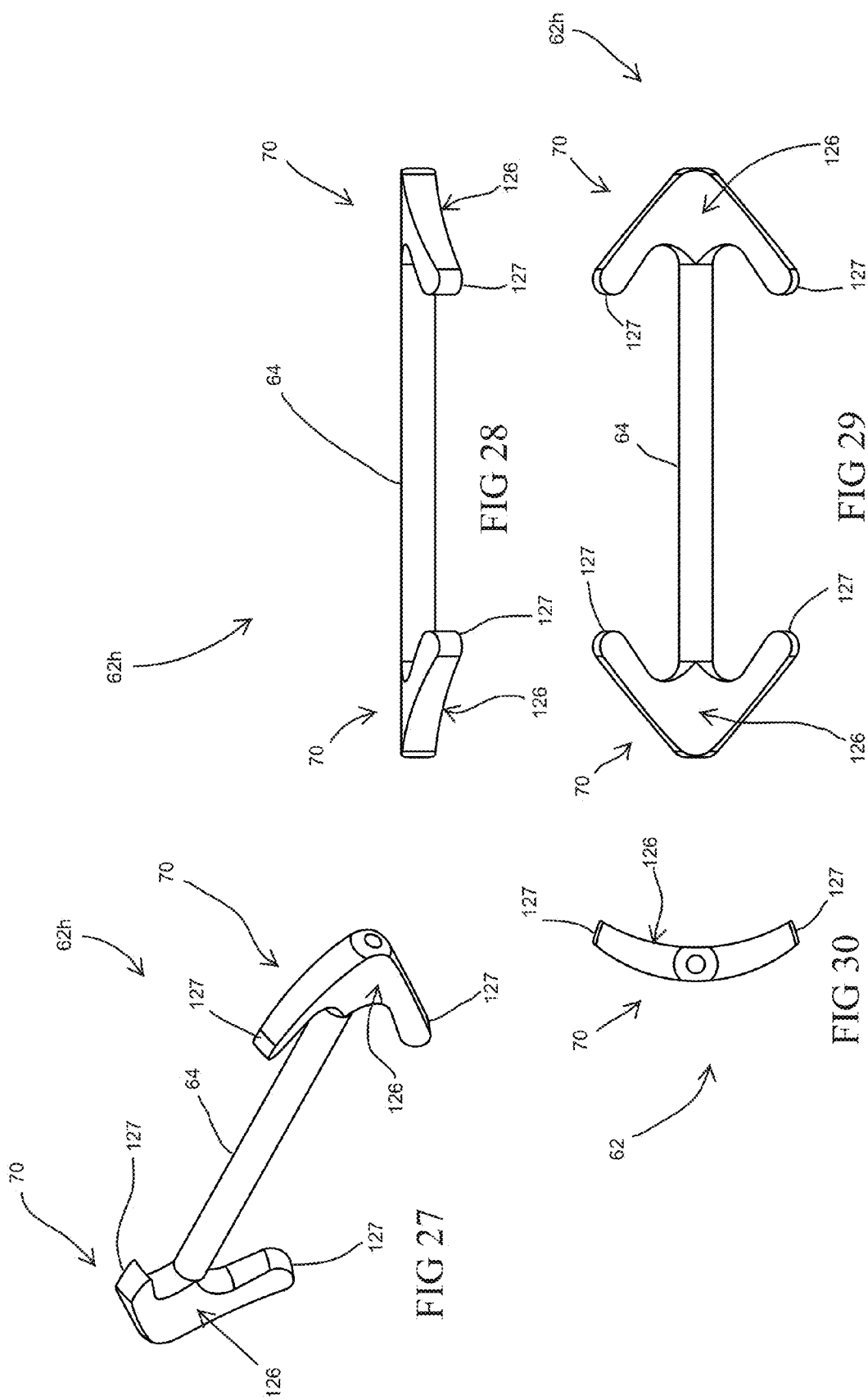

SUTURE SYSTEM AND METHOD

FIELD

This disclosure relates to biological medical devices and methods, and particularly to biological medical suture systems and methods.

BACKGROUND

In many circumstances, it may be desirable to couple two or more bones or tissue segments together. For example, a bunion (hallux valgus) is a common deformity characterized by lateral deviation of the great toe (hallux) on the mesophalangeal joint (where the first metatarsal bone and hallux meet). One method of treating this deformity is to pull the great toe generally into proper alignment using a suture (or the like) disposed around the adjacent, pointer or index toe. In some applications, the two ends of the suture may need to be tied together. Additionally, torn or partially ligaments may be treated by suturing the ligament portions together. Unfortunately, many surgeons are uncomfortable tying knots because of the possibility of the knot becoming loose and/or the difficulty associated with tying a knot during a surgical procedure.

BRIEF DESCRIPTION OF THE DRAWINGS

Features and advantages of the present invention are set forth by description of embodiments consistent with the present invention, which description should be considered in conjunction with the accompanying drawings wherein:

FIGS. 24 and 25 illustrates an embodiment of a suture system in combination with another embodiment of a suture pin for securing two bone fragments;

FIG. 27 illustrates a bottom perspective view of the suture pin of FIGS. 24 and 25;

FIG. 28 illustrates a side view of the suture pin of FIGS. 24 and 25;

FIG. 29 illustrates a bottom view of the suture pin of FIGS. 24 and 25;

FIG. 30 illustrates an end view of the suture pin of FIGS. 24 and 25;

DETAILED DESCRIPTION

One embodiment of the present disclosure may feature suture systems and methods for coupling together two bones, bone segments, and/or tissue segments. The suture systems feature an all suture/thread construction which eliminates the need for the surgeon to tie knots during the surgical procedure.

By way of a brief overview explained in greater detail herein, one aspect of the present disclosure features a suture system which may be used for the treatment of hallux valgus (i.e., bunion); however, the suture system may also be used with other bones and/or may be used for the treatment of cracked and/or broken bone fragments. The suture system includes a suture construct having at least one reduction construct. The reduction construct includes a locking limb, a contractible loop, and an opposed loop disposed generally opposite to the contractible loop. The suture construct is configured to be selectively arranged in an expanded state/position and a reduced state/position. When in the expanded state/position, one or more of the contractible loops are passed through a respective passageway from through a first to the second bone or bone fragment until a portion of the contractible loop(s) extends beyond an opening in the second bone or bone fragment. A suture pin may be passed through the first (and optionally second contractible loop). To reduce/tighten the suture construct into the reduced state/position, the length/size of the opposed loop(s) is reduced thereby reducing the length/size of the first and second contractible loop(s) and biasing the first and second bones/bone fragments towards each other. Once the suture construct applies a desired amount of force to the bones/bone fragments in the reduced state, tension on the suture construct causes the opposed loop(s) to reduce against the locking limb(s), thereby locking, fixing, or otherwise securing the suture construct the reduced state.

Figure 1:
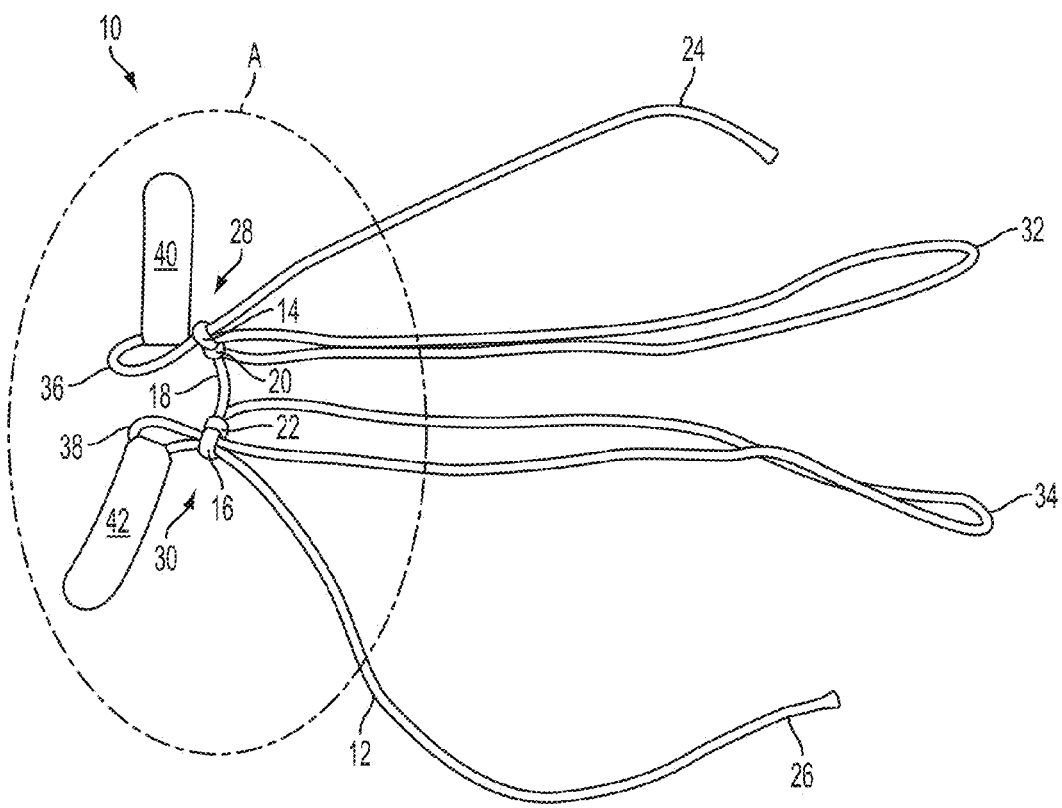
FIG. 1 is a plan view of one embodiment of a suture construct consistent with one embodiment of the present disclosure.

With reference to FIG. 1, one embodiment of a suture construct 10 is generally illustrated. The suture construct 10 includes one or more reduction constructs (e.g., a first and optionally a second reduction construct 28, 30). As explained herein, the first and the second reduction constructs 28, 30 (which may have the same or different configuration) are configured to be selectively reduced in size and locked, fixed, or otherwise secured in the reduced formation to apply a compressive force. While the suture construct 10 is illustrated having two reduction constructs 28, 30 separated by a bridge 18, it should be appreciated that a suture construct consistent with the present disclosure may include only one reduction construct 28.

The suture construct 10 may be formed from a single piece of suture 12, though it may also be formed from more than one piece of suture 12. The suture 12 may include woven and non-woven sutures, either of which may be formed from one or more threads or fibers. The threads/fibers may all be the same material or may include two or more different materials. The suture 12 may optionally include one or more coatings such as, but not limited to, antimicrobial materials to reduce potential infection. The suture 12 may include absorbable or non-absorbable materials. The diameter of the suture 12 will depend on the intended application; however, the suture 12 may include, but is not limited to, a #2, #3, #4 and/or #5 suture as defined by the United State Pharmacopeia (U.S.P.), for example, a #4 suture.

Figure 2:
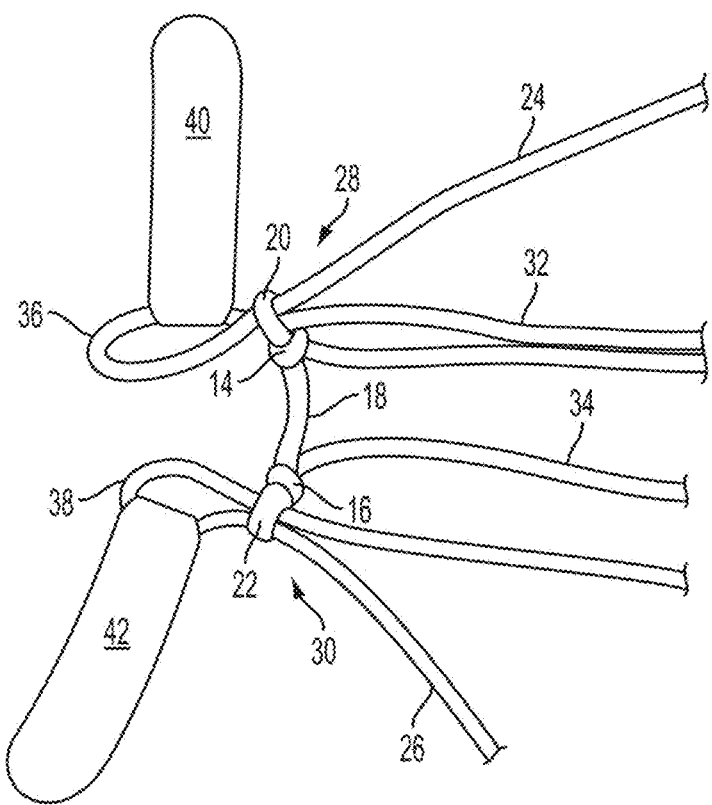
FIG. 2 is a close up of region A in FIG. 1.

With additional reference to FIG. 2 (which shows a close-up of region A in FIG. 1), the suture construct 10 includes the first and second reduction constructs 28, 30, each separated by a bridge 18. The first and second reduction constructs 28, 30 each include a first and a second knot 14, 16. The first and second knots 14, 16 may include any type of knot which can form a loop 20, 22, respectively. For example, one or more of the first and second knots 14, 16 may include splice (e.g., a sliding splice or the like), a slip knot, a running bowline, etc. Portions of the suture 12 are passed through a respective one of the loops 20, 22 to form the first and second reduction constructs 28, 30. The first and second reduction constructs 28, 30 each include a contractible loop 32, 34 and a opposed loop 36, 38, each of which are separated by the first and second loops 20, 22, respectively. A first portion of each of the opposed loops 36, 38 extends through the loops 20, 22 from the contractible loops 32, 34, respectively, and a second portion of each of the opposed loops 36, 38 extends through the loops 20, 22 and terminates at the first and second free ends 24, 26 of suture (also referred to as the first and second locking limbs 24, 26). A first portion of each of the contractible loops 32, 34 extends through the loops 20, 22 from the opposed loops 36, 38, respectively, and a second portion of each of the contractible loops 32, 34 extends from and terminates at the loops 20, 22.

Optionally, the first and second opposed loops 36, 38 may be temporarily retained in an expanded position (as generally illustrated in FIGS. 1 and 2) using a first and second tab 40, 42, respectively. The tabs 40, 42 may include, for example, folded pieces of metal (e.g., but not limited to, aluminum), plastic, suture, or the like configured to extend through the opposed loops 36, 38, thereby preventing the opposed loops 36, 38 from being pulled through the first and second loops 20, 22, respectively.

Figure 3:
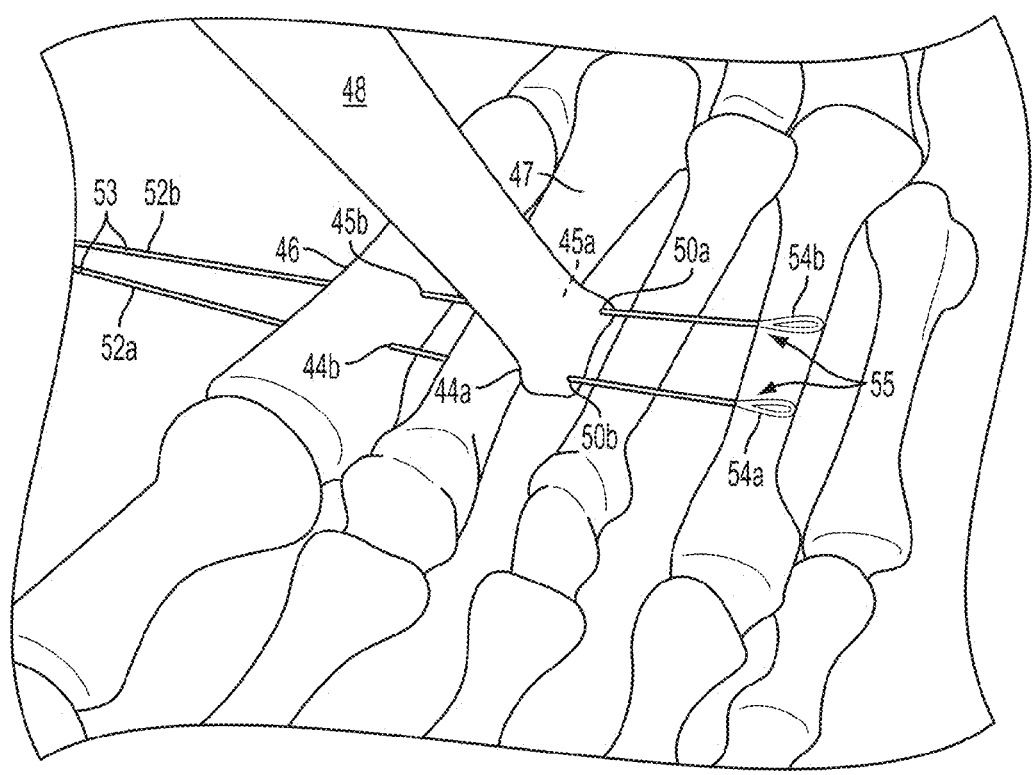
FIG. 3 illustrates one embodiment of forming the passageways through the bones consistent with the present disclosure.

Turning now to FIGS. 3-7, embodiments illustrating how the suture system can be used to treat a medical condition are generally illustrated. With reference to FIG. 3, two generally parallel passageways 44, 45 are drilled through a first and second bone 46, 47 (e.g., the first and second metatarsus bones 46, 47). A drill guide 48 may be used to form the passageways 44, 45. In particular, the drill guide 48 includes two drill bushings/openings 50a, 50b spaced apart from each other. The spacing of the bushings 50a, 50b is selected based on the size of the bones 46, 47 being drilled. In particular, the spacing may be selected such that the impact on the overall strength of the bones 46, 47 is minimized, thereby reducing the potential of damaging the bones 46, 47. By way of example, the spacing may be selected within the range of 6-10 mm. It should also be appreciated that the spacing between the first and second splices 14, 16 should generally correspond to the spacing of the bushings 50a, 50b.

In practice, the drill guide 48 may be placed against a portion of the second bone 47. A first passing pin or drill bit 52a (e.g., but not limited to, a 1.2 mm passing pin) is advanced through the first bushing 50a of the drill guide 48 to form a first second portions 44a, 44b (collectively referred to as the first passageway 44) in the first and second bones 46, 47, respectively. Similarly, a second passing pin or drill bit 52b is advanced through the second bushing 50b of the drill guide 48 to form a first second portions 45a, 45b (collectively referred to as the second passageway 45) in the first and second bones 46, 47, respectively. The distal ends 53 of the first and second drill bits 52a, 52b extend beyond the first bone 46 and the proximal ends 55 have not passed through the second bone 47. The first and second drill bits 52a, 52b optionally include a loop or snare 54a, 54b extending from the proximal ends 55.

Figure 4:
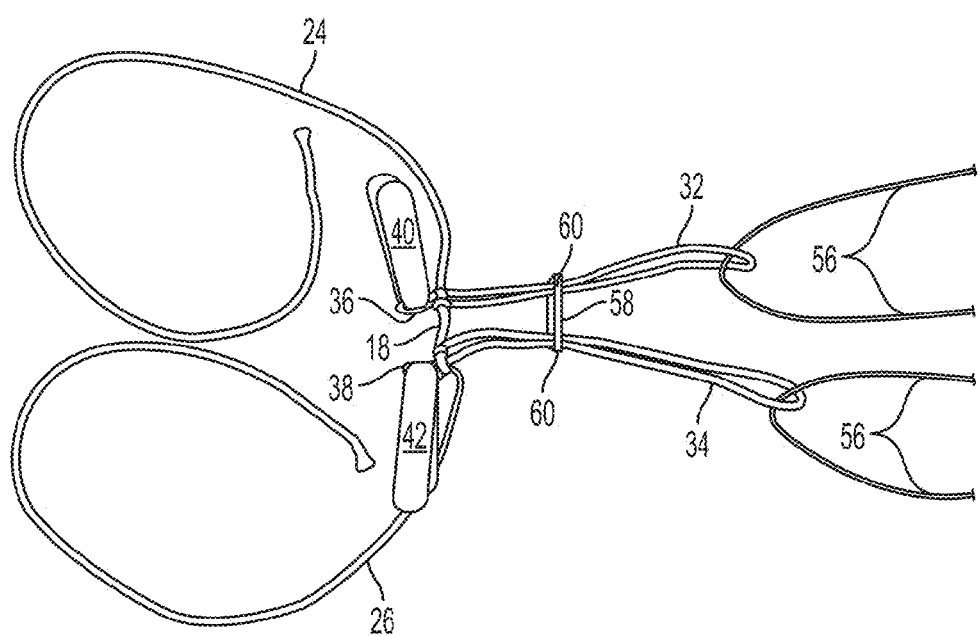
FIG. 4 illustrates one embodiment of the suture construct in combination with pull strands consistent with the present disclosure.

With the passageways 44, 45 having been formed, the suture construct 10 may then be advanced through the passageways 44, 45. Turning now to FIG. 4, the suture construct 10 is illustrated in combination with two pull strands 56. The pull strands 56 are disposed around a distal end of the first and second contractible loops 32, 34 and are configured to be releasably coupled to the first and second contractible loops 32, 34. For example, the pull strands 56 may include a loop disposed around the first and second contractible loops 32, 34. The pull strands 56 may also be tied or otherwise releasably secured to the first and second contractible loops 32, 34. Optionally, the suture construct 10 includes a suture plate 58. The suture plate 58 includes two apertures 60 spaced apart a distance generally corresponding to the distance between the two passageways 44, 45 and the spacing of the first and second knots 14, 16. The suture plates 58 may have a "figure 8" cross-section or may have a generally rectangular cross-section.

Figure 5:
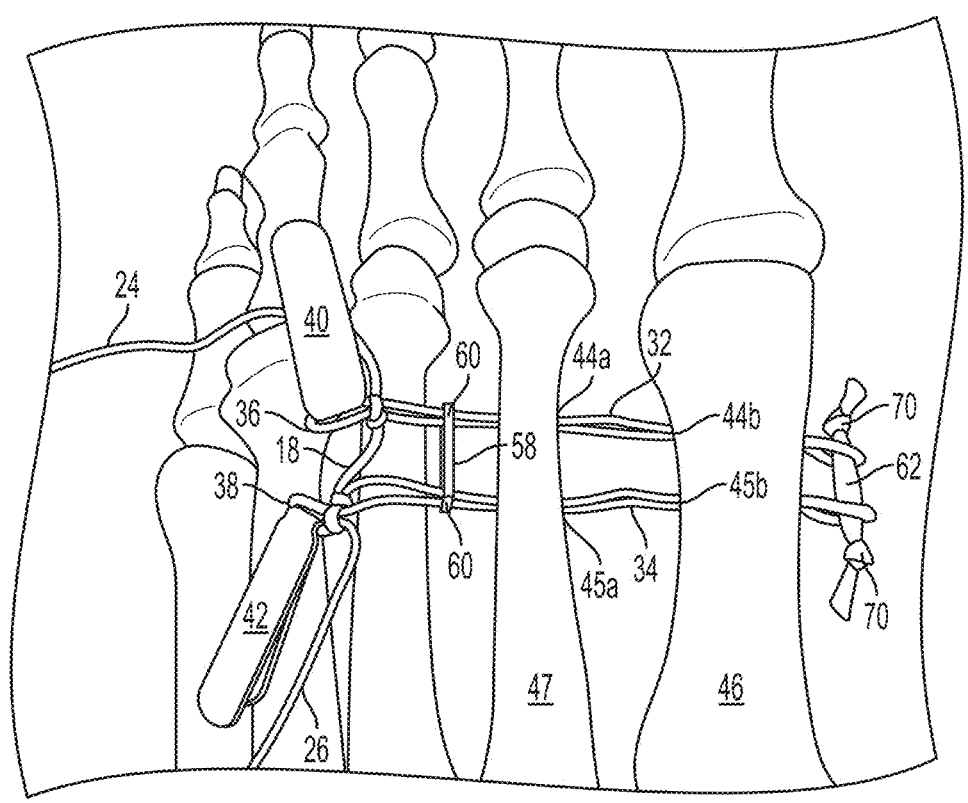
FIG. 5 illustrates the suture construct disposed within the passageways in the bone consistent with at least one embodiment of the present disclosure.
Figure 6:
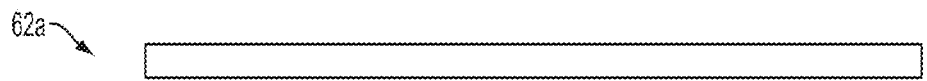
FIGS. 6-12 illustrate various embodiments of suture pins consistent with the present disclosure.

With reference to FIGS. 3, 4, and 5, the pull strands 56 are configured to be coupled to the loops/snares 54a, 54b extending from the drill bits 52a, 52b. The drill bits 52a, 52b are then retracted through the passageways 44, 45, thereby advancing the pull strands 56 through the passageways 44, 45. Once the pull strands 56 are beyond the first bone 46, the pull strands 56 can be used to pull/advance a portion of the contractible loops 32, 34 through a respective one of the passageways 44, 45 (from the second bone 47 and then through the first bone 46) until a distal portion of the contractible loops 32, 34 extends beyond the first bone 46. The contractible loops 32, 34 may be advanced through the passageways 44, 45 until the bridge 18 (or the optional suture plate 58) is proximate to or abuts against the second bone 47, thereafter the pull strands 56 may be disconnected/released from the first and second contractible loop 32, 34 as generally illustrated in FIG. 5.

With the first and second contractible loops 32, 34 advanced through the passageways 44, 45, the suture pin 62 (FIG. 5) is then coupled to the first and second contractible loop 32, 34 such that the suture construct 10 forms an enclosed loop extending around a portion of the first and second bones 46, 47. The enclosed loop suture construct is defined by the first and second contractible loops 32, 34, the bridge 18, and the suture pin 62. According to one embodiment, the suture pin 62 is passed through the first and second contractible loops 32, 34 such that a portion of the first and second contractible loops 32, 34 is disposed around a portion of the suture pin 62. Alternatively (or in addition), the suture pin 62 may be secured to the first and second contractible loops 32, 34 using one or more fasteners, clamps, or the like.

The suture pin 62 may have a length larger than the spacing between the two passageways 44, 45 in the first bone 46. Having the length of the suture pin 62 greater than the spacing between the two passageways 44, 45 in the first bone 46 allows the first and second contractible loops 32, 34 to extend substantially parallel to the two passageways 44, 45, thereby minimizing stress placed on the bones 46, 47 by the first and second contractible loops 32, 34. For example, if the first and second contractible loops 32, 34 are not parallel to the passageways 44, 45, then the first and second contractible loops 32, 34 will exert a force against the sideways of the passageways 44, 45 and/or the portion of bone between the passageways 44, 45, causing the first and second contractible loops 32, 34 to dig into and damage the bones 46, 47.

In addition to having a length greater than the spacing between the two passageways 44, 45 in the first bone 46, the suture pin 62 may also have an overall width, diameter, or cross-section that is greater than the diameter of the passageways 44, 45 such that the suture pin 62 will not fit within the passageways 44, 45. As explained herein, the suture pin 62 consistent with the present disclosure may be coupled to the first and second contractible loops 32, 34 after the first and second contractible loops 32, 34 have been advanced through the passageways 44, 45. As a result, the suture pin 62 does not need to be advanced through the passageways 44, 45 and diameter of the passageways 44, 45 may be minimized (i.e., the diameter of the passageways 44, 45 need only be slightly larger than the overall cross-section of the first and second contractible loops 32, 34). As may be appreciated, the smaller diameter of the passageways 44, 45 minimizes the negative impact on the strength of the bones 46, 47 by reducing the amount of bone material that is removed.

Turning now to FIGS. 6-12, various embodiments of the suture pin 62 are generally illustrated. For example, FIG. 6 generally illustrates a suture pin 62a having a generally elongated shape. The suture pin 62a may be formed from metal (e.g., but not limited to, stainless steel, titanium, aluminum, chromium cobalt, and/or any alloy thereof), plastic (e.g., but not limited to, polyether ether ketone (PEEK), polyethylene (PE) such as ultrahigh molecular weight polyethylene (UHMWPE) and high density polyethylene (HDPE), or the like), composite materials (e.g., reinforced plastics such as fiber-reinforced polymers, metal composites, ceramic composites, or the like), sutures (woven and/or non-woven suture), or the like. The suture pin 62a may have a generally consistent cross-section throughout its length. The suture pin 62a may have a generally circular cross-section and/or may have a non-circular cross-section (e.g., rectangular, oval, or the like).

Figure 7:
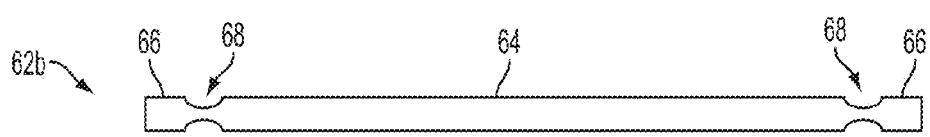

With reference to FIG. 7, a suture pin 62b is illustrated having a main body 64, an end region 66, and at least one reduced portion 68 having a smaller cross-section compared to the main body 64 and/or the end region 66. The reduced portion 68 may include a groove, slot, channel, or the like configured to aid in locating the first and second contractible loops 32, 34 with respect to the suture pin 66b, and aid in preventing the suture pin 62b from becoming dislodged with respect to the first and second contractible loops 32, 34 (i.e., aid in securing the first and second contractible loops 32, 34 with respect to the reduced portion 68). The reduced portions 68 may extend radially around only a portion of the suture pin 62b (e.g., 180 degrees around, 90 degrees around, or the like) or may extend radially around the entire cross-section of the suture pin 62b. The positions of the reduced portions 68 may be separated from each other a distance generally corresponding to the distance between the two passageways 44, 45 and the spacing of the first and second splices 14, 16. While the suture pin 62b is illustrated having two reduced portions 68, it should be appreciated that the suture pin 62b may include only one or may include more than two reduced portions 68 which are distributed along the length of the suture pin 62b. Having more than two reduced portions 68 may allow the suture pin 62b to be used to different suture constructs 10 having different spacing between the first and second splices 14, 16.

As generally illustrated in FIGS. 8-12, a suture pin 62 consistent with the present disclosure may also include one or more enlarged portions configured to aid in locating the first and second contractible loops 32, 34 with respect to the suture pin 66, and aid in preventing the suture pin 62 from becoming dislodged with respect to the first and second contractible loops 32, 34 (i.e., aid in securing the first and second contractible loops 32, 34 with respect to the enlarged portions). The enlarged portions may be separated from each other a distance which is generally equal to or greater than the distance between the two passageways 44, 45 and the spacing of the first and second splices 14, 16.

Figure 8:
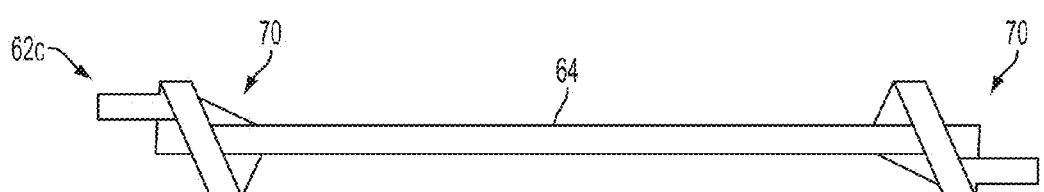

One embodiment of a suture pin 62c having an enlarged portion is generally illustrated in FIG. 8. More specifically, the suture pin 62c is formed from one or more pieces of suture (either woven or non-woven suture). The suture pin 62c includes enlarged portions 70 disposed at generally opposite end regions of a main body 64. The enlarged portions 70 have a cross-section that is larger than the cross-section of the main body 64. The overall width, diameter, or cross-section of the enlarged portions 70 may also be greater than the diameter of the passageways 44, 45 such that the suture pin 62c will not fit within the passageways 44, 45.

The enlarged portions 70 may be formed by forming one or more knots (such as, but not limited to, an overhand knot, half hitch knot, square knot, half knot, or the like). The knots may be made from the same piece of suture as the main body 64, and/or may include additional pieces of suture. A benefit to a suture pin having an all-suture construction is that is minimizes the amount of different materials used by the suture system. Additionally, tissue may grow into the suture material, thereby reducing the possibility of the suture pin 62c from migrating with respect to the first and second contractible loops 32, 34.

Figure 9:
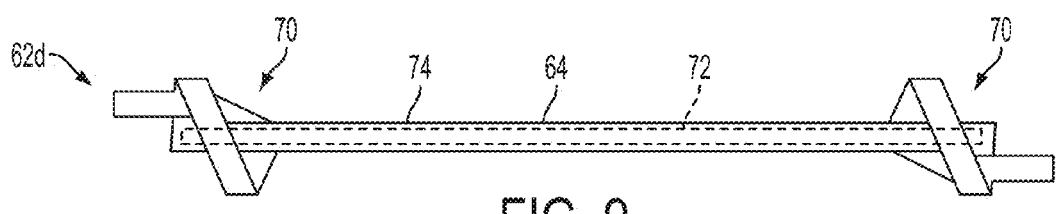

Another embodiment of a suture pin 62d having enlarged portions 70 is generally illustrated in FIG. 9. The suture pin 62d may be similar to the suture pin 62c, however, the suture pin 62d includes a rigid element/member 72 over which the suture 74 is woven, tied, or otherwise secured around. For example, the rigid element 72 may include an elongated member (e.g., a pin or the like as generally described in FIGS. 6, 7, and 10-12). The combination of the rigid element 72 and the suture element 74 may increase the structural rigidity of the suture pin 62d, thereby facilitating the assembly of the suture system during the surgical procedure. Additionally, the combination of the rigid element 72 and the suture element 74 may increase the overall strength of the suture pin 62d, and may also allow for tissue growth into the suture element 74 as discussed herein.

Figure 10:
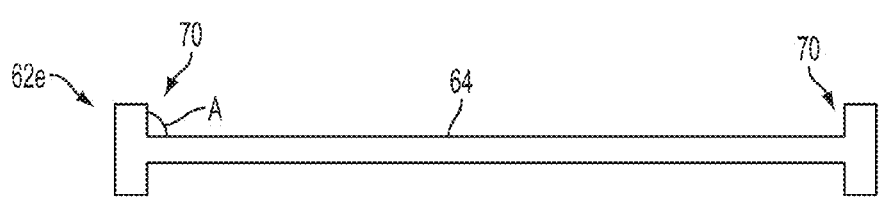
Figure 11:
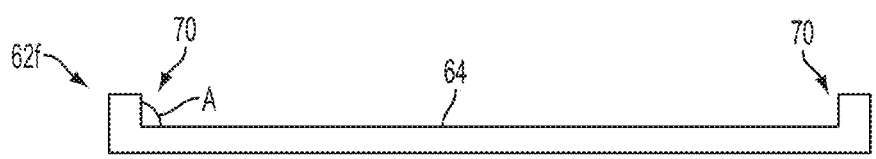
Figure 12:
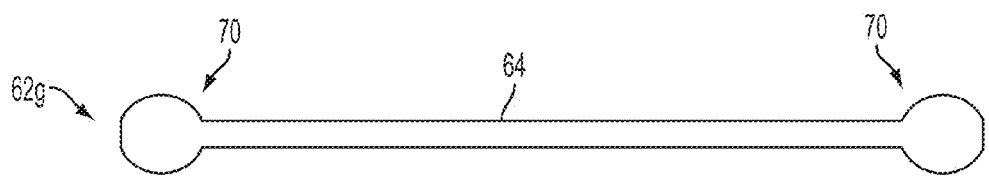

Other embodiments of a suture pin 62e-62g having enlarged portions 70 are generally illustrated in FIGS. 10-12. The suture pins 62e-62g include a generally elongated main body 64 having enlarged portions 70 disposed about the proximal end regions. The main body 64 and the enlarged portions 70 may be formed as an integral component (e.g., pieces bonded together, which may be made from the same or different materials) or may be formed as a unitary component (i.e., formed as a single component from the same material). The suture pins 62e-62g may be formed from metal (e.g., but not limited to, stainless steel, titanium, aluminum, chromium cobalt, and/or any alloy thereof), plastic (e.g., but not limited to, polyether ether ketone (PEEK), polyethylene (PE) such as ultrahigh molecular weight polyethylene (UHMWPE) and high density polyethylene (HDPE), or the like), or composite materials (e.g., reinforced plastics such as fiber-reinforced polymers, metal composites, ceramic composites, or the like).

The enlarged portions 70 may have a generally "T" shaped or disc-shaped protrusion extending generally radially outward as generally illustrated in FIG. 10 or a may have a generally "L" shaped protrusion extending generally radially outward as generally illustrated in FIG. 11. While the protrusions are illustrated extending radially outward at approximately 90 degrees from the body portion 64, it should be appreciated that the protrusions may extend radially outwardly at an angle A from the body portion 64 in the range of 10 degrees to 170 degrees. Additionally, while the protrusions are illustrated having a generally planar or linear shape, it should be understood that the protrusions may have a non-linear or non-planar shape such as a curved or arcuate shape. The enlarged portions 70 may also have a generally circular or cross-section, spherical shape, and/or may have a non-circular cross-section (e.g., rectangular, oval, or the like) as generally illustrated in FIG. 12.

Figure 13:
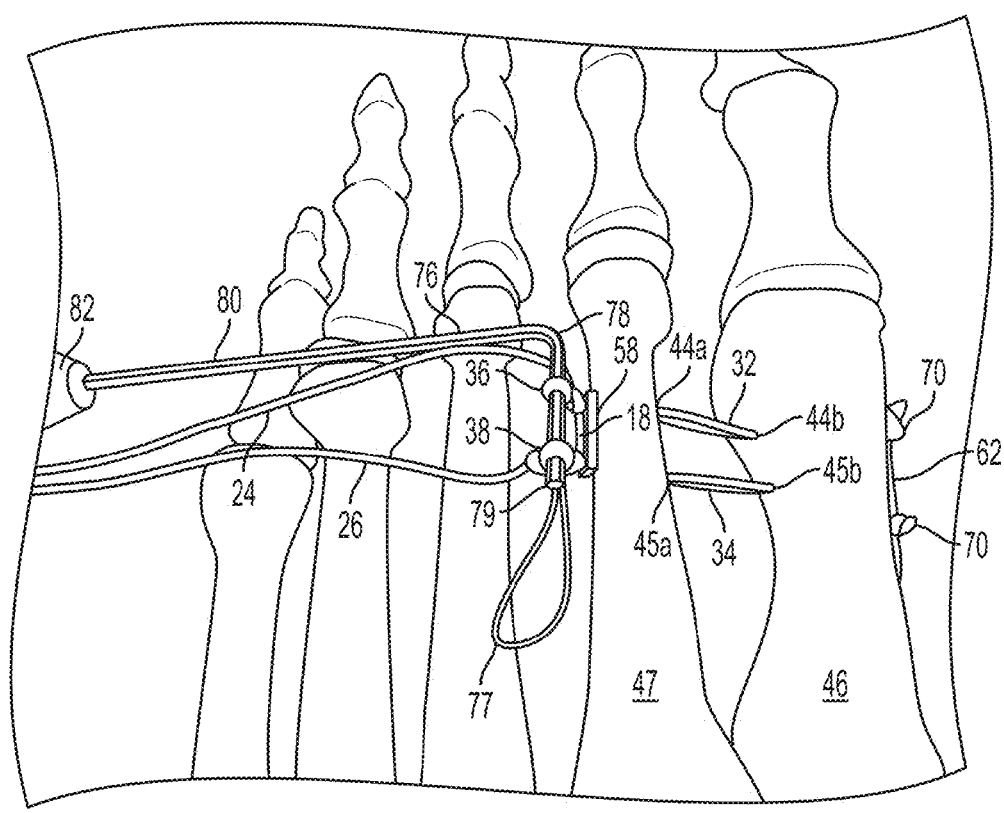
FIG. 13 illustrates one embodiment of the suture construct in combination with one embodiment of a pusher consistent with the present disclosure.

Turning back to FIG. 5, with the suture pin 62 extending between the first and second contractible loops 32, 34, the first and second contractible loops 32, 34 may be pulled away from the first bone 46 to urge the suture pin 62 against the first bone 46, thereby aiding in maintaining the suture pin 62 within the first and second contractible loops 32, 34. The first and second tabs 40, 42 are removed from the first and second opposed loops 36, 38 and a pusher 76 is advanced through the first and second opposed loops 36, 38 as generally illustrated in FIG. 13.

The pusher 76 is configured to aid in reducing/tightening the suture system and to urge the first and second bones 46, 47 towards each other. According to one embodiment, the pusher 76 includes a pivoting section 78 which is advanced through the first and second opposed loops 36, 38 and a pull snare 77 extending outward beyond the distal end 79 of the pivoting section 78. The pivoting section 78 optionally extends at an angle from an arm section 80. While the angle between the pivoting section 78 and the arm section 80 is illustrated at approximately 90 degrees, it should be appreciated that the angle therebetween will depend on the application and the surgeon's preference and may, for example, be in the range of 45 to 135 degrees. The pusher 76 also optionally includes a handle portion 82 coupled to the arm section 80 to aid in gripping the pusher 76.

To reduce/tighten the suture system, the surgeon pulls the locking limbs 24, 26 of the suture construct 10 away from the second bone 47 while simultaneously urging the pusher 76 towards the second bone 47, thereby reducing the length of the first and second contractible loops 32, 34 and applying a compressive force through the first and second contractible loops 32, 34, the bridge 18 (and the optional suture plate 58), and suture pin 62 to bias the first and second bones 46, 47 towards each other. More specifically, the length of the locking limbs 24, 26 of the suture construct 10 is extended as a portion of the suture 12 is pulled from the first and second contractible loops 32, 34 and through the opposed loops 36, 38. The pusher 76 prevents the opposed loops 36, 38 from self-collapsing as the locking limbs 24, 26 are pulled and effectively acts as a pulley.

Figure 14:
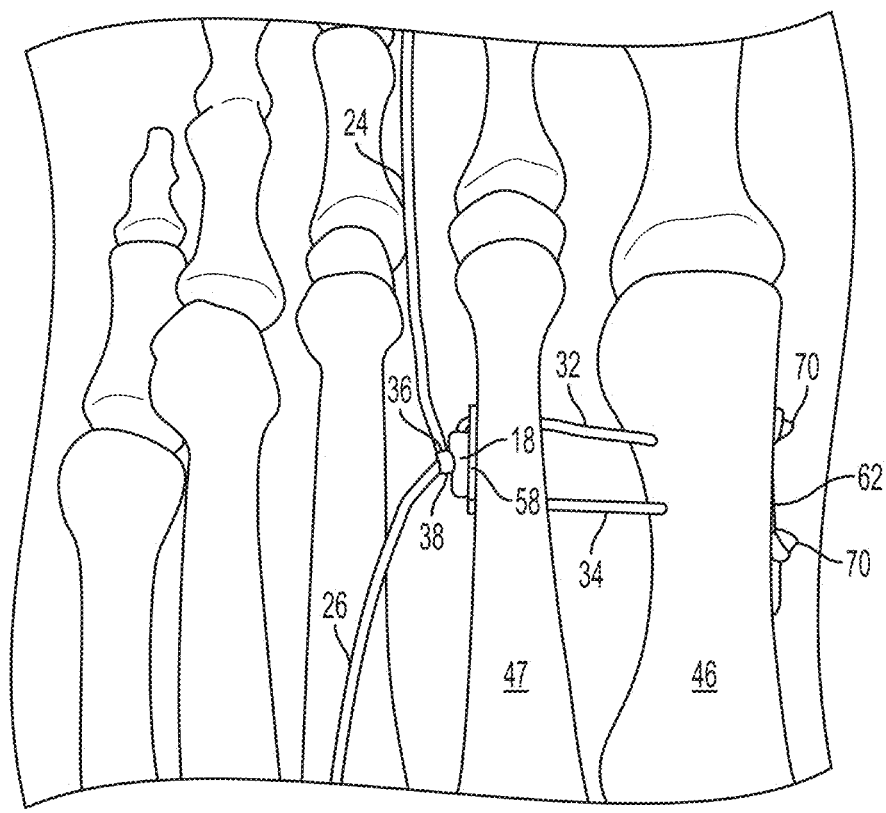
FIG. 14 illustrates the suture construct in a locked state consistent with at least one embodiment of the present disclosure.

Once the suture system applies a desired amount of force to urge the first and second bones 46, 47 towards each other, the locking limbs 24, 26 of the suture construct 10 are advanced into and captured by the pull snare 77 extending out from the distal end 79 of the pusher 76. The pusher 76 is then retracted through the first and second opposed loops 36, 38, causing a least a portion of the locking limbs 24, 26 to pass through the opposed loops 36, 38 as generally illustrated in FIG. 14. The tension on the suture construct 10 causes the opposed loops 36, 38 to reduce against the locking limbs 24, 26, thereby locking the suture construct 10 and preventing the suture construct 10 from loosening. Once the suture construct 10 is locked, excess lengths of the locking limbs 24, 26 may be trimmed proximate to the opposed loops 36, 38.

Figure 15:
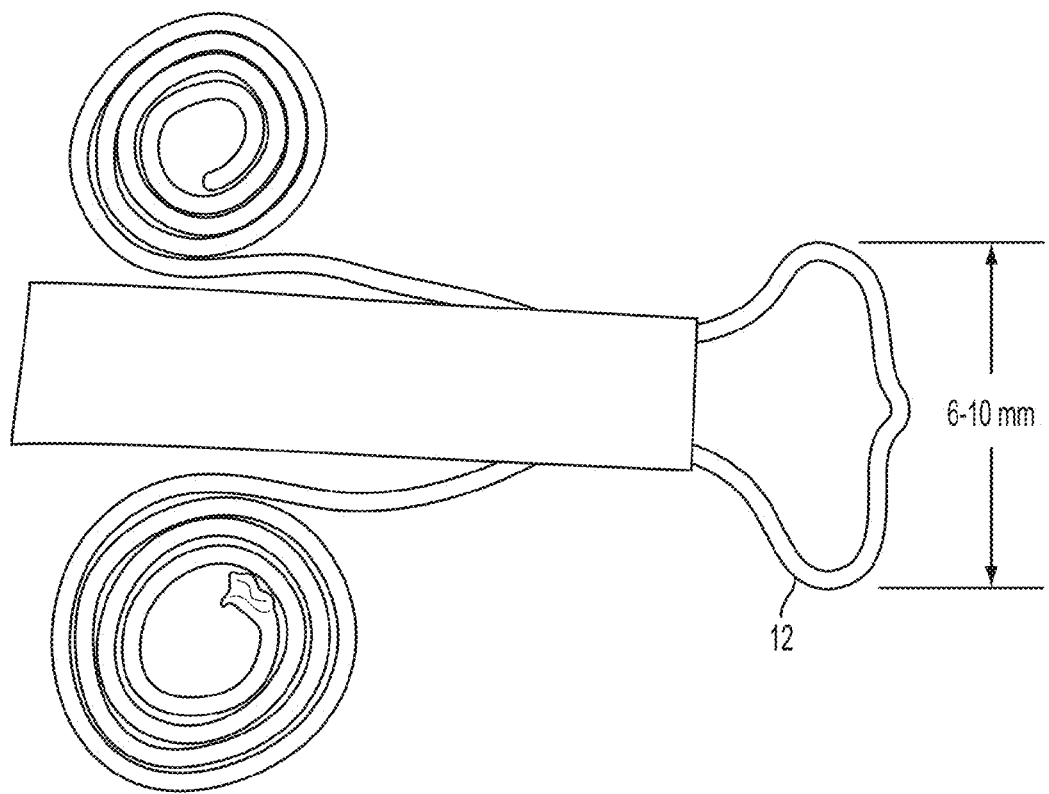
FIGS. 15-18 illustrate various steps for forming a suture construct consistent with at least one embodiment of the present disclosure.
Figure 16:
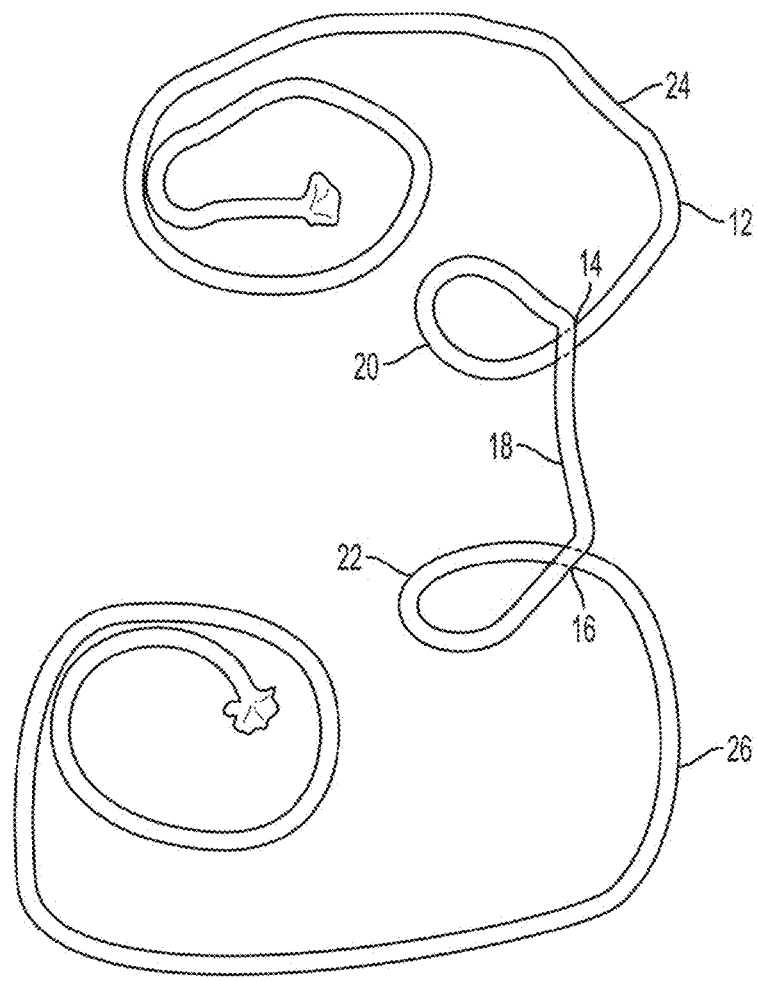
Figure 17:
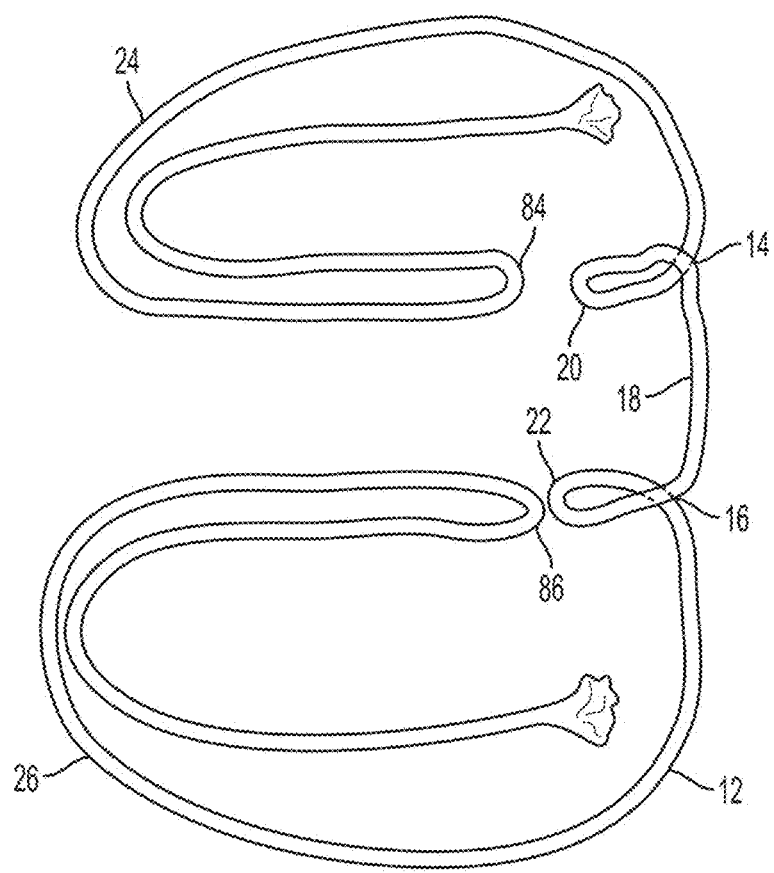
Figure 18:
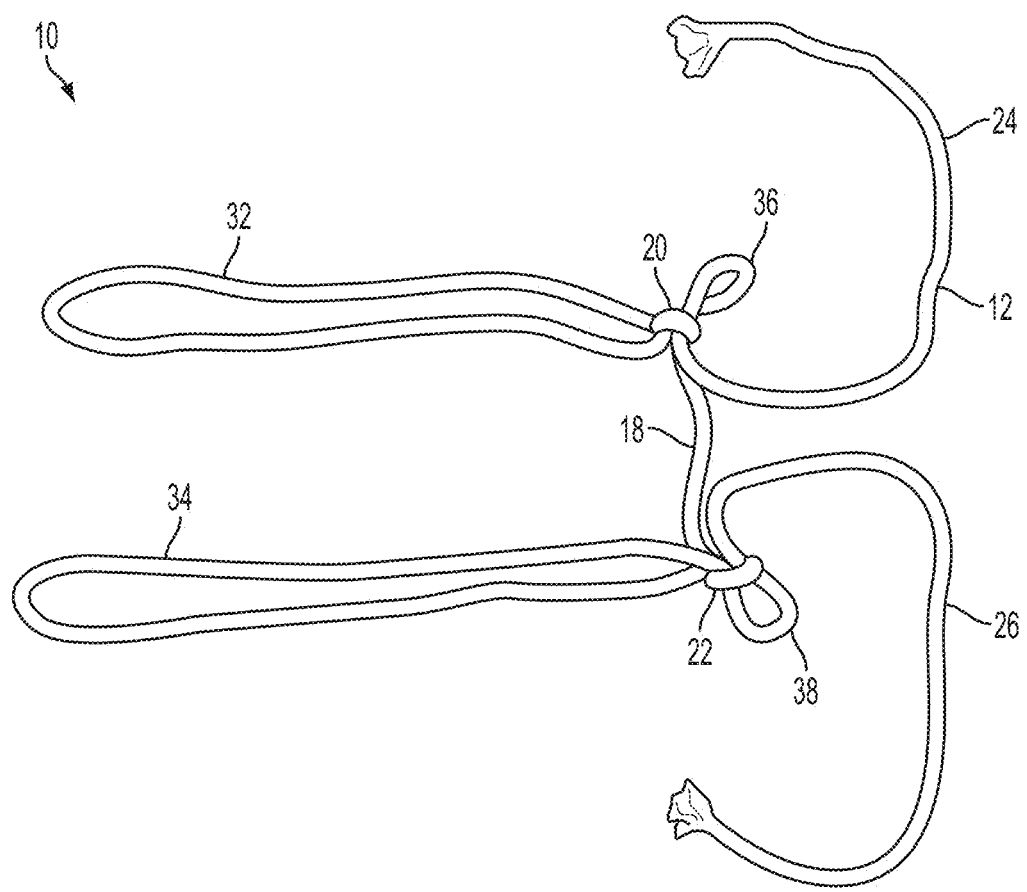

Turning now to FIGS. 15-18, the steps for forming one embodiment of a suture construct 10 consistent with one embodiment of the present disclosure is generally illustrated. With reference to FIG. 15, a length of suture 12 is provided and the spacing between the first and second knots 14, 16 is determined based on the desired spacing between the first and second passageways 44, 45. Turning now to FIG. 16, the first and second knots 14, 16 are formed in the suture 12 (for example, but not limited to, using any splicing technique known to those skilled in the art) and are separated by the bridge 18. The first and second loops 20, 22 are also formed as a result of forming the first and second knots 14, 16, respectively. Intermediate portions 84, 86, FIG. 17, of the suture 12 are then passed through the first and second loops 20, 22 to form the first and second contractible loops 32, 34 and the first and second opposed loops 36, 38 as generally illustrated in FIG. 18.

Figure 19:
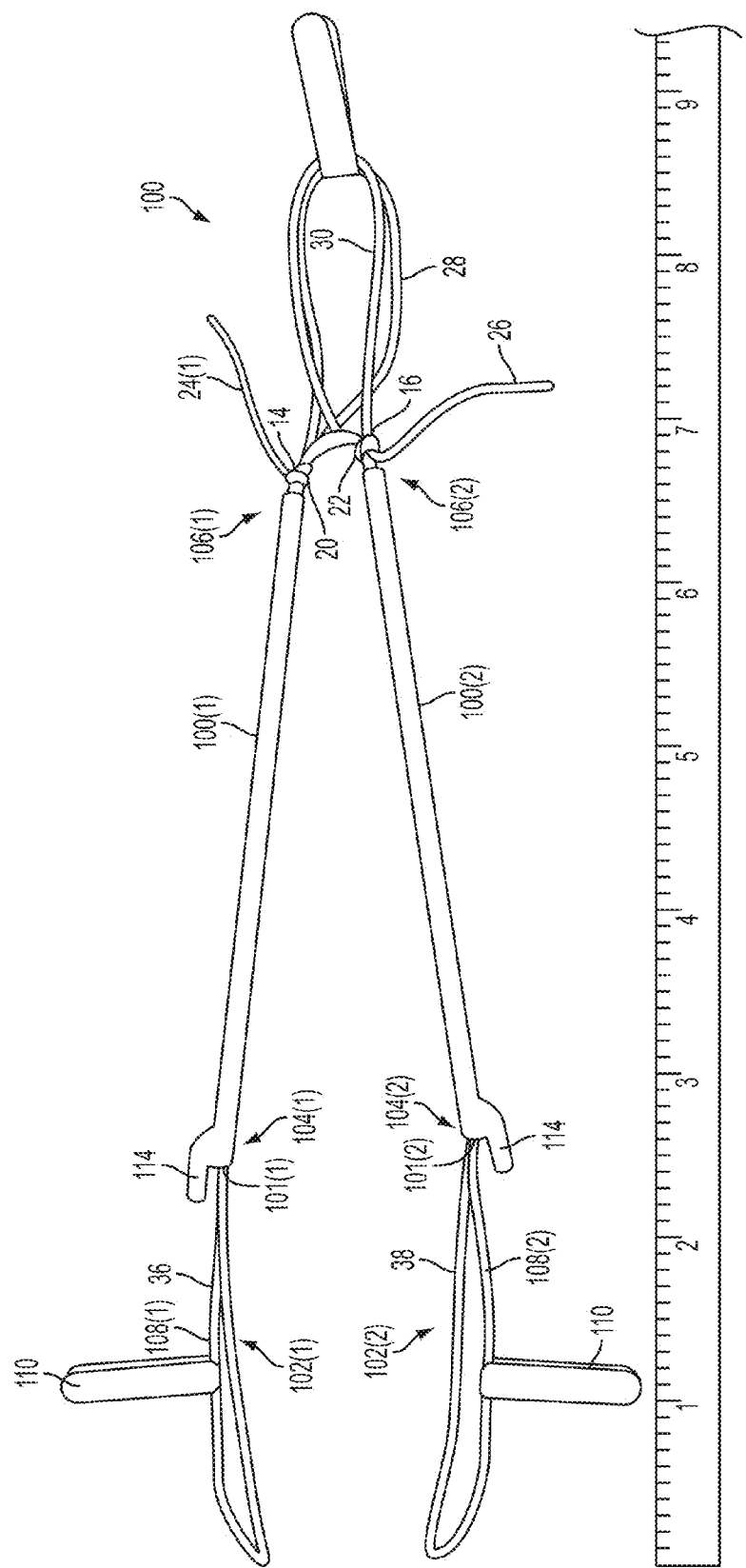
FIG. 19 illustrates another embodiment of suture system.

With reference to FIG. 19, another embodiment of a suture system 1a is generally illustrated. The suture system 1a includes a suture construct 10a, a first and a second pusher tubes 100(1), 100(2), a suture pin 62 (not shown for clarity), and optionally a suture plate 58 (also not shown for clarity). The suture construct 10a is similar to the suture construct 10 described herein, except that the first and second opposed loops 36, 38 have been lengthened, the locking limbs 24, 26 of the suture 12 have been advanced through the opposed loops 36, 38, and the lumens 101(1), 101(2) of the pusher tubes 100(1), 100(2) have been advanced over a portion of the opposed loops 36, 38 such that a distal portion 102(1), 102(2) of the opposed loops 36, 38 extends beyond a distal end 104(1), 104(2) of the pusher tubes 100(1), 100(2). The proximal ends 106(1), 106(2) of the pusher tubes 100(1), 100(2) are proximate to and/or abuts against the splice snares 20, 22 and/or the splices 14, 16, respectively. Optionally, the "hot side" 108(1), 108(2) of the opposed loops 36, 38 may be marked, for example, using one or more marking indicia, tabs 110 or the like. As used herein, the term "hot sides" of the opposed loops 36, 38 refers to the portions of the opposed loops 36, 38 which pass through the first and second loops 20, 22 from the first and second contractible loops 32, 34 when the first and second contractible loops 32, 34 are reduced in size.

The suture construct 10a of the system 1a is installed in the first and second bones 46, 47 in a manner similar to the suture construct 10. For the sake of brevity, all of the installation steps of the suture system 1a have not been repeated, and reference is made to the remainder of the instant application. Specifically, the passageways 44, 45 may be formed in the bones 46, 47 and the contractible loops 32, 34 are advanced through a respective one of the passageways 44, 45 (from the second bone 47 and then through the first bone 46) until a distal portion of the contractible loops 32, 34 extends beyond the first bone 46 in the same manner as described herein. The contractible loops 32, 34 may be advanced through the passageways 44, 45 until the bridge 18 (or the optional suture plate 58) is proximate to or abuts against the second bone 47. With the first and second contractible loops 32, 34 advanced through the passageways 44, 45, a suture pin 62 is then coupled to the first and second contractible loops 32, 34 such that the suture construct 10 forms an enclosed loop extending around a portion of the first and second bones 46, 47 in the same manner described herein. With the suture pin 62 extending between the first and second contractible loops 32, 34, the first and second contractible loops 32, 34 may be pulled away from the first bone 46 to urge the suture pin 62 against the first bone 46, thereby aiding in maintaining the suture pin 62 within the first and second contractible loops 32, 34.

Figure 20:
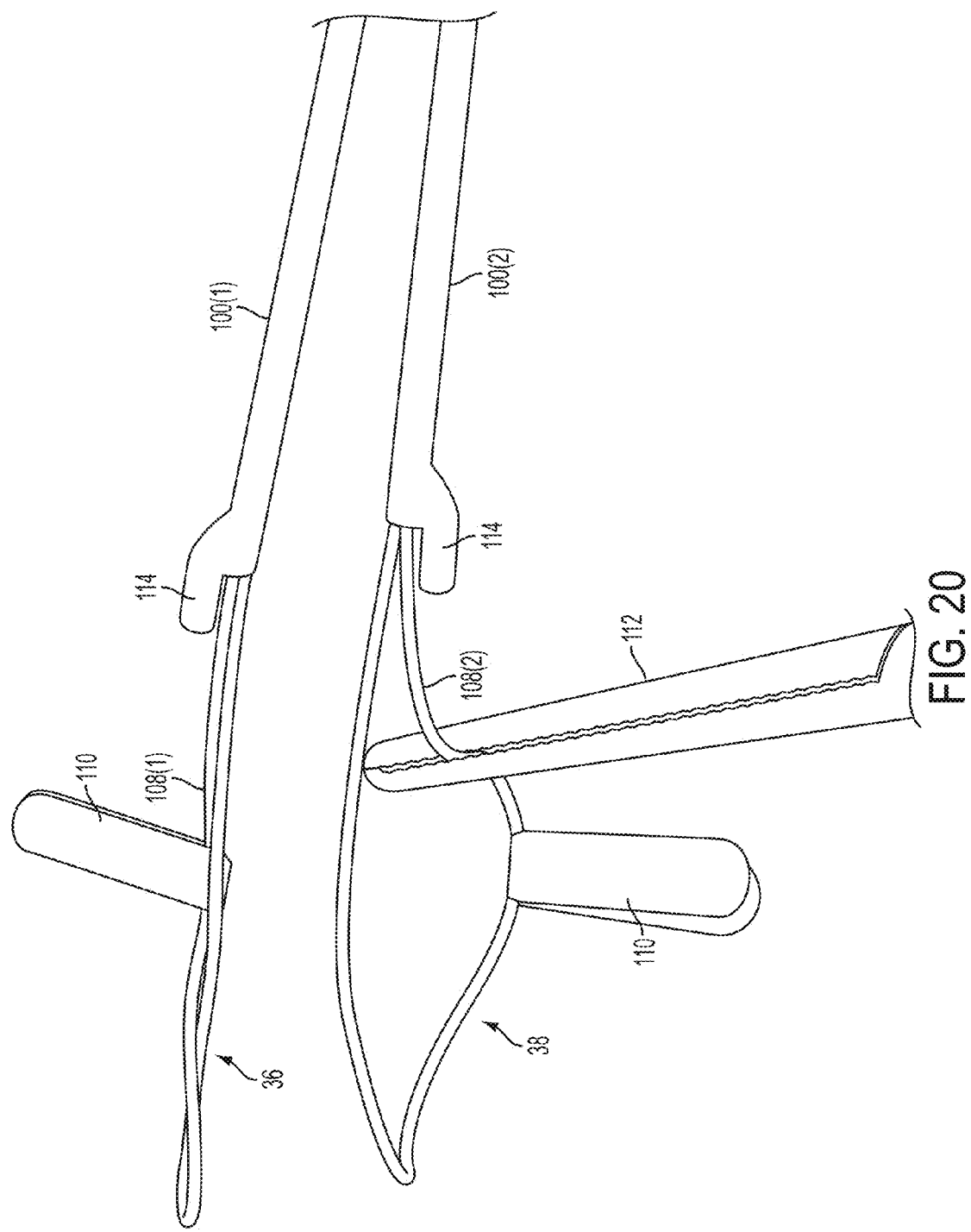
FIGS. 20 and 21 illustrate installation/reduction steps corresponding to the suture system illustrated in FIG. 19.
Figure 21:
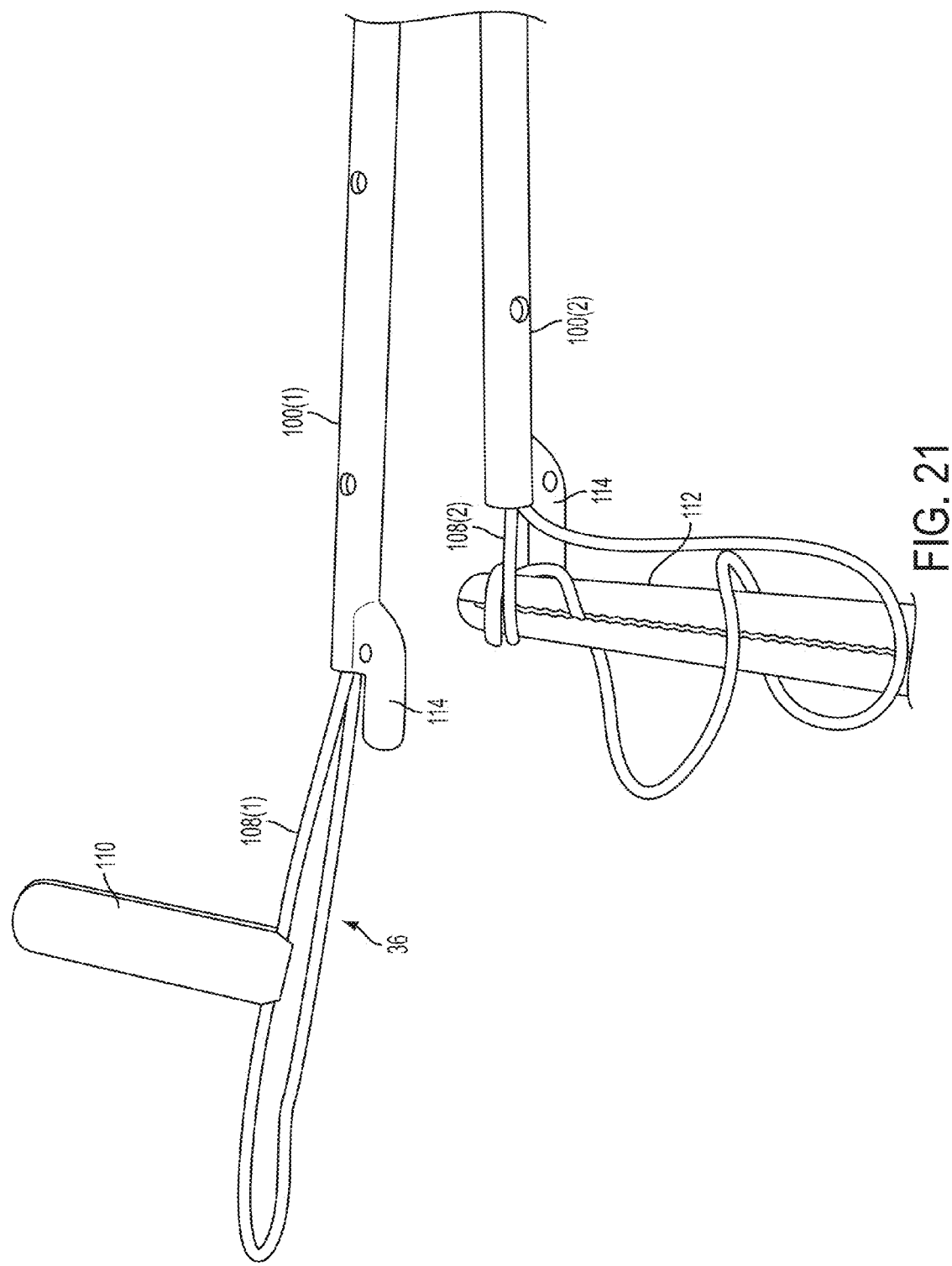

Whereas the reduction of the suture construct 10 utilized a pusher 76, the installation and reduction of the suture construct 10a replaces the pusher 76 and utilizes one or more pusher tubes 100(1), 100(2) instead. More specifically, with the suture pin 62 extending between the first and second contractible loops 32, 34 and urged against the first bone 46, the user grasps the hot sides 108(1), 108(2) (for example, using a gripper, grasper, forceps, 112 or the like as generally illustrated in FIG. 20) of the opposed loops 36, 38 and pulls the hot sides hot sides 108(1), 108(2) through the pusher tubes 100(1), 100(2) and distally or away from the contractible loops 32, 34 (for example, but not limited to, rotating or twisting the forceps 112 against a distal end 104(1), 104(2) of the pusher tubes 100(1), 100(2) as generally illustrated in FIG. 21). The pusher tubes 100(1), 100(2) may have a length sufficient to allow the surgeon to operate on the distal ends 104(1), 104(2) outside of the patient's tissue.

As may be appreciated, pulling the hot sides 108(1), 108(2) of the opposed loops 36, 38 causes the length of the contractible loops 32, 34 to be reduced since the hot sides 108(1), 108(2) are slidably coupled to the contractible loops 32, 34 through the loops 20, 22. Reducing the lengths of the opposed loops 36, 38 applies a compressive force through the first and second contractible loops 32, 34, the bridge 18 (and the optional suture plate 58), and suture pin 62 to bias the first and second bones 46, 47 towards each other. Once the desired amount of compressive force is applied to the bones 46, 47, the suture construct 10a may be temporarily maintained in the compressed state by urging the pusher tubes 100(1), 100(2) against the loops 20, 22 and/or the knots 14, 16, and the tension on the hot sides 108(1), 108(2) (e.g., by means of the forceps 112) may be temporarily eliminated. While urging the pusher tubes 100(1), 100(2) against the loops 20, 22 and/or the knots 14, 16, the user may then pull on the locking limbs 24, 26 of the suture construct 10a. As noted above, the locking limbs 24, 26 are already passed through the opposed loops 36, 38. As the user pulls on the locking limbs 24, 26, the length of the opposed loops 36, 38 decreases until the opposed loops 36, 38 are compressed against the locking limbs 24, 26 extending therethrough. The tension on the suture construct 10a causes the opposed loops 36, 38 to reduce against the locking limbs 24, 26, thereby locking the suture construct 10a and preventing the suture construct 10a from loosening. Once the suture construct 10a is locked, excess lengths of the locking limbs 24, 26 may be trimmed proximate to the opposed loops 36, 38.

The pusher tubes 100(1), 100(2) optionally include one or more outriggers 114 extending generally outward from the distal ends 104(1), 104(2) of the pusher tubes 100(1), 100(2), for example, outwardly from the longitudinal axis of the pusher tubes 100(1), 100(2) as generally illustrated in FIG. 21. The outriggers 114 may facilitate pulling the hot sides 108(1), 108(2) of the opposed loops 36, 38 through the pusher tubes 100(1), 100(2). More specifically, the outrigger 114 is configured to provide an increased area against which the forceps or other grasper 112 may contact against.

Figure 22:
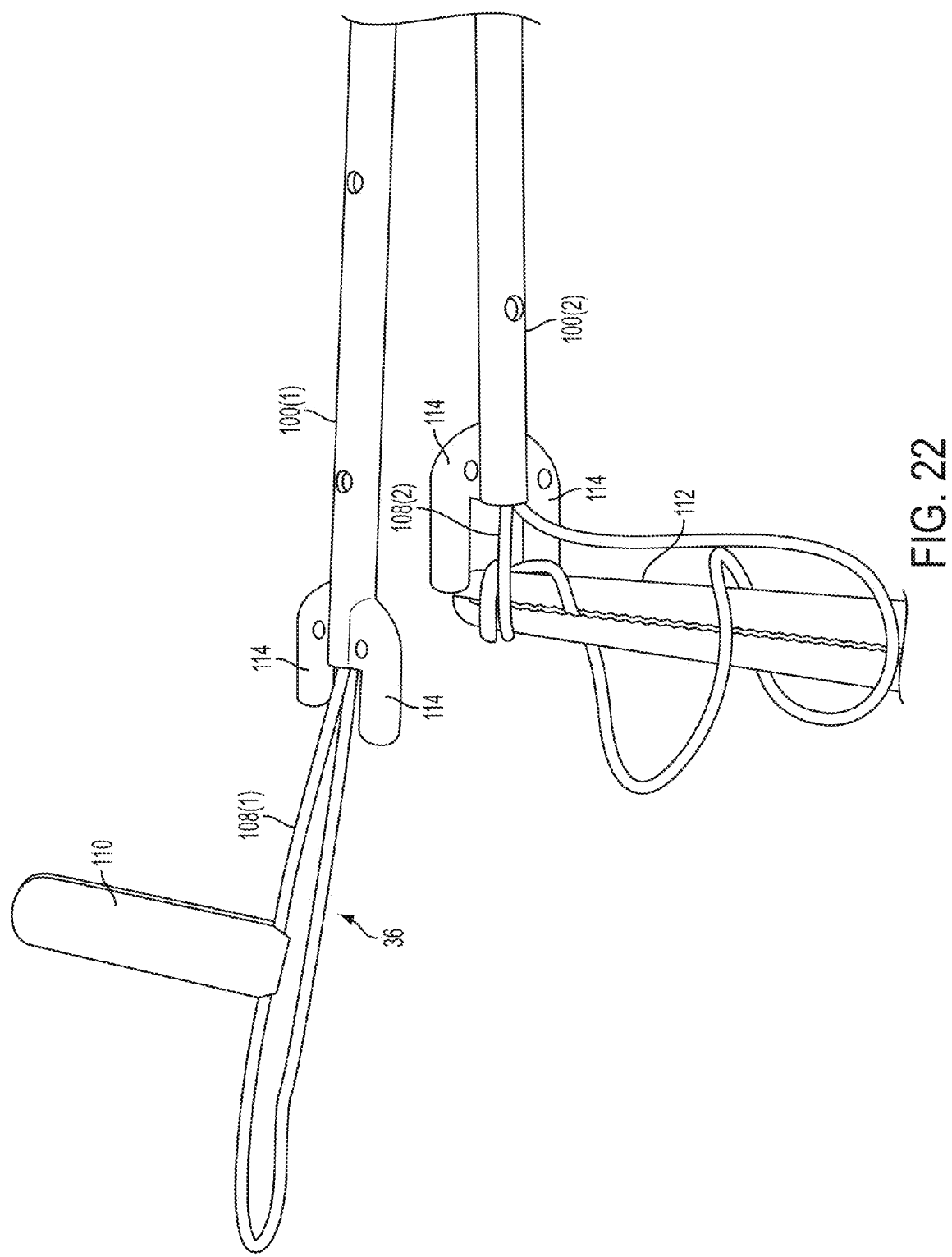
FIG. 22 illustrates another embodiment of the pusher tubes consistent with the present disclosure.
Figure 23:
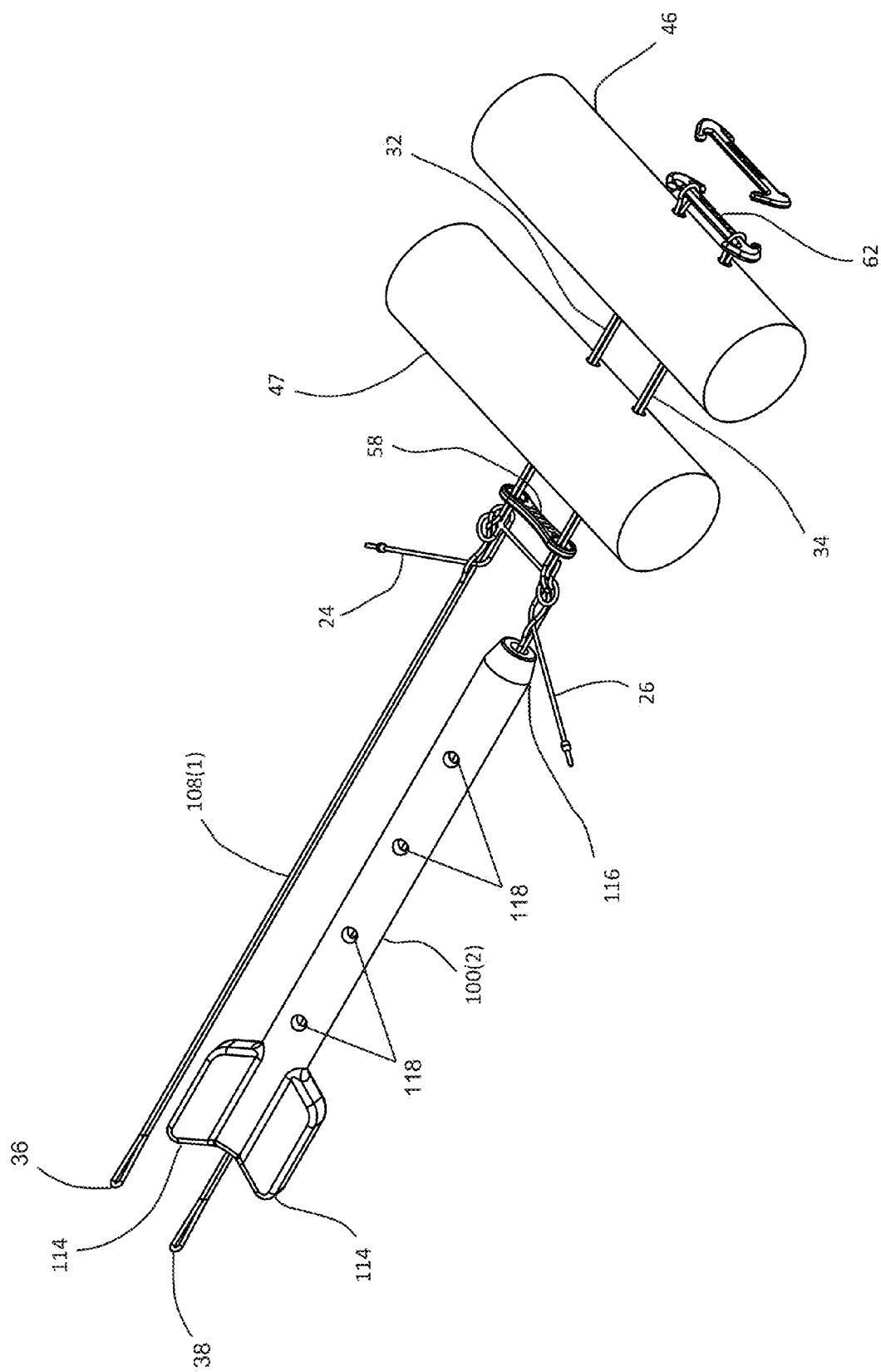
FIG. 23 illustrates a further embodiment of the pusher tubes consistent with the present disclosure.

With reference to FIG. 22, the pusher tubes 100(1), 100(2) may include a plurality of outriggers 114(1)-114(n) extending generally outwardly from the distal ends 104(1), 104(2) of the pusher tubes 100(1), 100(2). For example, the pusher tubes 100(1), 100(2) may include a first and a second outrigger 114(1), 114(n) which extend outward from generally opposite sides of the pusher tubes 100(1), 100(2), e.g., the first and second outriggers 114(1), 114(2) to form a cradle-like structure configured to reduce and/or prevent the forceps/graspers 112 from slipping off the distal ends 104(1), 104(2) of the pusher tubes 100(1), 100(2) as the forceps/graspers 112 are rotated or twisted. For example, the first and second outriggers 114(1), 114(2) may be disposed approximately 180 degrees from each other. It should be appreciated, however, that the first and second outriggers 114(1), 114(2) may be disposed at any other angle relative to each other to form a crook. For example, the first and second outriggers 114(1), 114(2) may be disposed at an angle less than 180 degrees relative to each other, for example, an obtuse angle as generally illustrated in FIG. 23.

Optionally, one or more of the proximal ends 160(1), 106(2) of the pusher tubes 100(1), 100(2) may include a taper 116 to aid in visualization of the tip. Additionally, the pusher tubes 100(1), 100(2) may optionally include one or more apertures 118. The apertures 118 may facilitate sterilization of the pusher tubes 100(1), 100(2) by allowing the sterilization medium to more easily flow through the lumens 101(1), 101(2) of the pusher tubes 100(1), 100(2) and/or may facilitate molding of the pusher tubes 100(1), 100(2) by allowing pins to be aligned through the apertures 118 to aid in aligning a centering pins disposed through the lumens 101(1), 101(2).

The pusher tubes 100(1), 100(2) facilitate the reduction of the suture construct 10a. In particular, the pusher tubes 100(1), 100(2) allow the user to pull the suture 12 (e.g., the hot sides 108(1), 108(2)) from the opposed loops 36, 38 linearly through the first and second loops 20, 22, thereby allowing a user to more easily apply a much greater amount of compressive force through the suture system 1a. Moreover, rotating/twisting the hot sides 108(1), 108(2) using the forceps 112 on the distal ends 104(1), 104(2) of the pusher tubes 100(1), 100(2) creates a mechanical advantage (e.g., a pulley-like effect) which greatly increases the amount of compressive force which may be applied through the suture system 1a.

Figure 26:
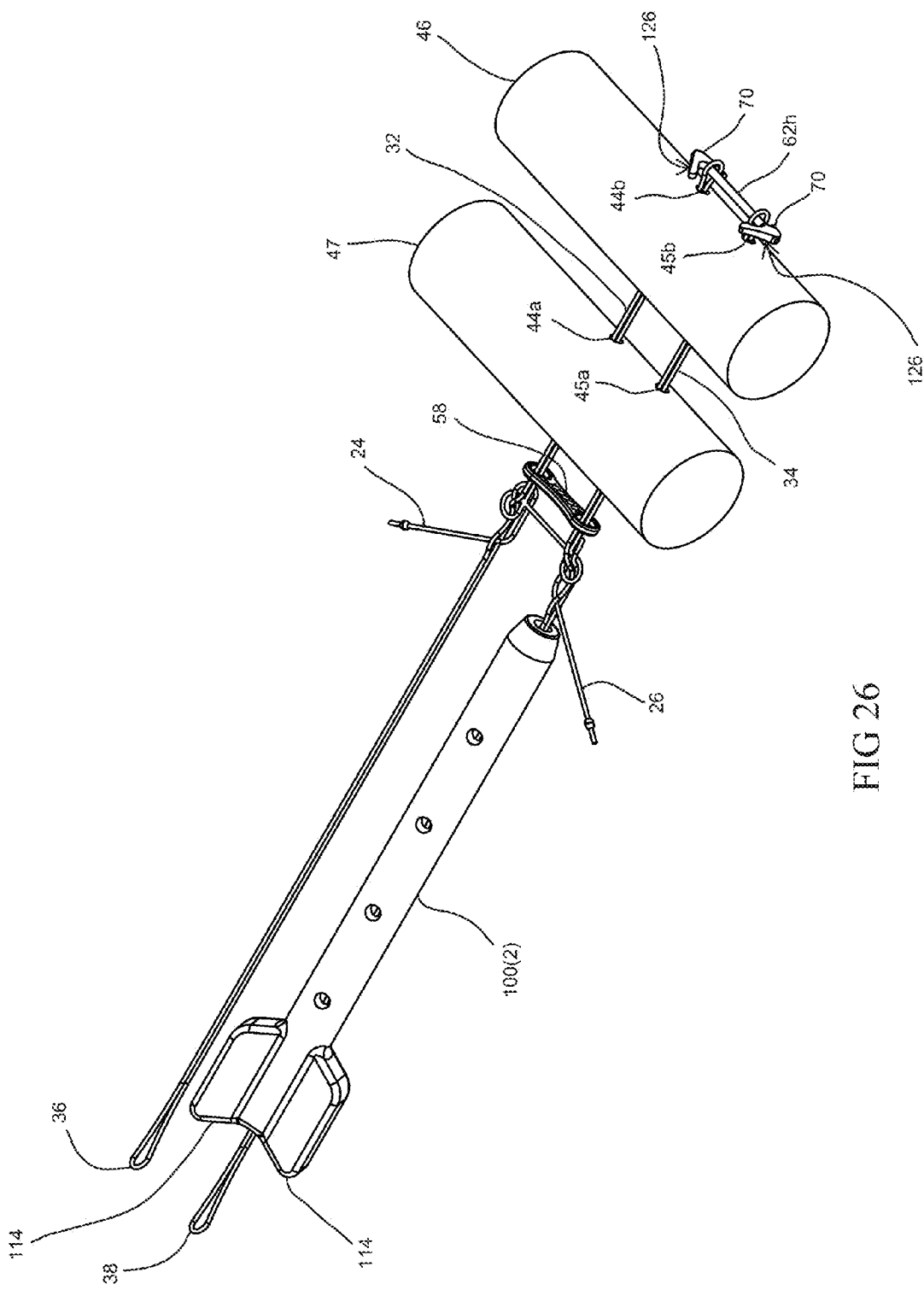
FIG. 26 illustrates an embodiment of a suture system in combination with the suture pin of FIGS. 24 and 25 for securing two bones.

Turning now to FIGS. 24-30, another embodiment of a suture pin 62h is generally illustrated. In particular, FIGS. 24 and 25 generally illustrate one embodiment of a suture construct 10a in combination with the suture pin 62h for securing two bone fragments 125a, 125b. FIG. 26 generally illustrates one embodiment of a suture construct 10a in combination with the suture pin 62h for securing two bones 46, 47. FIGS. 27-30 generally illustrate various views of the suture pin 62h. As will described in more detail herein, the suture pin 62h reduces the amount of friction and/or force required to reduce the suture construct, thereby providing a greater tactile feel to the surgeon, minimizing potential damage to the bones/bone fragments, and/or providing sufficient strength/rigidity to the suture pin to prevent damage/failure of the suture pin while reducing the suture construct.

Figure 31:
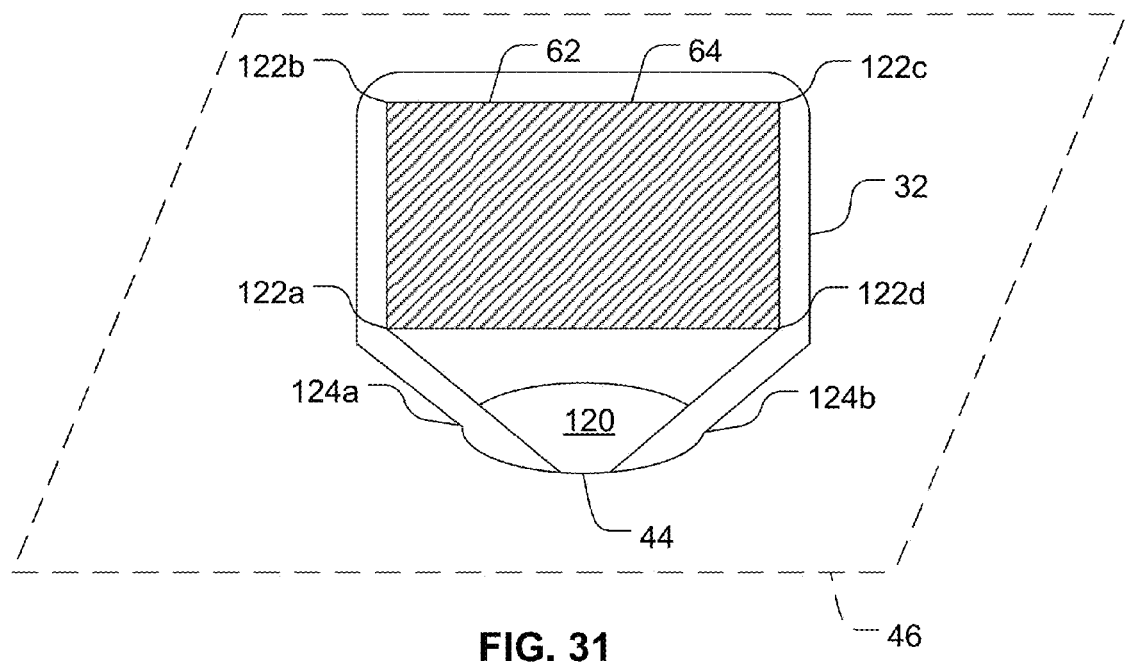
FIG. 31 illustrates a cross-sectional view of one embodiment of a suture pin and a contractible loop extending through an opening in a passageway.

As may be appreciated, the main body of the suture pin should be strong enough to prevent failure when reducing the suture construct. Put another way, if the suture pin is not strong enough, then the forces exerted against the suture pin by the suture construct will excessively bend the suture pin causing an unacceptable amount of deformation of the suture pin which can lead to bone damage or failure of the suture pin. As the cross-sectional thickness of the suture pin is increased, however, the main body of the suture pin begins to close/cover-over the opening in the bone defined by the passageway therethrough. An example of this is illustrated in FIG. 31. In particular, a cross-section of a suture pin 62 and the opening 120 of passageway 44 in the bone 46 is generally illustrated. The suture pin 62 includes a rectangular main body 64 over which the contractible loop 32 slides. Because the cross-sectional thickness of the main body 64 (i.e., the portion of the suture pin which extends across the opening 120) is larger than the diameter of the opening 120 to provide sufficient strength to the suture pin 62, the main body 64 will cover or block the opening 120. As the main body 64 blocks the opening 120, the contractible loop 32 is forced to travel between the main body 64 and the opening 120 and/or the contractible loop 32 is forced to cut a groove into the bone 46 in the area proximate to the opening 120 when the suture construct is reduced. Consequently, the suture pin 62 significantly increases the friction/resistance and reduces the tactile feel when reducing the suture construct.

In addition, the rectangular cross-section of the main body 64 significantly increases the amount of friction when reducing the suture construct. In particular, because the contractible loop 32 is forced to travel between the main body 64 and the opening 120, the contractible loop 32 must slide across the four corners 122a, 122b, 122c 122d of the main body 64 as well as two portion portions 124a, 124b of the perimeter of the opening 120. The four corners 122a, 122b, 122c 122d and portions 124a, 124b generate a very high stress and/or friction concentrations, thereby increasing the overall amount of force necessary to slide the contractible loop 32 when reducing the suture construct.

Referring back to FIGS. 24-30, the suture pin 62h is configured to minimize and/or eliminate the above described issues. In particular, the suture pin 62h includes a main body 64 having a generally circular cross-section extending between a first and a second enlarged portion 70. The main body 64 may include a length which is greater than the spacing of the bridge 18 to compensate for non-parallel passageways 44, 45. For example, for a bridge having a length of 10 mm, the main body 64 may include a length of 17 mm to 20 mm. The diameter of the main body 64 should be selected to prevent an undesirable amount of deformation and/or failure of the suture pin 62h based on the intended use of the suture construct. By way of an example, a suture pin 62h constructed from a titanium alloy used with a suture construct having a #4 suture to treat hallux valgus may include a main body 64 having a diameter of approximately 1 mm (which may be approximately equal to the diameter of the passageway 44). It should be appreciated, thought, that this is just an example, and that the diameter of the main body 64 of the suture pin 62h will depend on the intended application as well as the intended forces exerted by the suture system during reduction.

Figure 32:
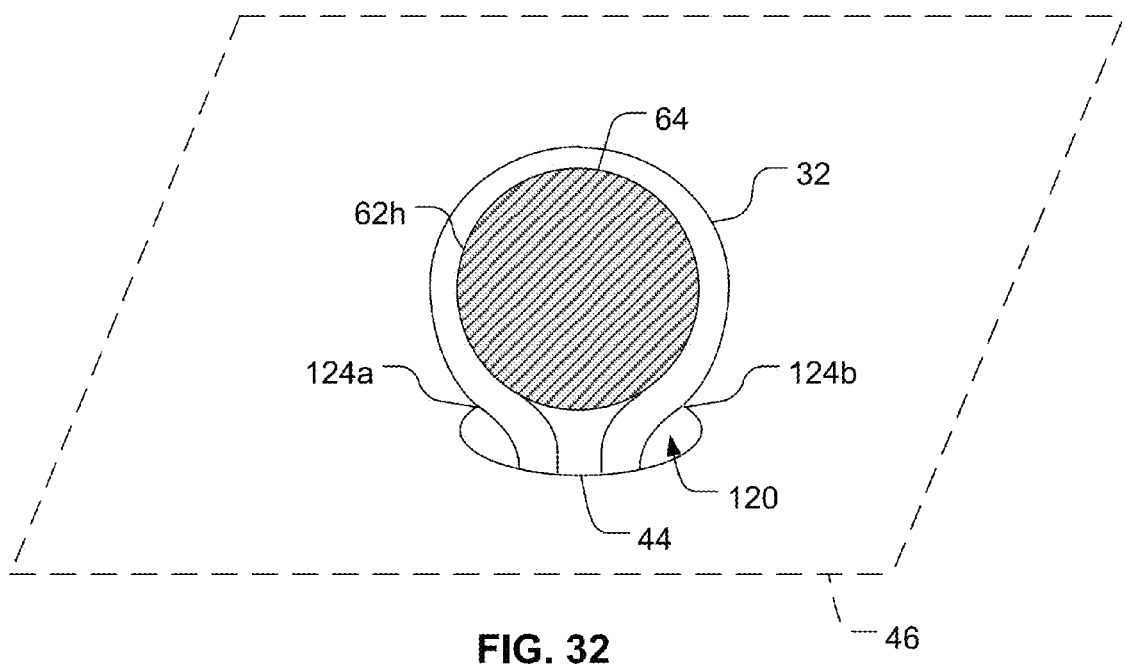
FIG. 32 illustrates a cross-sectional view of the suture pin of FIGS. 24 and 25 and a contractible loop extending through an opening in a passageway.

With reference to FIG. 32, a cross-section of the main body 64 of the suture pin 62h is illustrated along with the contractible loop 32 extending through the opening 120 of the passageway 44. Depending on the diameter of the main body 64, the suture pin 62h may eliminate the friction points (e.g., when the diameter of the main body 64 is less than the diameter of the opening 120 of the passageway 44) or may have only two friction points 104a, 124b which correspond to the locations where the contractible loop 32 passes between the main body 64 and the opening 120 (e.g., when the diameter of the main body 64 is equal to or greater than the diameter of the opening 120 of the passageway 44). The generally circular cross-section of the main body 64 acts as a pulley, thereby allowing the contractible loop 32 to slide smoothly around a portion of the perimeter of the main body 64 (e.g., greater than or equal to 180 degrees around the main body 64) as the contractible loop 32 is reduced. As a result, the suture pin 62h with a main body 64 having a generally circular cross-section reduces the amount of friction and/or force required to reduce the suture construct. Additionally, the reduction in friction points allows the suture pin 62h to provide a greater tactile feel to the surgeon and minimizes potential damage to the bones/bone fragments. Moreover, the overall strength of the suture pin 62h may be increased while preventing/minimizing the suture pin 62h from covering/blocking the opening 120 of the passageway 44.

With reference again to FIGS. 24-30, the enlarged portions 70 of the suture pin 62h may include a bone facing surface 126 having a generally concaved contour. The concaved contour is configured to allow the bone facing surface 126 to generally conform to the bone surface, e.g., to allow the bone facing surface 126 to sit generally congruent with the bone face. The concaved bone facing surface 126 helps distribute the forces exerted by the suture system more evenly across the bone 46 and also helps position the suture pin 62h during assembly/implanting of the suture system within passageway(s) 44, 45.

One or more of the enlarged portions 70 of the suture pin 62h may also feature one or more shoulders 127 extending outwardly beyond the main body 64. For example, the shoulders 127 may form a generally an arrowhead-like shape which extend outward and generally towards the opposite end (though the shoulders 127 may extend outward generally perpendicularly from the main body 64 or outward generally away from the opposite end). As discussed herein, the enlarged portions 70 may aid in keeping the contractible loop(s) 32, 34 disposed on the main body 64 during assembly/implanting of the suture system within passageway(s) 44, 45.

While the main body 64 is described having a generally circular cross-section, it may be appreciated that the main body 64 may also include a generally oval cross-section. Additionally, while the entire main body 64 is illustrated having a generally circular, it may be appreciated that only the portions or regions of the main body 64 over which the contractible loop(s) 28, 30 slide when reducing the suture construct may have a generally circular or oval cross-section. Moreover, while the suture pin 62h is illustrated having a first and a second enlarged portion 70, it may be appreciated that the main body 64 may extend between one or more reduced portions as disclosed herein.

Variations of the suture system and suture construct described herein are considered to be part of this disclosure. For example, while the suture construct the suture construct described above is generally symmetrical about the bridge (e.g., the suture construct is illustrated having first and second knots, first and second loops, first and second contractible loops, and first and second opposed loops separated by the bridge), the bridge section may be eliminated and the suture construct may feature only one half of the remaining construct (i.e., a single reduction construct). More specifically, the suture construct may alternatively include only one knot, one loop, one contractible loop, and one opposed loop. The contractible loop may be passed through a single passageway formed through the first and second bones. A first suture pin may be disposed through a distal end of the contractible loop against the first bone and a second splice pin may be disposed through a proximal end of the contractible loop against the second bone. The suture construct may then be tightened by pulling on the locking limb of the suture using a pusher or pusher tube as generally described herein. Once the desired amount of force is applied by the suture construct, the tension on the suture construct causes the opposed loop to reduce against the locking limb, thereby locking the suture construct and preventing the suture construct from loosening. Once the suture construct is locked, the locking limb may be trimmed proximate to the opposed loop.

One or more of the suture systems consistent with the present disclosure provide numerous advantages. For example, the suture systems may include an all thread (suture) repair device which does not require the surgeon to tie any knots, welds, or the like in order to secure and/or draw the suture system tight. The elimination of knots is significant because many surgeons are uncomfortable tying knots due to the possibility of the knot becoming loose and/or the difficulty associated with tying a knot during a surgical procedure. Additionally, welding increases the possibility of accidental collateral damage to surrounding tissue and may be difficult during a surgical procedure.

Additionally, the suture systems consistent with the present disclosure eliminate the need to pass buttons, pledgets, or the like through passageways formed in the bone. As a result, the passageways formed in the bone may have a smaller diameter and may minimize the potential of causing incidental complications (such as, but not limited to, damaging the bones during drilling and/or cracking the bones after installation).

The suture systems consistent with the present disclosure also provide an "equilibrium" construct. More specifically, the suture systems consistent with the present disclosure distribute the compressive force generated by the suture system evenly across the entire suture system. In contrast, other suture systems utilize two separate and distinct sutures. Consequently, one suture may exert more compressive force than the other suture. This uneven compressive force may place additional stress on the tissue and/or bones, and may lead to the tissue or bones failing.

According to one aspect, the present disclosure features a suture system including a suture construct having a first reduction construct configured to be selectively arranged in an expanded state and a reduced state. The first reduction construct includes a first locking limb, a first contractible loop, and a first opposed loop disposed generally opposite to the first contractible loop, wherein reduction of the first opposed loop contracts the first contractible loop from the expanded state into the reduced state and secures the suture construct in the reduced state. The suture construct may also include a second reduction construct.

According to another aspect, the present disclosure features a suture system including a first and a second reduction construct separated by a bridge. Each of the reduction constructs features a knot defining a loop, a contractible loop and an opposed loop separated by the loop, and a locking limb extending from the loop and the opposed loop. Each of the reduction constructs is configured to be selectively reduced from an expanded state to a reduced state by reducing a length of the contractible loop by urging the locking limb through the loop from the opposed loop, thereby advancing a portion of the contractible loop through the loop and into the opposed loop.

According to yet another aspect, the present disclosure features a suture system including a first and a second reduction construct separated by a bridge. Each of the reduction constructs is configured to be selectively arranged in an expanded state and a reduced state and each includes a locking limb, a contractible loop, and an opposed loop disposed generally opposite to the contractible loop. Reduction of the opposed loop contracts the contractible loop from the expanded state into the reduced state and secures the suture construct in the reduced state.

According to yet a further aspect, the present disclosure features a suture pin including a first and a second enlarged portion and an elongated body portion extending between the first and the second enlarged portion. The elongated body portion has a generally circular cross-section. The first and the second enlarged portion have a cross-section which greater than a cross-section of the elongated body portion.

According to another aspect, the present disclosure features a method for securing two bones together using a suture system. The method includes forming a first and a second passageway, each extending through a first and a second bone; advancing a distal portion of a first and a second contractible loop through a respective one of the first and the second passageways until the distal ends extend beyond the first bone, wherein proximal regions of the first and the second contractible loops are separated by a bridge, the bridge being disposed proximate to the second bone; advancing a suture plate through the distal portion of the first and the second contractible loops extending beyond the first bone; and reducing the first and the second contractible loops disposed within the first and the second passageways by advancing a first and a second locking limb from a first and a second opposed loop and through a first and a second loop, respectively, thereby advancing portions of the first and second contractible loops through the first and the second loops and into the first and second opposed loops.

According to yet a further aspect, the present disclosure features a method for forming a suture construct. The method includes providing a length of suture; forming a first and a second knot and a first and a second loop, respectively, in the suture, the first and second knots being separated by a bridge; and passing intermediate portions of the suture through the first and the second loops to form a first and a second contractible loop and a first and a second opposed loop, respectively, wherein a first and a second locking limb extends from the first and the second opposed loops through the first and the second loops, respectively.

It should be appreciated that various features of the different embodiments described herein may be combined together.

While the principles of the present disclosure have been described herein, it is to be understood by those skilled in the art that this description is made only by way of example and not as a limitation as to the scope of the invention. The features and aspects described with reference to particular embodiments disclosed herein are susceptible to combination and/or application with various other embodiments described herein. Such combinations and/or applications of such described features and aspects to such other embodiments are contemplated herein. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

Additional disclosure in the format of claims is set forth below:

What is claimed is:

1. A suture system comprising:
   a suture construct including a first reduction construct configured to be selectively arranged in an expanded state and a reduced state, said first reduction construct comprising:
   a first locking limb;
   a first contractible loop; and
   a first opposed loop disposed generally opposite to said first contractible loop, wherein reduction of said first opposed loop contracts said first contractible loop from said expanded state into said reduced state and secures said suture construct in said reduced state; and
   a suture pin configured to be disposed through said first contractible loop, wherein said suture pin includes an elongated main body having a generally circular cross-section extending between a first and a second enlarged portion, said first and said second enlarged portions extending outwardly from said elongated main body.

2. The suture system of claim 1, wherein said first contractible loop and said first opposed loop are separated by a first loop defined by a first knot.

3. The suture system of claim 2, wherein a length of said first contractible loop is reduced by pulling said locking limb, causing a portion of said suture to pass from said first contractible loop and through said first knot, and through said first opposed loop.

4. The suture system of claim 2, wherein said first locking limb is configured to be disposed through said first opposed loop to lock said suture construct.

5. The suture system of claim 1, further comprising a second reduction construct separated from said first reduction construct by a bridge, said second reduction construct comprising:
   a second locking limb;
   a second contractible loop; and
   a second opposed loop disposed generally opposite to said second contractible loop, wherein reduction of said second opposed loop contracts said second contractible loop.

6. The suture system of claim 5, further comprising a suture pin configured to be disposed through said first and said second contractible loops.

7. The suture system of claim 6, wherein said suture pin comprises an elongated body portion.

8. A suture system comprising:
   a suture construct including a first reduction construct configured to be selectively arranged in an expanded state and a reduced state, said first reduction construct comprising:
   a first locking limb;
   a first contractible loop; and
   a first opposed loop disposed generally opposite to said first contractible loop, said first contractible loop and said first opposed loop being separated by a first loop defined by a first knot, wherein reduction of said first opposed loop contracts said first contractible loop from said expanded state into said reduced state and secures said suture construct in said reduced state;
   wherein a first portion of said first opposed loop extends through said first loop from said first contractible loop, and wherein a second portion of said first opposed loop extends through said first loop and terminates at said first locking limb.

9. The suture system of claim 8, further comprising a suture pin configured to be disposed through said first contractible loop.

10. The suture system of claim 9, wherein said suture pin includes an elongated main body having a generally circular cross-section extending between a first and a second enlarged portion, said first and said second enlarged portions extending outwardly from said elongated main body.

11. The suture system of claim 10, wherein said first and said second enlarged portions include a generally concaved bone facing surface.

12. The suture system of claim 8, wherein a first portion of said first contractible loop extends through said first loop from said first opposed loop, and wherein a second portion of said first contractible loop extends from and terminates at said first knot.

13. A suture system comprising:
   a first suture construct including a first reduction construct configured to be selectively arranged in an expanded state and a reduced state, said first reduction construct comprising:
   a first locking limb;
   a first contractible loop; and
   a first opposed loop disposed generally opposite to said first contractible loop, wherein reduction of said first opposed loop contracts said first contractible loop from said expanded state into said reduced state and secures said suture construct in said reduced state;
   a second reduction construct separated from said first reduction construct by a bridge, said second reduction construct comprising:
   a second locking limb;
   a second contractible loop; and
   a second opposed loop disposed generally opposite to said second contractible loop,
   wherein reduction of said second opposed loop contracts said second contractible loop; wherein said first and said second contractible loops and said first and said second opposed loops are separated by a first and a second loop defined by first and second knots, respectively.

14. The suture system of claim 13, wherein first portions of said first and said second opposed loops extend through said first said second loops from said first said second contractible loops, respectively, and wherein second portions of said first said second opposed loops extend through said first said second loops and terminate at said first said second locking limbs, respectively.

15. The suture system of claim 14, wherein first portions of said first said second contractible loops extend through said first said second loops from said first said second opposed loops, respectively, and wherein second portions of said first said second contractible loops extend from and terminate at said first said second knots, respectively.

16. The suture system of claim 13, wherein said first and said second locking limbs are passed through said first and said second opposed loops, respectively.

17. The suture system of claim 16, further comprising a first and a second pusher tube defining a first and a second lumen, respectively, wherein said first and said second pusher tubes are advanced over portions of said first and second opposed loops, respectively, and wherein distal portions of said first and second opposed loops extend beyond said first and second pusher tubes, respectively.

18. The suture system of 17, wherein a proximal end of said first and second pusher tubes abuts against at least one of said first and said second knots or said first and second loops, respectively.

19. The suture system of claim 17, wherein said first and second pusher tubes each comprise an outrigger extending outward from the longitudinal axis of the said first and second pusher tubes.

20. The suture system of claim 17, wherein said first and second pusher tubes each comprise at least two outriggers which form a cradle.

21. The suture system of claim 17, further comprising at least one marking indicia to identify a hot side of said first and second opposed loops.

22. A suture system comprising:
a first suture construct including a first reduction construct configured to be selectively arranged in an expanded state and a reduced state, said first reduction construct comprising:
a first locking limb;
a first contractible loop; and
a first opposed loop disposed generally opposite to said first contractible loop, wherein reduction of said first opposed loop contracts said first contractible loop from said expanded state into said reduced state and secures said suture construct in said reduced state;
a second reduction construct separated from said first reduction construct by a bridge, said second reduction construct comprising:
a second locking limb;
a second contractible loop; and
a second opposed loop disposed generally opposite to said second contractible loop, wherein reduction of said second opposed loop contracts said second contractible loop; and
a suture pin configured to be disposed through said first and said second contractible loops; said suture pin comprising an elongated body portion and at least one enlarged portion having a cross-section which is greater than a cross-section of said elongated body portion.

23. The suture system of claim 22, wherein said suture pin comprises at least two enlarged portions separated by a distance which is substantially equal to or greater than a length of said bridge.

24. The suture system of claim 23, wherein said elongated body portion has a generally circular cross-section.

25. The suture system of claim 24, wherein said enlarged portions include a generally concaved bone facing surface.

26. A suture system comprising:
a first suture construct including a first reduction construct configured to be selectively arranged in an expanded state and a reduced state, said first reduction construct comprising:
a first locking limb;
a first contractible loop; and
a first opposed loop disposed generally opposite to said first contractible loop, wherein reduction of said first opposed loop contracts said first contractible loop from said expanded state into said reduced state and secures said suture construct in said reduced state;
a second reduction construct separated from said first reduction construct by a bridge, said second reduction construct comprising:
a second locking limb;
a second contractible loop; and
a second opposed loop disposed generally opposite to said second contractible loop, wherein reduction of said second opposed loop contracts said second contractible loop; and
a suture plate configured to be proximate to said bridge, said suture plate including two apertures spaced apart from each other a distance substantially equal to a length of said bridge.

27. A suture system comprising:
a first and a second reduction construct separated by a bridge, each of said reduction constructs comprising:
a knot defining a loop;
a contractible loop and an opposed loop separated by said loop; and
a locking limb extending through said loop and from said opposed loop;
wherein each of said reduction constructs is configured to be selectively reduced from an expanded state to a reduced state by reducing a length of said contractible loop by urging said locking limb through said loop from said opposed loop, thereby advancing a portion of said contractible loop through said loop and into said opposed loop.

28. The suture system of claim 27, further comprising a suture pin configured to be disposed through each of said contractible loops.

29. The suture system of claim 28, wherein said suture pin comprises an elongated body portion having a length greater than a length of said bridge, and at least one enlarged portion having a cross-section which is greater than a cross-section of said elongated body portion.

30. The suture system of claim 29, wherein said elongated body portion has a generally circular cross-section.

31. The suture system of claim 30, wherein said enlarged portions include a generally concaved bone facing surface.

32. A method for forming a suture construct comprising:
providing a length of suture;
forming a first and a second knot and a first and a second loop, respectively, in the suture, said first and second knots being separated by a bridge; and
passing intermediate portions of said suture through said first and said second loops to form a first and a second contractible loop and a first and a second opposed loop, respectively, wherein a first and a second locking limb extends from said first and said second opposed loops through said first and said second loops, respectively.

* * * * *

UNITED STATES PATENT AND TRADEMARK OFFICE
CERTIFICATE OF CORRECTION

PATENT NO. : 9,492,200 B2  
APPLICATION NO. : 13/863917  
DATED : November 15, 2016  
INVENTOR(S) : George Sikora et al.

Page 1 of 1

It is certified that error appears in the above-identified patent and that said Letters Patent is hereby corrected as shown below:

In the Claims

In Column 17, Line 22, in Claim 18, after "of" insert -- claim --.

Signed and Sealed this  
Twenty-fourth Day of January, 2017

Michelle K. Lee  
*Director of the United States Patent and Trademark Office*